United States Patent
Oohisa et al.

(10) Patent No.: US 9,640,775 B2
(45) Date of Patent: May 2, 2017

(54) ORGANIC ELECTROLUMINESCENCE ELEMENT

(75) Inventors: Satoru Oohisa, Hachioji (JP); Yoshiyuki Suzuri, Hino (JP); Shuri Sato, Yokohama (JP)

(73) Assignee: KONICA MINOLTA, INC., Tokyo (JP)

( * ) Notice: Subject to any disclaimer, the term of this patent is extended or adjusted under 35 U.S.C. 154(b) by 697 days.

(21) Appl. No.: 14/003,108

(22) PCT Filed: Mar. 1, 2012

(86) PCT No.: PCT/JP2012/055228
§ 371 (c)(1),
(2), (4) Date: Sep. 4, 2013

(87) PCT Pub. No.: WO2012/121101
PCT Pub. Date: Sep. 13, 2012

(65) Prior Publication Data
US 2013/0341612 A1  Dec. 26, 2013

(30) Foreign Application Priority Data
Mar. 4, 2011  (JP) ................... 2011-047301

(51) Int. Cl.
| | | |
|---|---|---|
| *C09K 11/06* | (2006.01) | |
| *H01L 51/50* | (2006.01) | |
| *C07D 209/86* | (2006.01) | |
| *C07D 405/10* | (2006.01) | |
| *C07D 405/14* | (2006.01) | |
| *C07D 409/14* | (2006.01) | |
| *C07D 471/04* | (2006.01) | |
| *H05B 33/14* | (2006.01) | |
| *H01L 51/00* | (2006.01) | |
| *H01L 51/52* | (2006.01) | |

(52) U.S. Cl.
CPC ........ *H01L 51/5024* (2013.01); *C07D 209/86* (2013.01); *C07D 405/10* (2013.01); *C07D 405/14* (2013.01); *C07D 409/14* (2013.01); *C07D 471/04* (2013.01); *C09K 11/06* (2013.01); *H01L 51/0072* (2013.01); *H01L 51/0085* (2013.01); *H05B 33/14* (2013.01); *H01L 51/0071* (2013.01); *H01L 51/5016* (2013.01); *H01L 51/5036* (2013.01); *H01L 51/5246* (2013.01); *H01L 2251/5384* (2013.01)

(58) Field of Classification Search
CPC .. C07D 209/86; C07D 405/10; C07D 405/14; C07D 409/14; C07D 471/04; H01L 51/0072; H01L 51/0085; H01L 51/5024; C09K 11/06; H05B 33/14
USPC ............. 257/40; 252/301.16; 313/504, 506; 428/917
See application file for complete search history.

(56) References Cited

U.S. PATENT DOCUMENTS

| | | | | |
|---|---|---|---|---|
| 7,629,060 | B2 * | 12/2009 | Oshiyama | C09K 11/06 257/102 |
| 7,745,990 | B2 * | 6/2010 | Kondo | C09K 11/06 313/504 |
| 7,759,855 | B2 * | 7/2010 | Oshiyama | C09K 11/06 313/503 |
| 7,790,890 | B2 * | 9/2010 | Oshiyama | C09K 11/06 257/E51.041 |
| 2004/0115476 | A1 * | 6/2004 | Oshiyama | C09K 11/06 428/690 |
| 2004/0178721 | A1 * | 9/2004 | Oshiyama | C09K 11/06 313/504 |
| 2007/0196687 | A1 * | 8/2007 | Oshiyama | C09K 11/06 428/690 |
| 2008/0238305 | A1 * | 10/2008 | Kondo | C09K 11/06 313/504 |

FOREIGN PATENT DOCUMENTS

| | | |
|---|---|---|
| JP | 2005-228737 A | 8/2005 |
| JP | 2005-310639 A | 11/2005 |
| JP | 2007-189002 A | 7/2007 |

(Continued)

OTHER PUBLICATIONS

International Preliminary Report on Patentability and Written Opinion in Japanese and English, date of issuance: Sep. 10, 2013 (13 pages).

(Continued)

*Primary Examiner* — Douglas McGinty
(74) *Attorney, Agent, or Firm* — Lucas & Mercanti, LLP

(57) ABSTRACT

Provided is an organic EL element having a high emission efficiency, a light emission life, and excellent high-temperature preservation stability. This organic electroluminescence element has at least one light-emitting layer between a positive electrode and a negative electrode. The light-emitting layer comprises at least one type of light-emitting dopant and at least three types of non-emitting organic materials represented by general formula (2); of the non-emitting organic materials, the material with the largest molecular weight has a molecular weight of 1,500 or less; and the minimum content of the non-emitting organic materials is 1 mass % or greater.

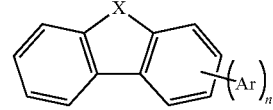

General formula (2)

7 Claims, 1 Drawing Sheet

(56) References Cited

FOREIGN PATENT DOCUMENTS

| JP | 2008-270190 A | 11/2008 |
|---|---|---|
| JP | 2009-93981 A | 4/2009 |
| JP | 2009-266673 A | 11/2009 |
| JP | 2009-289716 A | 12/2009 |
| JP | 2010-135467 A | 6/2010 |
| JP | 2011-9517 A | 1/2011 |
| JP | 2011-71452 A | 4/2011 |
| WO | WO 2005/057678 A1 | 6/2005 |
| WO | WO 2006/112265 A1 | 10/2006 |

OTHER PUBLICATIONS

International Search Report of PCT/JP2012/055228 dated May 22, 2012.

Chin-Ti Chen et al; Solution Processed Molecular Materials in the Fabrication of Flexible Phosphorescence-Based OLEDs; SID 10 Digest; 2010; pp. 548-551.

Daisuke Yokoyama et al; Enhancement of Electron Transport by Horizontal Molecular Orientation of Oxadiazole Planar Molecules in Organic Amorphous Films; Applied Physics Letters 95; 2009.

* cited by examiner

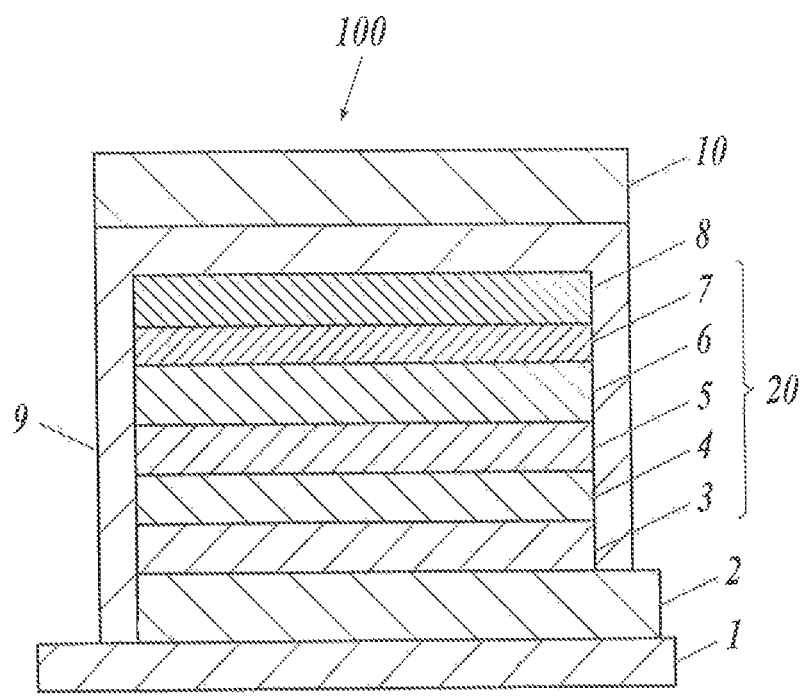

ORGANIC ELECTROLUMINESCENCE ELEMENT

CROSS-REFERENCE TO RELATED APPLICATIONS

This application is a 371 PCT/JP 2012/055228 filed Mar. 1, 2012, which claims priority of Japanese Application Ser. No. 2011-047301 filed on Mar. 4, 2011, the entire contents of each of which are incorporated herein by reference.

TECHNICAL FIELD

The present invention relates to an organic electroluminescence element achieving high efficiency of light emission, improved stability for long-term driving and excellent storage stability in high temperature.

BACKGROUND ART

In recent years, an organic electroluminescence element employing an organic compound(s) (hereinafter also referred to as an "organic EL element" arbitrarily) has been highly expected for its applications to, for example, a large-sized full-colored display element of solid-state light emission available at a low price and to writing light source arrays. Thus, research and development of such an organic electroluminescence element have been actively conducted.

An organic EL element is a thin all-solid-state element composed of a pair of an anode and cathode formed directly or indirectly on a film and an organic functional layer provided between the anode and the cathode, and the organic functional layer which may consists of a single or multiple layers contains an organic light-emitting compound(s) and has a thickness of only about 0.1 µm.

It is known that when a relatively low voltage of about 2 to 20 V is applied to such an organic EL element, electrons are injected from a cathode to an organic compound layer, and electron holes are injected from an anode to the organic compound layer; then these electrons and electron holes are recombined with each other in a light-emitting layer, and energy is released as light upon return of an electron energy level from a conduction band to a valence bond. This technique is expected for use in future flat displays and lighting devices.

In addition, an organic EL element utilizing phosphorescence emission, which has been recently found, can achieve efficiency of light emission of about four times larger in principle than that of a conventional element utilizing fluorescence emission. Thus, research and development regarding layer configurations and electrodes of a light-emitting element utilizing phosphorescence emission, as well as developments of materials for an element utilizing phosphorescence emission, have been extensively conducted all over the world.

In particular, as one of measures for preventing global warming, an organic EL element utilizing phosphorescence emission has begun to be considered to be applied to lighting devices, which currently consumes large part of energy that human consumes. Hence, an organic EL element utilizing phosphorescence emission is extensively studied for improving its efficiency and for decreasing costs for practical realization of a white light-emitting panel, which can be an alternative for conventional lighting devices.

A white light-emitting panel used for lighting is required to have high efficiency and long lifetime. Particularly as to length of lifetime, a white light-emitting panel is inferior to a fluorescent light and white light-emitting LED at present. Thus, various studies for achieving higher efficiency and longer lifetime have been conducted.

Performance of an organic EL element largely depends on thin film morphology. Generally, thin layers in an organic EL element are preferably amorphous.

To provide amorphous thin films, there is a method for preventing crystallization of an organic compound(s) for an organic layer in heating including steps of conducting application of the organic material(s) in an inert gas atmosphere and conducting heating and drying at a temperature 10° C. or more lower than a glass transition temperature Tg of the material in an inert gas atmosphere (see Patent Document 1, for example)

In recent years, it has been recognized as important to control molecular orientation in an amorphous film for controlling electrical and optical properties of an organic EL element. Yokoyama et al. have conducted detail investigations regarding molecular orientation in an amorphous film, and reveal that the molecular orientation largely affects electric charge-transporting properties (see Non-patent Document 1, for example).

Use of flat molecules achieves tight packing, and also improves electrical properties by enhancing interaction between π electrons. However, this method cannot be used for a light-emitting layer generally containing dopant molecules that are not flat.

To improve electrical properties of a light-emitting layer, use of two types of host molecules in combination has been proposed. Improvement in electrical properties is achieved by mixing one type of a host for transporting electron holes with another type of a host for transporting electrons (see Patent Document 2, for example)

This method can easily achieve valance of carriers, whereas in the case of using one type of a host, valance of carriers is difficult to be achieved. However, this method is also difficult to achieve tight packing. Further, considering based on a single carrier, change in packing state may degrade electricity-transporting properties compared to the case of using each of the two types of hosts.

In addition, it has been proved that use of three types of hosts in a light-emitting layer containing non-light-emitting organic materials PVK and OXD-7 improves performances (see Non-Patent Document 2, for example)

In Non-Patent Document 2, large improvement in performances is achieved by simply adding a third type of a host, SimCP2, to obtain a concentration of 8% by mass. Non-patent Document 2 does not describe detail discussions of the reasons of this improvement, but this improvement is probably achieved by confinement effect of excitons by SimCP2 having a large T1. However, further improvements in efficiency and lifetime are desired.

Generally, orientations of molecules in an amorphous film are different, and thus interactions between the molecules are weak. Therefore, an amorphous film has not sufficient electrical properties. In addition, some molecules may be present as fine crystals. In this case, these crystals may function as cores for forming larger crystals in an amorphous film, which causes larger effects of grain boundary and scatters carriers, resulted in shorter lifetime of an element.

Further, fine crystals in a film grow as temperature rises, which makes storage stability in high temperature insufficient.

As described above, an amorphous film has many problems to be solved. In addition, not much is known about a film formed by application of a low-molecular compound(s). Therefore, it has been desired to solve these problems.

PRIOR ART DOCUMENT

Patent Document

Patent Document 1 Japanese Patent Application Laid-open Publication No, 2005-310639

Patent Document 2: Japanese Patent Application Laid-open Publication No. 2007-515788

Non-Patent Document

Non-Patent Document 1: Appl. Phys. Lett. 95, 243303 (2009)

Non-Patent Document 2 SID2010 Proceedings 39.1

SUMMARY OF THE INVENTION

Problems to be Solved by the Invention

An object of the present invention is to provide an organic EL element achieving high power efficiency, excellent stability for long-term driving and high storage stability in high temperature (suppression of voltage rise after storage in high temperature).

Means for Solving Problems

The above object of the present invention is accomplished by the following configurations.

1. An organic electroluminescence element including an anode, a cathode and one or more light-emitting layers provided between the anode and the cathode, wherein the one or more light-emitting layers include at least one type of a light-emitting dopant and at least three types of non-light-emitting organic materials in total, a largest molecular weight among molecular weights of the at least three types of the non-light-emitting organic materials is 1500 or less, and a minimum content of the at least three types of the non-light-emitting organic materials is 1% by mass or more, the non-light-emitting organic materials being represented by a following general formula (2):

[Chemical fomula 1]

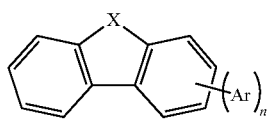

General formula (2)

wherein in the formula, X represents NR', PR'R"R'", CR'R" or SiR'R"; R', R" and R'" each represent a hydrogen atom or a substituent; Ar represents an aromatic hydrocarbon ring or an aromatic hetero ring; and n represents an integer from 0 to 8.

2. The organic electroluminescence element of the above 1, wherein at least one of the at least three types of the non-light-emitting organic materials is a compound represented by a following general formula (3):

[Chemical fomula 2]

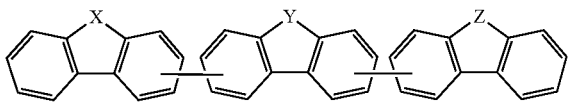

General formula (3)

wherein in the formula, X, Y and Z each represent NR', O, S, PR', PR'R"R'", CR'R" or SiR'R"; R', R" and R'" each represent a hydrogen atom or a substituent; and a benzene ring optionally includes a substituent.

3. The organic electroluminescence element of the above 1 or 2, wherein five types of the non-light-emitting organic materials represented by the general formula (2) are contained.

4. The organic electroluminescence element of any one of the above 1, to 3, wherein a content (% by mass) of each of multiple types of the non-light-emitting organic materials increases with increase of molecular weight of each of the multiple types of the non-light-emitting organic materials.

5. The organic electroluminescence element of any one of the above 1 to 4, wherein among molecular weights of the at least three types of the non-light-emitting organic materials represented by the general formula (2), a difference between a largest molecular weight M (max) and a smallest molecular weight M (min) is less than 250.

6. The organic electroluminescence element of any one of the above 1 to 5, wherein at least one type of the light-emitting dopant is a phosphorescence-emitting dopant.

7. The organic electroluminescence element of the above 6, wherein the phosphorescence-emitting dopant is represented by a following general formula (1)

[Chemical formula 3]

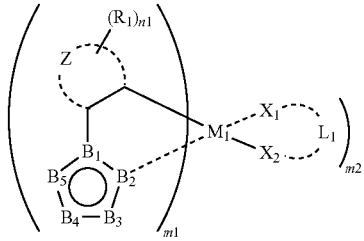

General formula (1)

wherein in the formula, $R_1$ represents a substituent; Z represents a non-metal atom group necessary for forming a five to seven-membered ring; n1 represents an integer from 0 to 5; $B_1$ to $B_5$ each represent a carbon atom, a nitrogen atom, an oxygen atom or a sulfur atom, and at least one of $B_1$ to $B_5$ represents a nitrogen atom; $M_1$ represents a transition metal of Group 8 to 10 on a periodic table; $X_1$ and $X_2$ each represent a carbon atom, a nitrogen atom or an oxygen atom; $L_1$ represents a atom group forming a bidentate ligand with $X_1$ and $X_2$; m1 represents an integer 1, 2 or 3; m2 represents an integer 0, 1 or 2; and m1+m2 is 2 or 3.

EFFECTS OF THE INVENTION

The present invention can provide an organic EL element achieving high efficiency of light emission, long lifetime of light emission and high storage stability in high temperature.

BRIEF DESCRIPTION OF THE DRAWING

The FIGURE is a cross-sectional view illustrating a schematic configuration of an organic electroluminescence element.

EMBODIMENTS FOR CARRYING OUT THE INVENTION

Preferred embodiments of the present invention will be described with reference to the drawing.

<<Configuration of Organic Electroluminescence Element (Organic EL Element)>>

The FIGURE is a cross-sectional view illustrating a schematic configuration of an organic electroluminescence element (organic EL element) of the present invention. This is an illustration of an example of preferred embodiments.

In the FIGURE, an organic electroluminescence element (hereinafter also referred to as an organic EL element) 100 includes a flexible supporting substrate 1. On the flexible supporting substrate 1, an anode 2 is formed. On the anode 2, an organic functional layer 20 is formed. On the organic functional layer 20, a cathode 8 is formed.

The organic functional layer 20 represents a layer(s) provided between the anode 2 and the cathode 8 and being constituents of the organic electroluminescence element 100.

The organic functional layer 20 includes an electron hole-injecting layer 3, an electron hole-transporting layer 4, a light-emitting layer 5, an electron-transporting layer 6 and an electron-injecting layer 7, and may further include an electron hole-blocking layer, an electron-blocking layer and the like.

The anode 2, the organic functional layer 20 and the cathode 8, all of which are directly or indirectly on the flexible supporting substrate 1, are sealed with a flexible sealing member 10 via a sealing adhesive 9.

The layer configuration of the organic El element 100 (see the FIGURE) is merely a preferred specific example, and the present invention is not limited thereto.

The organic EL element 100 of the present invention may have any of configurations (i) to (viii) below, for example.

(i) flexible supporting substrate/anode/light-emitting layer/electron-transporting layer/cathode/heat-conducting layer/sealing adhesive/sealing member (ii) flexible supporting substrate/anode/electron hole-transporting layer/light-emitting layer/electron-transporting layer/cathode/heat-conducting layer/sealing adhesive/sealing member (iii) flexible supporting substrate/anode/electron hole-transporting layer/light-emitting layer/electron hole-blocking layer/electron-transporting layer/cathode/heat-conducting layer/sealing adhesive/sealing member (iv) flexible supporting substrate/anode/electron hole-transporting layer/light-emitting layer/electron hole-blocking layer/electron-transporting layer/cathode buffer layer/cathode/heat-conducting layer/sealing adhesive/sealing member (v) flexible supporting substrate/anode/anode buffer layer/electron hole-transporting layer/light-emitting layer/electron hole-blocking layer/electron-transporting layer/cathode buffer layer/cathode/heat-conducting layer/sealing adhesive/sealing member (vi) glass supporting body/anode/electron hole-injecting layer/light-emitting layer/electron-injecting layer/cathode/sealing member (vii) glass supporting body/anode/electron hole-injecting layer/electron hole-transporting layer, light-emitting layer/electron-injecting layer/cathode/sealing member (viii) glass supporting body/anode/electron hole-injecting layer/electron hole-transporting layer/light-emitting layer/electron-transporting layer/electron-injecting layer/cathode/sealing member <<Organic Functional Layer 20 of Organic EL Element>>

Details of the organic functional layer as a constituent of the organic EL element of the present invention will be described.

(1) Light-Emitting Layer 5

The light-emitting layer of the organic EL element of the present invention will be described.

The light-emitting layer of the organic EL element of the present invention is a layer where electrons and electron holes are injected from the electrodes (cathode, anode), the electron-transporting layer or the electron hole-transporting layer are recombined with each other and light is then emitted. Light-emitting portions may be in the light-emitting layer or at the interface between the light-emitting layer and an adjacent layer.

The total thickness as to the light-emitting layer(s) of the present invention is preferably 1 to 100 nm, and more preferably, to achieve much lower driving voltage, 50 nm or less. The total thickness as to the light-emitting layer(s) in the context of the present invention means, in the case of where a non-light-emitting interlayer(s) are provided between the light emitting layers, the sum of the thicknesses of the light-emitting layers and the non-light-emitting interlayer(s).

The thickness of each light-emitting layer is adjusted to preferably 1 to 50 nm. The relations between the respective thicknesses of a blue light-emitting layer, a green light-emitting layer and a red light-emitting layer is not particularly limited.

The light-emitting layer may be obtained by forming a film with a light-emitting material(s) and host compound(s) described later by a known method for forming thin layers such as vacuum deposition, spin coating, casting, LB method, ink jetting and the like.

In the present invention, multiple types of light-emitting materials may be mixed with each other in each of the light-emitting layers, and a phosphorescence-emitting material(s) and fluorescence-emitting material(s) may be contained in a single light-emitting layer.

A preferred configuration of the light-emitting layer of the present invention is that the light-emitting layer contains a host compound(s) and light-emitting material(s) (also referred to as light-emitting dopant(s) or light-emitting dopant compound(s)) and the light-emitting material(s) emit light.

Details of the host compound and the light-emitting material will be described later.

The present inventors have eagerly studied for improving performances of an organic electroluminescence element, and found that the light-emitting layer containing at least one type of the light-emitting dopant and at least three types of the non-light-emitting organic materials represented by the general formula (2), wherein a largest molecular weight among molecular weights of the non-light-emitting organic materials is 1500 or less, and a minimum content among contents of the non-light-emitting organic materials is 1% by mass or more, achieves the above-described effects of the present invention (i.e., improvement in efficiency of light emission, lengthening of lifetime and improvement in storage stability in high temperature).

<<Non-Light-Emitting Organic Material Represented by General Formula (2)>>

The non-light-emitting organic material represented by the general formula (2) of the present invention will be described.

The non-light-emitting organic material represented by the general formula (2) of the present invention may have carrier transporting properties, but the present invention includes the case where the non-light-emitting organic material represented by the general formula (2) of the present invention does not have carrier transporting properties.

The number of types of the non-light-emitting organic materials represented by the general formula (2) of the present invention to be contained is 3 or more, preferably 4 or more, and to achieve high efficiency of light emission, preferably 5 or more, more preferably 10 or more, and further more preferably from 10 to 15

The organic EL element of the present invention may include multiple light-emitting layers. In order to achieve the above-described effects of the present invention, the present invention is characterized in that the light-emitting layer(s) contain at least one type of the light-emitting dopant and at least three types of the non-light-emitting organic materials represented by the general formula (2), wherein a largest molecular weight among molecular weights of the non-light-emitting organic materials is 1500 ones, and a minimum content among contents of the non-light-emitting organic materials is 1% by mass or more.

At least three types of the non-light-emitting organic materials represented by the general formula (2) may be contained in a single light-emitting layer. In the case where the organic EL element of the present invention includes multiple light-emitting layers, one light-emitting layer may contain two types of the non-light-emitting organic materials represented by the general formula (2) and the other light-emitting layer may contain one type of the non-light-emitting organic material represented by the general formula (2), for example.

That is, in the both cases where the organic EL element of the present invention includes a single light-emitting layer or multiple light-emitting layers, at least three types of the non-light-emitting organic materials represented by the general formula (2) are contained in the one or more light-emitting layers in total.

A preferable case is the case where a single light-emitting layer contains at least three types of the non-light-emitting organic materials represented by the general formula (2)

The term "non-light-emitting" as to the non-light-emitting organic material means that when the organic EL element emits light, the number of photons emitted from the non-light-emitting organic material(s) is 1% or less with respect to the number of photons emitted from the light-emitting dopant(s) at optical wavelengths (wavelengths from 400 to 780 nm).

The light-emitting layer(s) of the present invention contain at least three types of the non-light-emitting organic materials represented by the general formula (2), and thus electrical properties of the organic EL element of the present invention is improved and longer lifetime is achieved. The present inventors presume that this is because packing is improved as described below, whereas definite reasons are not revealed.

As described in Non-Patent Document 1, to improve electrical properties of an amorphous film, increasing interactions between molecules (especially pi interactions) is effective. To increase interactions between molecules, it is important to increase overlap of wave functions of molecules.

In an amorphous film, however, orientations of molecules are different, and thus packing density is small. Therefore, intermolecular distances are large, and overlap of wave functions of molecules is smaller compared to that of crystals.

Generally, carriers are easier to move when overlap of wave functions is larger. In the present invention, it is presumed that because the light-emitting layer(s) contain different three types of the non-light-emitting organic materials, packing density of each amorphous film is increased, and thus intermolecular distances are shortened and effects from anisotropy of molecules are reduced, which increases overlap of wave functions and results in improvement in electrical properties.

In addition, the organic EL element of the present invention achieves longer lifetime by virtue of improvement, in efficiency. The reason is presumably that because the light-emitting layer(s) (note that the present invention includes the both cases where a single light-emitting layer is provided or multiple light-emitting layers are provided) contain three or more types of the non-light-emitting organic materials represented by the general formula (2), growth of crystals is suppressed and storage stability in high temperature is improved.

In Non-Patent Document 2, efficiency is improved by adding a third type of a host; but this improvement is achieved presumably by virtue of effects for confining excitons because triplet energy level of the added third type of a host is larger than that of a dopant.

In contrast, the configuration of the present invention (i.e., the configuration that the light-emitting layer(s) contain at least three types of the non-light-emitting organic materials represented by the general formula (2)) achieves improvement in electrical properties by increasing packing, density of the light-emitting layers). Thus, the effect of the present invention is different than that of Non-Patent Document 2. Further, the present invention also achieves high storage stability in high temperature.

The contents (% by mass) of the non-light-emitting organic materials in the light-emitting layer(s) are not particularly limited. Describing each of the non-light-emitting organic material as Fin wherein n corresponds to order of magnitude of the contents (% by mass) (a smaller n represents a larger content), preferable ranges of the contents are 50% by mass$\leq H1 \leq$98% by mass, 1% by mass$\leq H2 \leq$49% by mass, 1% by mass$\leq H3 \leq$33.3% by mass, 1% by mass$\leq H3 \leq$25% by mass and 1% by mass$\leq H5 \leq$20% by mass, preferably 50% by mass$\leq H1 \leq$97% by mass, 1% by mass$\leq H2 \leq$48% by mass, 1% by mass$\leq H3 \leq$32.3% by mass, 1% by mass$\leq H4 \leq$25% by mass and 1% by mass$\leq H5 \leq$20% by mass, more preferably 50% by mass$\leq H1 \leq$96% by mass, 1% by mass$\leq H2 \leq$47% by mass, 1% by mass$\leq H3 \leq$31.3% by mass, 1% by mass$\leq H4 \leq$24% by mass and 1% by mass$\leq H5 \leq$20% by mass, and further more preferably 70% by mass$\leq H1 \leq$96% by mass, 1% by mass$\leq H2 \leq$30% by mass, 1% by mass$\leq H3 \leq$15% by mass, 1% by mass$\leq H4 \leq$10% by mass and 1% by mass$\leq H5 \leq$5% by mass.

Describing each of the non-light-emitting organic materials as Hn wherein n corresponds to order of magnitude of the contents (% by mass) (a smaller n represents a larger content), the molecular weight of Hn, $M_{Hn}$, preferably decreases with the increase of n, namely, $M_{H1} > M_{H2} > M_{H3} \ldots$.

That is, the light-emitting layer is mainly composed of the non-light-emitting organic material having a large molecular weight in a large content (% by mass); if the light-emitting layer consists of only such a non-light-emitting organic material, however, packing is difficult and packing density is small, and thus, molecules having small molecular weights are packed in the light-emitting layer to increase packing density.

When a difference between the largest molecular weight among molecular weight of the non-light-emitting organic materials, $M_{max}$, and the smallest molecular weight among molecular weights of the non-light-emitting organic materials, $M_{min}$, i.e., $M_{max}$ minus $M_{min}$ is less than 250, storage stability in high temperature is further improved.

The non-light-emitting organic material represented by the general formula (2) preferably includes a structure that is easy to cause carrier movement through pi interactions. Further, at least three types of the non-light-emitting organic materials represented by the general formula (2) preferably include the same type of an aromatic structure (specifically, include an aromatic hydrocarbon ring or aromatic hetero ring).

In the present invention, it is preferable that the total contents of an aromatic ring structure(s) (aromatic ring(s)) with respect to the total weight of the non-light-emitting organic material(s) used in the light-emitting layer(s) is 60% or more, and more preferably 80% or more The non-light-emitting organic material represented by the general formula (2) may be suitably used as a host compound of the present invention. Details of the host compound will be described later.

A structure of the non-light-emitting organic material represented by the general formula (2) will be described.

In the general formula (2), X represents NR', O, S, PR', R'R''', CR'R'' or SiR'R''.

As for X in the general formula (2), examples of R', R'' and R''' include alkyl groups (such as a methyl group, ethyl group, propyl group, isopropyl group, t-butyl group, pentyl group, hexyl group, octyl group, dodecyl group, tridecyl group, tetradecyl group, pentadecyl group) cycloalkyl groups (such as a cyclopentyl group and cyclohexyl group), alkenyl groups such as a vinyl group and allyl group), alkynyl groups (such as an ethynyl group and propargyl group), aromatic hydrocarbon rings (also referred to as aromatic carbon rings or allyl groups, such as a phenyl group, chlorophenyl group, mesityl group, tolyl group, xylyl group, naphthyl group, anthryl group, azulenyl group, acenaphthenyl group, fluorenyl group, phenanthryl group, indenyl group, pyrenyl group, biphenyl group), aromatic hetero rings (such as pyridyl group, pyrimidinyl group, furyl group, pyrrolyl group, thienyl group, imidazolyl group, benzoimidazolyl group, pyrazolyl group, pyrazinyl group, triazolyl group (exemplified by a 1,2,4-triazole-1-yl group and 1,2,3-triazole-1-yl group), oxazolyl group, benzoxazolyl group, thiazolyl group, isoxazolyl group, isothiazolyl group, furazanyl group, thienyl group, guinolyl group, benzofuryl group, dibenzofuryl group, benzothienyl group, dibenzothienyl group, indolyl group, carbazolyl group, carbolinyl group, diazacarbazolyl group (a group where one carbon atom on the carboline ring of the carbolinyl group is substituted with a nitrogen atom), uinoxalinyl group, pyridazinyl group, triazinyl group, quinazolinyl group, phthalazinyl group), hetero rings (such as a pyrrolidyl group, imidazolidyl group, morpholyl group and oxazolidyl group), alkoxy groups (such as a methoxy group, ethoxy group, propyloxy group, pentyloxy group, hexyloxy group, octyloxy group and dodecyloxy group), cycloalkoxy groups (such as cyclopentyloxy group and cyclohexyloxy group), allyloxy groups (such as a phenoxy group and naphthyloxy group), alkylthio groups (such as a methylthio group, ethylthio group, propylthio group, pentylthio group, hexylthio group, octylthio group and dodedcylthio group), cycloalkylthio groups (such as a cyclopentylthio group and cyclohexylthio group), allylthio groups (such as a phenylthio group and naphthylthio group), alkoxycarbonyl groups (such as a methyloxycarbonyl group, ethyloxycarbonyl group, butyloxycarbonyl group, octyloxycarbonyl group and dodecyloxycarbonyl group), allyloxycarbonyl groups (such as a phenyloxycarbonyl group and naphthyloxycarbonyl group), sulfamoyl groups (such as an aminosulfonyl group, methylaminosulfonyl group, dimethylaminosulfonyl group, butylaminosulfonyl group, hexylaminosulfonyl group, cyclohexylaminosulfonyl group, octylaminosulfonyl group, dodecylaminosulfonyl group, phenylaminosulfonyl group, naphthylaminosulfonyl group and 2-pyridylaminosulfonyl group), acyl groups (such as an acetyl group, ethylcarbonyl group, propylcarbonyl group, pentylcarbonyl group, cyclohexylcarbonyl group, octylcarbonyl group, 2-ethylhexylcarbonyl group, dodecylcarbonyl group, phenylcarbonyl group, naphthylcarbonyl group and pyridylcarbonyl group), acyloxy groups (such as an acetyloxy group, ethylcarbonyloxy group, butylcarbonyloxy group, octylcarbonyloxy group, dodecylcarbonyloxy group and phenylcarbonyloxy group), amide groups (such as a methylcarbonylamino group, ethylcarbonylamino group, dimethylcarbonylamino group, propylcarbonylamino group, pentylcarbonylamino group, cyclohexylcarbonylamino group, 2-ethyhexylcarbonylamino group, octylcarbonylamino group, dodecylcarbonylamino group, phenylcarbonylamino group and naphthylcarbonylamino group), carbamoyl groups (such as aminocarbonyl group, methylaminocarbonyl group, dimethylaminocarbonyl group, propylaminocarbonyl group, pentylaminocarbonyl group, cyclohexylaminocarbonyl group, octylaminocarbonyl group, 2-ethylhexylaminocarbonyl group, dodecylaminocarbonyl group, phenylaminocarbonyl group, naphthylaminocarbonyl group and 2-pyridylaminocarbonyl group), ureido groups (such as a methylureido group, ethylureido group, pentylureido group, cyclohexylureido group, octylureido group, docylureido group, phenylureido group, naphthylureido group and 2-pyridylaminoureido group), sulfinyl groups (such as a methylsulfinyl group, ethylsulfinyl group, butylsulfinyl group, cyclohexylsulfinyl group, 2-ethylhexylsulfinyl group, dodecylsulfinyl group, phenylsulfinyl group, naphtylsulfinyl group and 2-pyridylsulfinyl group), alkylsulfonyl groups (such as a methylsulfonyl group, ethylsulfonyl group, butylsulfonyl group, cyclohexylsulfonyl group, 2-ethylhexylsulfonyl group and dodecylsulfonyl group), allylsulfonyl or heteroallylsulfonyl groups (such as a phenylsulfonyl group, naphthylsulfonyl group and 2-pyridylsulfonyl group), amino groups (such as an amino group, ethyl amino group, dimethyl amino group, butylamino group, cyclopentylamino group, 2-ethylhexylamino group, dodecylamino group, anilino group, naphthylamino group and 2-pyridylamino group), halogen atoms (such as a fluorine atom, chlorine atom and bromine atom), fluorohydrocarbon groups (such as a fluoromethyl group, trifluoromethyl group, pentafluoroethyl group and pentafluorophenyl group), a cyano group, a nitro group, a hydroxy group, a mercapto group, silyl groups (such as a trimethylsilyl group, triisopropylsilyl group, triphenylsilyl group and phenyldiethylsilyl group)

The above substituents may be substituted with the above substituent(s), and may be bonded with each other to form a ring.

X is preferably $NR_2$ or O. Particularly preferable examples of $R_2$ are aromatic hydrocarbon rings (also referred to as aromatic carbon rings or allyl groups, such as a phenyl group, p-chlorophenyl group, mesityl group, tolyl group, xylyl group, naphthyl group, anthryl group, azulenyl group, acenaphthenyl group, fluorenyl group, phenanthryl group, indenyl group, pyrenyl group and biphenylyl group), or aromatic hetero rings (such as a furyl group, thienyl group, pyridyl group, pyridazinyl group, pyrimidinyl group, pyrazinyl group, triazinyl group, imidazolyl group, pyrazolyl group, thiazolyl group, quinazolyl group, phthalazinyl group and dibenzofuranyl group).

The above described aromatic hydrocarbon rings or aromatic hetero rings may be substituted with a substituent(s) corresponding to a substituent represented by R' R" or R'" of X in the general formula (2)

In the general formula (2), Ar represents an aromatic hydrocarbon ring or aromatic hetero ring.

Examples of the aromatic hydrocarbon ring represented by Ar include groups derived form a benzene ring, biphenyl ring, naphthalene ring, azulene ring, anthracene ring, phenanthrene ring, pyrene ring, chrysene ring, naphthacene ring, triphenylene ring, o-terphenyl ring, m-terphenyl ring, p-terphenyl ring, acenaphthene ring, coronene ring, fluorene ring, fluoranthrene ring, naphthacene ring, pentacene ring, perylene ring, pentaphene ring, picene ring, pyrene ring, pyranthrene ring, anthranthrene ring and/or the like.

Among the above, preferable examples of the aromatic hydrocarbon ring represented by Ar in the general formula (2) are groups derived from a benzene ring, more preferable examples are groups derived from a benzene ring including a substituent(s) and particularly preferable examples are groups derived from a benzene ring including a carbazolyl group(s).

The aromatic hydrocarbon ring represented by Ar in the general formula (2) may be groups derived from a fused ring(s) composed of three or more rings as preferable examples. The groups derived from a used ring(s) composed of three or more rings are exemplified by groups derived from a naphthacene ring, anthracene ring, tetracene ring, pentacene ring, hexacene ring, phenanthrene ring, pyrene ring, benzopyrene ring, benzoazulene ring, chrysene ring, benzochrysene ring, acenaphthene ring, acenaphthylene ring, triphenylene ring, coronene ring, benzocoronene ring, hexabenzocoronene ring, fluorene ring, benzofluorene ring, fluoranthene ring, perylene ring, naphthoperylene ring, pentabenzoperylene ring, benzoperylene ring, pentaphene ring, picene ring, pyranthrene ring, coronene ring, naphthocoronene ring, ovalene ring anthranthrene ring and/or the like.

The above rings may include a substituent(s) corresponding to a substituent represented by R', R" or R'" of X in the general formula (2).

Examples of the aromatic hetero ring represented by Ar include groups derived from a furan ring, dibenzofuran ring, thiophene ring, oxazole ring, pyrrole ring, pyridine ring, pyridazine ring, pyrimidine ring, pyridine ring, triazine ring, benzoimidazole ring, oxadiazole ring, triazole ring, imidazole ring, pyrazole ring, thiazole ring, indole ring, indazole ring, benzoimidazole ring, benzothiazole ring, benzoxazole ring, quinoxaline ring, quinazoline ring, cinnoline ring, quinoline ring, isoquinoline ring, phthalazine ring, naphthidine ring, carbazole ring, carboline ring and/or diazacarbazole ring is ring where one carbon atom of a hydrocarbon ring constituting a carboline ring is substituted with a nitrogen atom).

The aromatic hetero ring represented by Ar in the general formula (2) may be groups derived from a fused ring(s) composed of three or more rings as preferable examples. Specific examples of the groups derived from a fused ring(s) composed of three or more rings include groups derived from an acridine ring, benzoquinoline ring, carbazole ring, carboline ring, phenazine ring, phenanthridine ring, phenanthroline ring, carboline ring, cyclazine ring, quindoline ring, tepenijine ring, quinindoline ring, triphenodithiazine ring, triphenodioxazine ring, phenanthridine, ring, anthrazine ring, perimidine ring, diazacarbazole ring (a ring where one carbon atom of a hydrocarbon ring constituting a carboline ring is substituted with a nitrogen atom), phenanthroline ring, dibenzofuran ring, dibenzothiophene ring, naphthofuran ring, naphthothiophene ring, benzodifuran ring, benzothiophene ring, naphthodifuran ring, naphthodithiophene ring, anthrafuran ring, anthradifuran ring, anthrathiophene ring, anthradithiophene ring, thianthrene ring, phenoxathiin ring and thiophanthrene ring (naphthothiophene ring) and/or the like.

Among the above, preferable examples of the aromatic hetero ring represented by Ar in the general formula (2) are groups derived from a carbazole ring, carboline ring or dibenzofuran ring, more preferable examples are groups derived from a carbazole ring or carboline ring, and particularly preferable examples are groups derived from a benzene ring including a carbazolyl group(s).

These rings may include a substituent(s) corresponding to a substituent represented by R', R" or R'" in the general formula (2)

In the general formula (2), n represents an integer from 0 to 8, preferably from 0 to 2, and particularly in the case where X is O or S, preferably 1 or 2.

(Compound Represented by General Formula (3))

A compound represented by the general formula (2) is more preferably a compound represented by the general formula (3).

In the general formula (3), X, Y and Z each represent NR', O, S, PR', PR', PR'R"R'", CR'R" SiR'R", wherein a substituent represented by R', R" or R'" corresponds to a substituent represented by R' R" or R'" of X in the general formula (2). The three fused rings in the general formula (3) are directly bonded to each other at arbitrary positions. The benzene ring may include a substituent(s).

The non-light-emitting organic material of the present invention is preferably a compound represented by the general formula (2) or (3). The compound represented by the general formula (2) or (3) is suitably used as a host compound in the light-emitting layer of the organic EL element of the present invention. Particularly, the host compound preferably include both of a dibenzofuran ring and carbazole ring.

Specific examples of the host compound represented by the general formula (2) (a-1 to a-41) are shown below, but not limited thereto. Among the exemplary compounds shown below, compounds represented by a-1, 2, 3, 5, 6, 11, 13, 20, 27, 29, 35, 36, 39 and 41 are compounds represented by the general formula (3).

[Chemical formula 4]
a-1
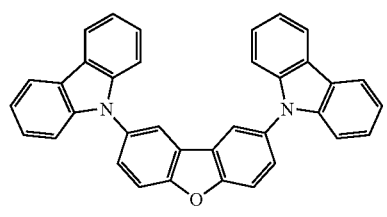
a-2
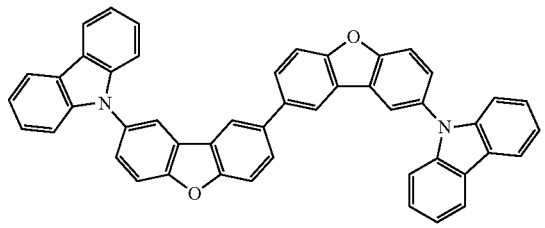
a-3
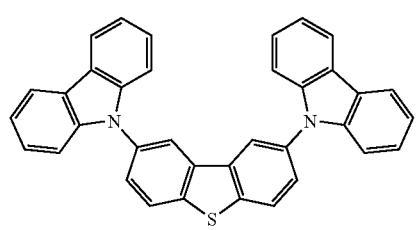
a-4
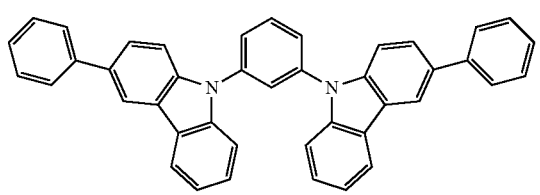
a-5
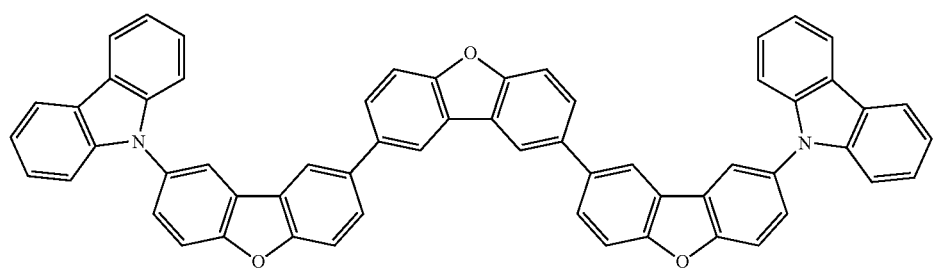
a-6
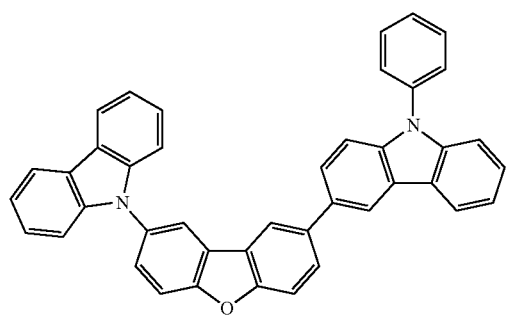
[Chemical formula 5]
a-7
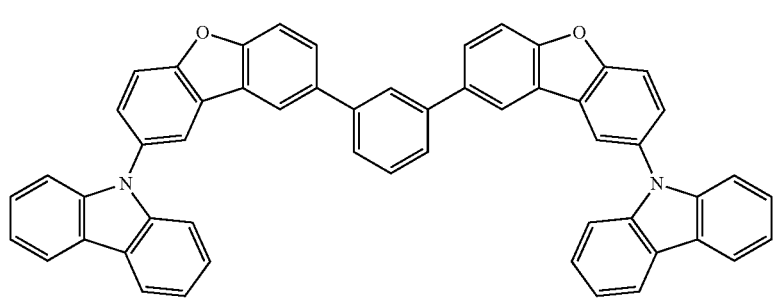

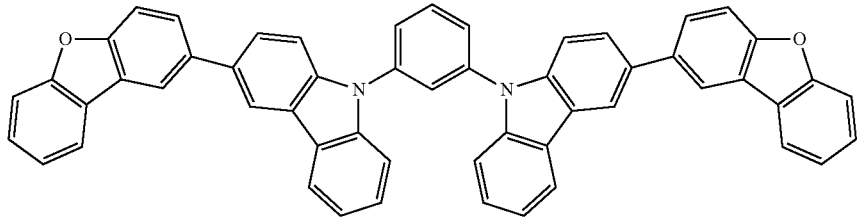
a-8
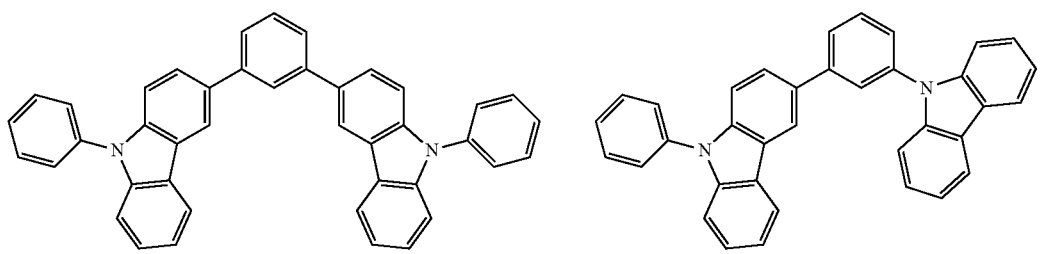
a-9 a-10
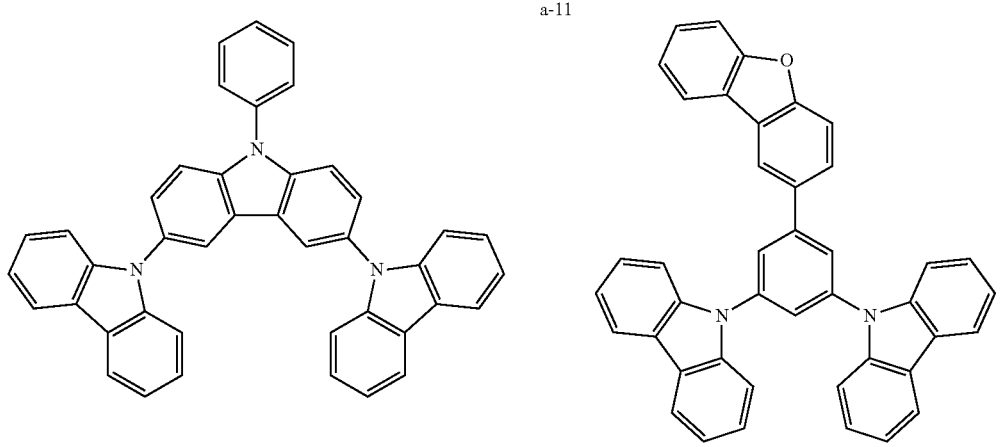
a-11 a-12
[Chemical formula 6]
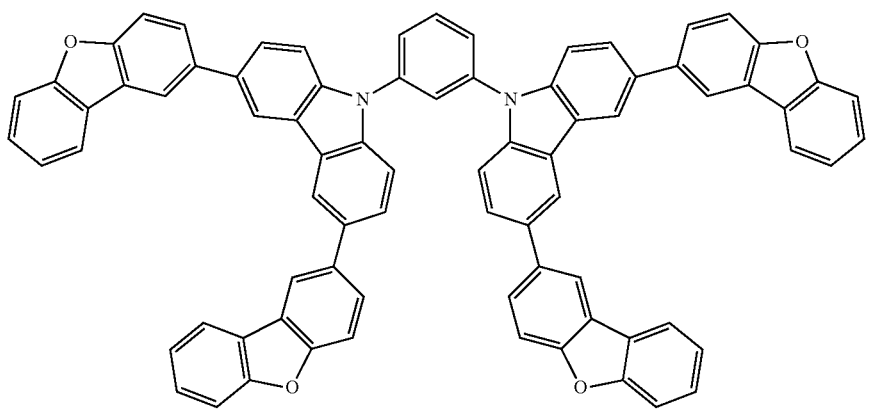
a-13

-continued
a-14
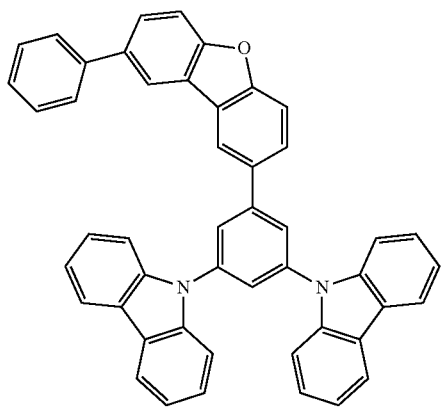
a-15
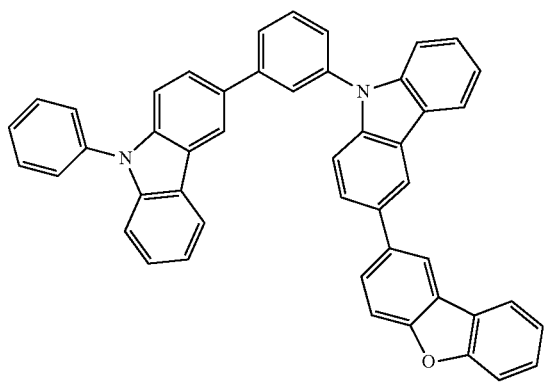
a-16
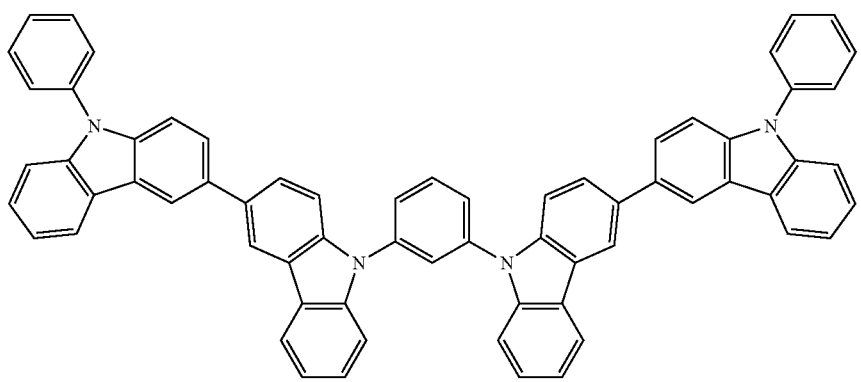
a-17
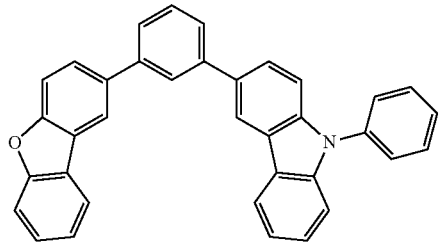
a-18
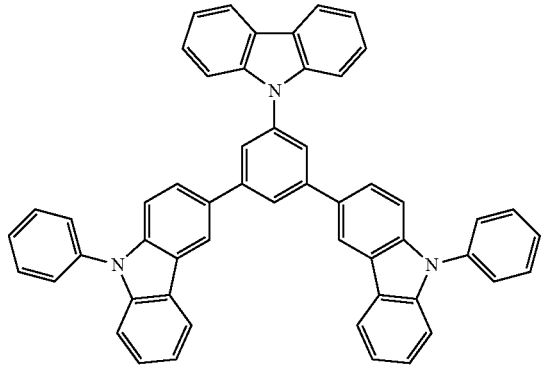
[Chemical formula 7]
a-19
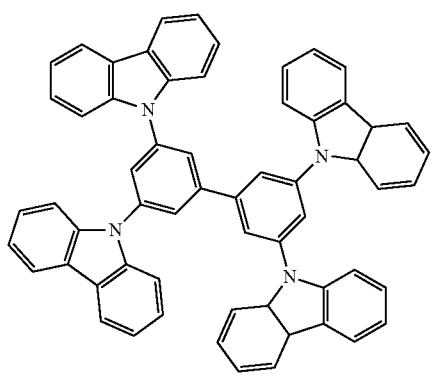
a-20
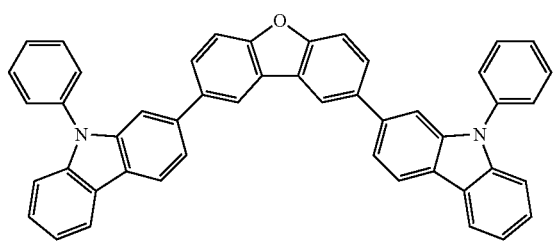

-continued
a-21
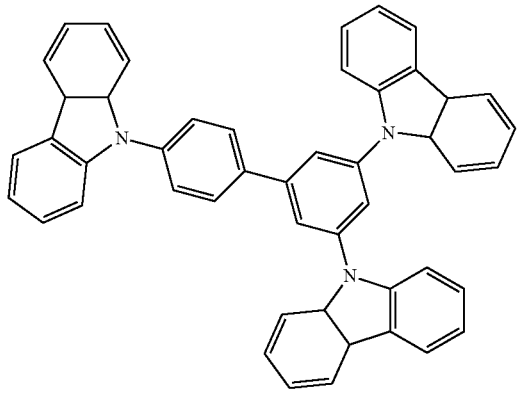
a-22
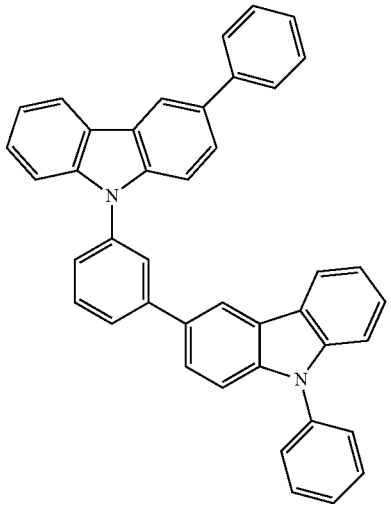
a-23
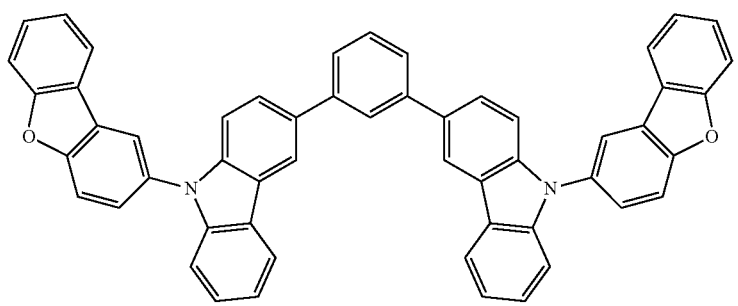
a-24
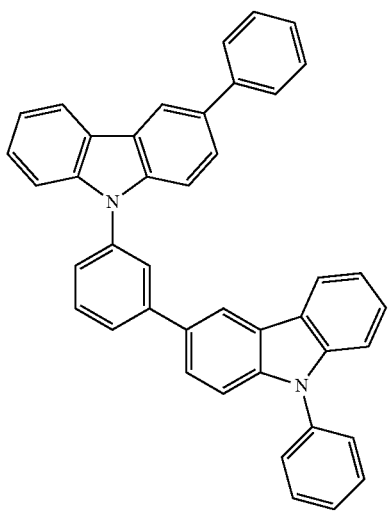

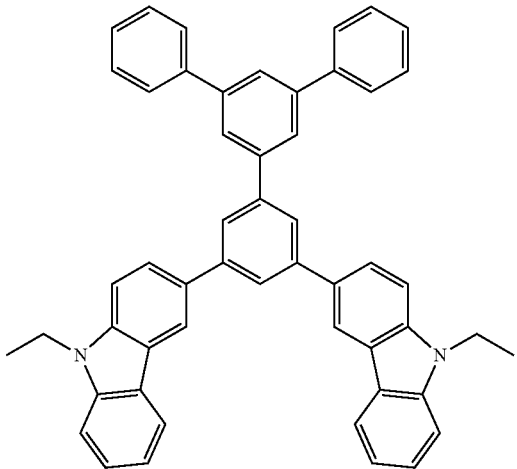
a-25
[Chemical formula 8]
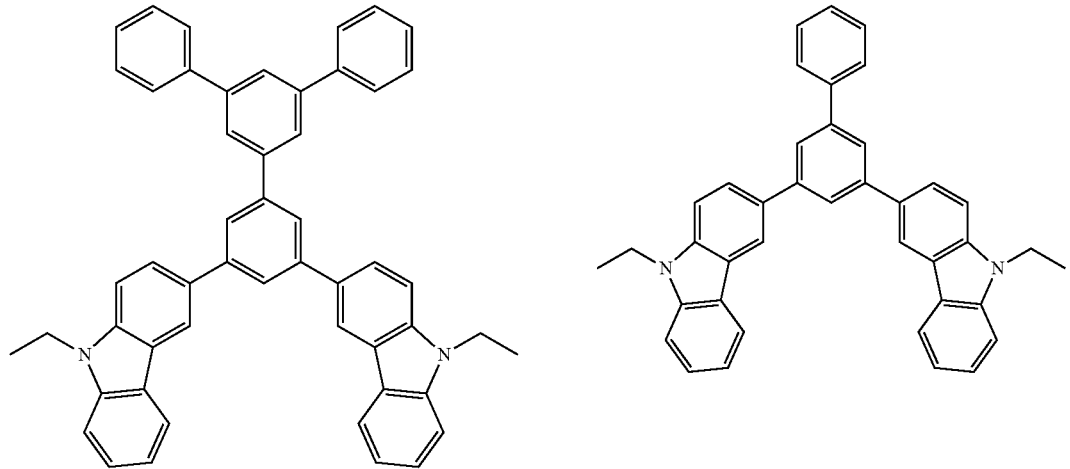
a-25
a-26
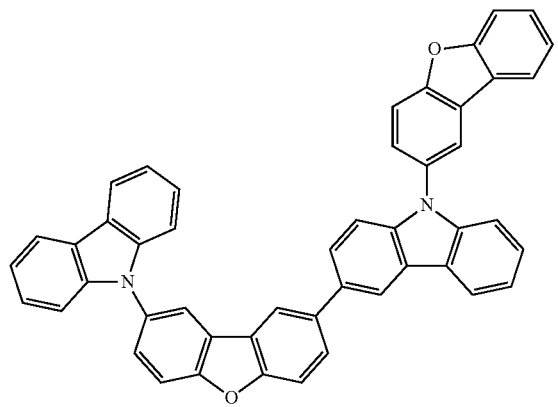
a-27

-continued
a-28
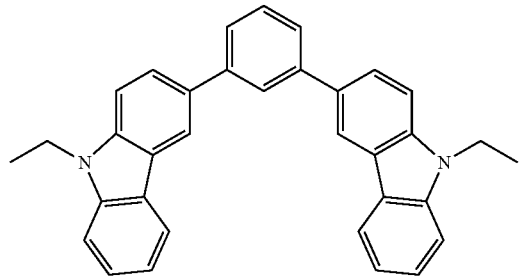
a-29
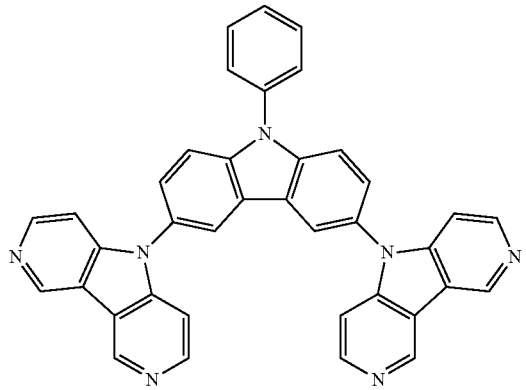
[Chemical formula 9]
a-30
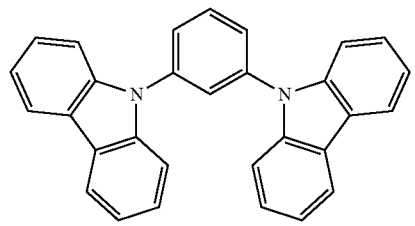
a-31
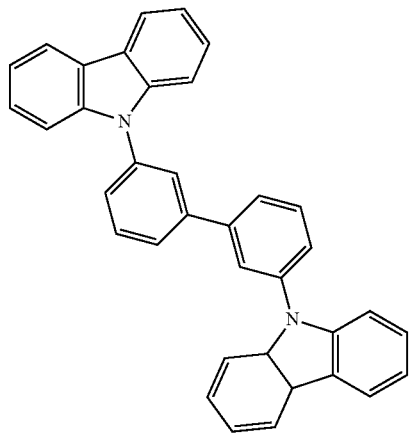
a-32
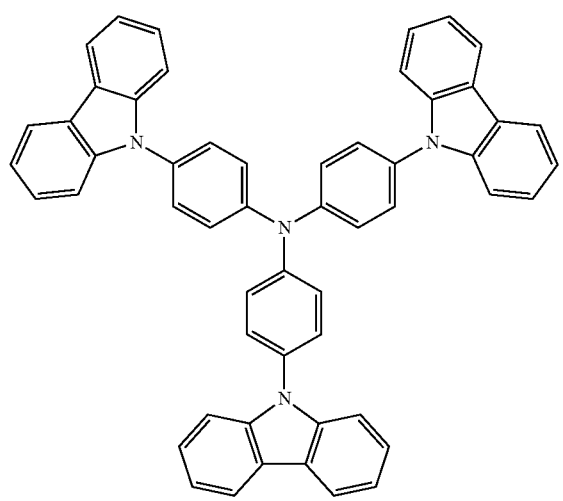
a-33
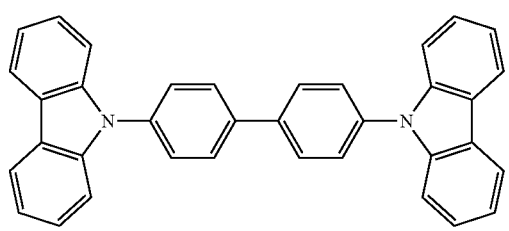
a-34
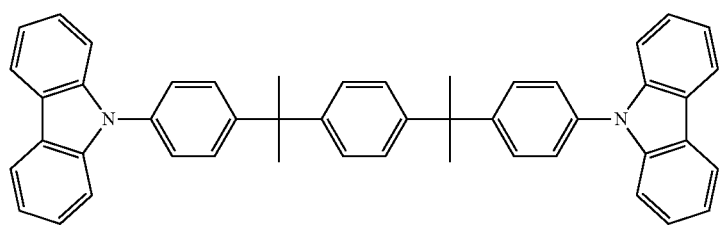

[Chemical formula 10]
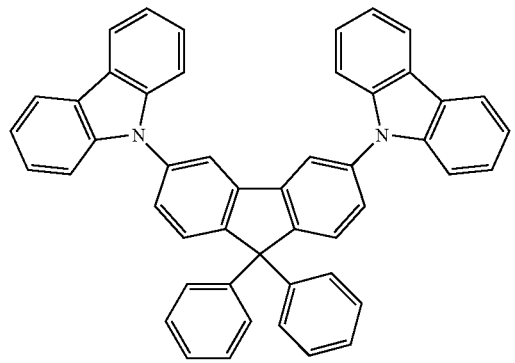
a-35
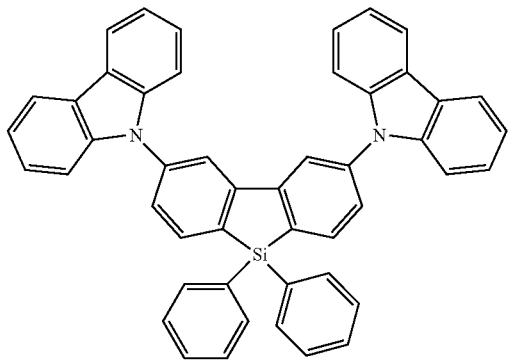
a-36
[Chemical formula 11]
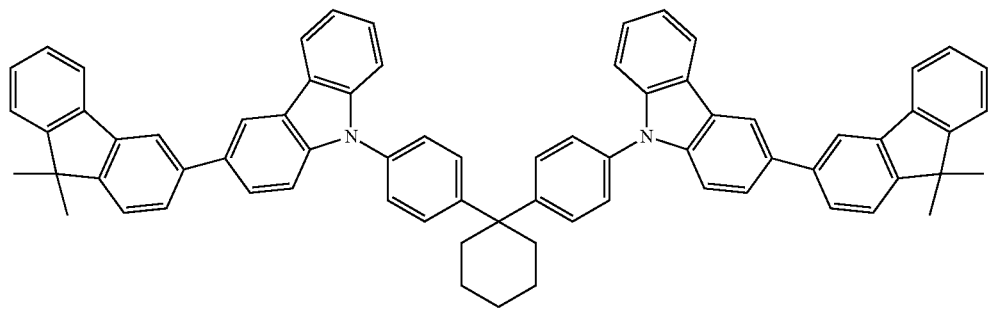
a-37
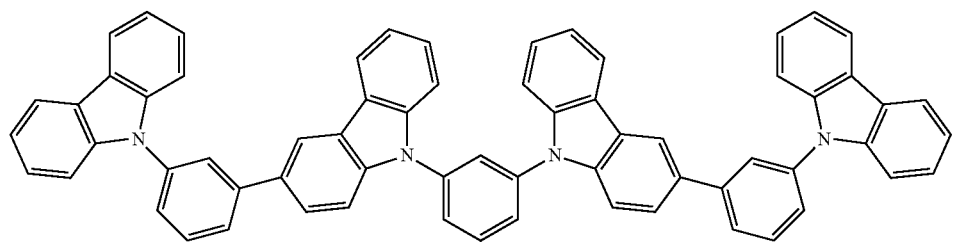
a-38
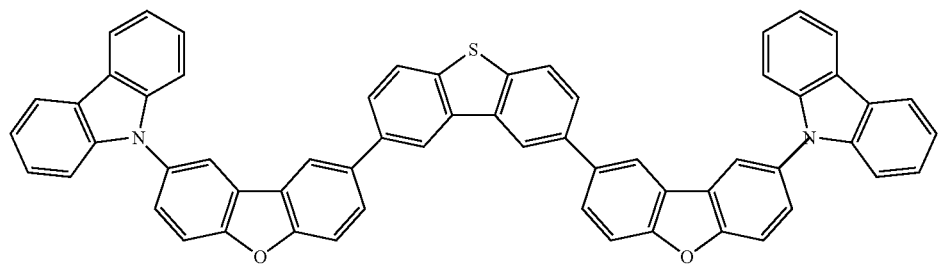
a-39

-continued a-40

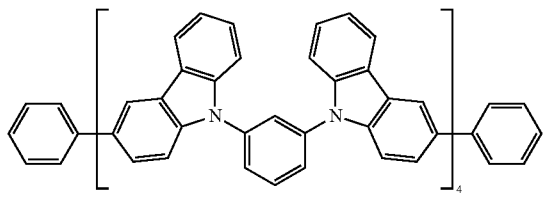

a-41

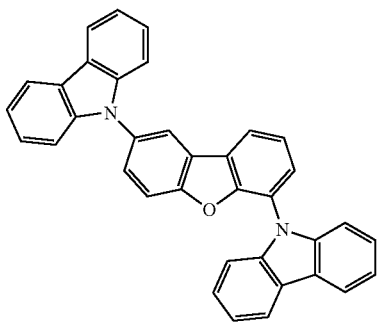

<<Host Compound>>

A host compound used in the organic EL element of the present invention will be described.

The host compound contained in the light-emitting layer of the organic EL element of the present invention preferably has a phosphorescence quantum yield in phosphorescence emission at room temperature (25° C.) of less than 0.1, and more preferably less than 0.01.

In the present invention, the host compound is preferably a compound represented by the general formula (2) or (3) used as the non-light-emitting organic material of the present invention.

Along with the compound(s) represented by the general formula (2) or (3), a conventionally known host compound (s) may be used as the non-light-emitting organic material or the host compound. One or more types of conventionally known host compounds may be used.

When multiple types of light-emitting materials described later are used light of different colors can be mixed, and thus cry desired light color can be obtained.

Preferably, the known host compound has electron hole-transporting properties and electron-transporting properties, prevents light wavelength from being lengthened, and has high Tg (glass transition temperature).

Grass transition temperature (Tg) is obtained by a method according to JIS-K-7121 using a. DSC (Differential Scanning Colorimetry).

Specific examples of the known host compound include compounds described in, for example, Japanese Patent Application Laid-open Publications Nos. 2001-257076, 2002-308855, 2001-313179, 2002-319491, 2001-357977, 2002-334786, 2002-8860, 2002-334787, 2002-15671, 2002-334788, 2002-43056, 2002-334789, 2002-75645, 2002-338579, 2002-105445, 2002-343568, 2002-141173, 2002-352957, 2002-203683, 2002-363227, 2002-231453, 2003-3165, 2002-234888, 2003-27048, 2002-255934, 2002-260861, 2002-280183, 2002-299060, 2002-302516, 2002-305083, 2002-305084 and 2002-308837.

The host compound used in the present invention is preferably a carbazole derivative.

The above-described known host compound may be used as the non-light-emitting organic material of the present invention.

<<Light Emitting Dopant (Light-Emitting Dopant Compound)>>

The light-emitting dopant of the present invention will be described.

As the light-emitting material (light-emitting dopant) of the present invention, at least one type of a phosphorescence-emitting dopant (also referred to as phosphorescent compound, phosphorescence-emitting compound or the like) is used.

In the present invention, the phosphorescence-emitting dopant is a compound that shows light emission from an excited triplet, specifically is a compound that emits phosphorescence at room temperature (25° C.), and has a phosphorescence quantum yield at 25° C. of 0.01 or more, and more preferably 0.1 or more.

The above-mentioned phosphorescence quantum yield may be obtained by a method described in page 398 of Spectroscopy II of The 4th Series of Experimental Chemistry 7 (1992, published by Maruzen Co., Ltd.). Phosphorescence quantum yield in a solution may be measured using various solvents; the phosphorescence-emitting material of the present invention may be any compound having the above phosphorescence quantum yield (0.01 or more)

There are two principles of light emission by a phosphorescence-emitting compound. One is an energy transfer-type, wherein the recombination of carriers occurs on a host compound onto which the carriers are transferred to produce an excited state of the host compound, and then via transfer of this energy to a phosphorescence-emitting compound, light emission from the phosphorescence-emitting compound occurs. The other is a carrier trap-type, wherein a phosphorescence-emitting compound serves as a carrier trap to cause recombination of carriers on the phosphorescence-emitting compound, and thereby light emission from the phosphorescence-emitting compound occurs in each type, the energy in the excited state of the phosphorescence-emitting compound is required to be lower than that in the excited state of the host compound.

The phosphorescence-emitting dopant may be a compound selected from known compounds that have been used in a light-emitting layer of an organic EL element as needed, and is preferably a complex compound containing a metal of Groups 8 to 10 on the periodic table, more preferably an iridium compound, an osmium compound, a platinum compound (platinum complex type compound) or a rare earth complex, and most preferably an iridium compound. More specifically, a phosphorescence-emitting dopant represented by the general formula (1) is preferably used.

(Phosphorescence-Emitting Dopant Represented by General Formula (1))

Examples of a substituent represented by $R_1$ in the general formula (1) include alkyl groups (such as a methyl group, ethyl group, propyl group, isopropyl group, tort-butyl, group, pentyl group, hexyl group, cetyl group, dodecyl group, tridecyl group, tetradecyl group, pentadecyl group), cycloalkyl groups (such as a cyclopentyl group and cyclohexyl group), alkenyl groups (such as a vinyl group and allyl group), alkynyl groups (such as an ethynyl group and propargyl group), aromatic hydrocarbon rings (also referred to as aromatic carbon rings or allyl groups, such as a phenyl group, p-chlorophenyl group, mesityl group, tolyl group, xylyl group, naphthyl group, anthryl group, azulenyl group, acenaphthenyl group, fluorenyl group, phenanthryl group, indenyl group, pyrenyl group, biphenyl group), aromatic hetero rings (such as pyridyl group, pyrimidinyl group, furyl group, pyrrolyl group, thienyl group, imidazolyl group, benzoimidazolyl group, pyrazolyl group, pyrazinyl group, triazolyl group (exemplified by 1,2,4-triazole-1-yl group and 1,2,3-triazole-1-yl group), oxazolyl group, benzaxazolyl group, thiazolyl group, isoxazolyl group, isothiazolyl group, furazanyl group, thienyl group, quinolyl group, benzofuryl group, dibenzofuryl group, benzothienyl group, dibenzothienyl group, indolyl group, carbazolyl group, carbolinyl group, diazacarbazolyl group (a group where one carbon atom on the carboline ring of the carbolinyl group is substituted with a nitrogen atom), quinoxalinyl group, pyridazinyl group, triazinyl group, quinazolinyl group, phthalazinyl group), hetero rings (such as pyrrolidyl group, imidazolidyl group, morpholyl group and oxazolidyl group), alkoxy groups (such as a methoxy group, ethoxy group, propyloxy group, pentyloxy group, hexyloxy group, octyloxy group and dodecyloxy group), cycloalkoxy groups (such as cyclopentyloxy group and cyclohexyloxy group) allyloxy groups (such as a phenoxy group and naphthyloxy group), alkylthio groups (such as a methylthio group, ethylthio group, propylthio group, pentylthio group, hexylthio group, octylthio group and dodedcylthio group), cycioalkylthio groups (such as cyclopentylthio group and cyclohexylthio group), allylthio groups (such as a phenylthio group and naphthylthio group), alkoxycarbonyl groups (such as a methyloxycarbonyl group, ethyloxycarbonyl group, butyloxycarbonyl group, octyloxycarbonyl group and dodecyloxycarbonyl group), allyloxycarbonyl groups (such as a phenyloxycarbonyl group and naphthyloxycarbonyl group), sulfamoyl groups (such as an aminosulfonyl group, methylaminosulfonyl group, dimethylaminosulfonyl group, butylaminosulfonyl group, hexylaminosulfonyl group, cyclohexylaminosulfonyl group, octylaminosulfonyl group, dodecylaminosulfonyl group, phenylaminosulfonyl group, naphthylaminosulfonyl group and 2-pyridylaminosulfonyl group), acyl groups (such as an acetyl group, ethylcarbonyl group, propylcarbonyl group, pentylcarbonyl group, cyclohexylcarbonyl group, octylcarbonyl group, 2-ethylhexylcarbonyl group, dodecylcarbonyl group, phenylcarbonyl group, naphthylcarbonyl group and pyridylcarbonyl group), acyloxy groups (such as an acetyloxy group, ethylcarbonyloxy group, butylcarbonyloxy group, octylcarbonyloxy group, dodecylcarbonyloxy group and phenylcarbonyloxy group), amide groups (such as a methylcarbonylamino group, ethylcarbonylamino group, dimethylcarbonylamino group, propylcarbonylamino group, pentylcarbonylamino group, cyclohexylcarbonylamino group, 2-ethyhexylcarbonylamino group, octylcarbonylamino group, dodecylcarnobylamino group, phenylcarbonylamino group and naphthylcarbonylamino group), carbamoyl groups (such as aminocarbonyl group, methylaminocarbonyl group, dimethylaminocarbonyl group, propylaminocarbonyl group, pentylaminocarbonyl group, cyclohexylcarbonylamino group, octylaminocarbonyl group, 2-ethylhexylaminocarbonyl group, dodecylaminocarbonyl group, phenylaminocarbonyl group, naphthylaminocarbonyl group and 2-Pyridylaminocarbonyl group) ureido groups (such as a methylureido group, ethylureido group, pentylureido group, cyclohexylureido group, octylureido group, docylureido group, phenylureido group, naphthylureido group and 2-pyridylaminoureido group), sulfinyl groups (such as a methylsulfinyl group, ethylsulfinyl group, butylsulfinyl group, cyclohexylsulfinyl group, 2-ethylhexylsulfinyl group, dodecylsulfinyl group, phenylsulfinyl group, naphtylsulfinyl group and 2-pyridylsulfinyl group), alkylsulfonyl groups (such as a methylsulfonyl group, ethylsulfonyl group, butylsulfonyl group, cyclohexylsulfonyl group, 2-ethylhexylsulfonyl group and dodecylsulfonyl group), allylsulfonyl or heteroallylsulfonyl groups (such as a phenylsulfonyl group, naphthylsulfonyl group and 2-pyridylsulfonyl group), amino groups (such as an amino group, ethyl amino group, dimethylamino group, butylamino group, cyclopentylamino group, 2-ethylhexylamino group, dodecylamino group, anilino group, naphthylamino group and 2-pyridylamino group), halogen atoms (such as a fluorine atom, chlorine atom and bromine atom), fluorohydrocarbon groups (such as a fluoromethyl group, trifluoromethyl group, pentafluoroethyl group and pentafluorophenyl group), a cyano group, a nitro group, a hydroxy group, a mercapto group, silyl groups (such as a trimethylsilyl group, triisopropylsilyl group, triphenylsilyl group and phenyldiethylsilyl group). Among these substituents, alkyl groups and allyl groups are preferable In the general formula (1), examples of a five to seven-membered ring formed with Z include a benzene ring, naphthalene ring, pyridine ring, pyrimidine ring, pyrrole ring, thiophene ring, pyrazole ring, imidazole ring, oxazole ring and thiazole ring. Among them, a benzene ring is preferable.

In the general formula (1), an aromatic hetero ring formed with $B_1$ to $B_5$ is preferably monocyclic. Examples of the aromatic hetero ring include a pyrrole ring, pyrazole ring, imidazole ring, triazole ring, tetrazole ring, oxazole ring, isoxazole ring, thiazole ring, isothiazole ring, oxadiazole ring and thiadiazole ring.

Among them, a pyrazole ring and imidazole ring are preferable, and an imidazole ring where $B_2$ and $B_5$ are nitrogen atoms is particularly preferable.

The above-described rings in the general formula (1) may be substituted with a substituent(s) represented by R1 of the general formula (1). A substituent is preferably an alkyl group or allyl group, and more preferably an allyl group.

In the general formula (1), L represents a group of atoms forming a bidentate ligand together with $X_1$ and $X_2$. Specific examples of the bidentate ligand represented by $X_1$-$L_1$-$X_2$ include phenylpyridine, phenylpyrazole, phenylimidazole, phenyltriazole, phenyltetrazole, pyrazabole, picolinic acid and acetyl acetone.

These groups may be substituted with a substituent(s) represented by $R_1$ in the general formula (1).

In the general formula (1), $m_1$ represents an integer 1, 2 or 3, $m_2$ represents an integer 0, 1 or 2, wherein $m_1+m_2$ is to 2 or 3. Particularly, $m_2$ is preferably 0.

In the general formula (1), a transition metal represented by $M_1$ is a transition metal of Group 8 to 10 on the periodic table of the elements (also simply referred to as a transition metal), preferably iridium or platinum, and more preferably iridium.

Specific examples of the phosphorescence-emitting dopant (phosphorescence-emitting compound) represented by the general formula (1) are shown below, but not limited thereto.

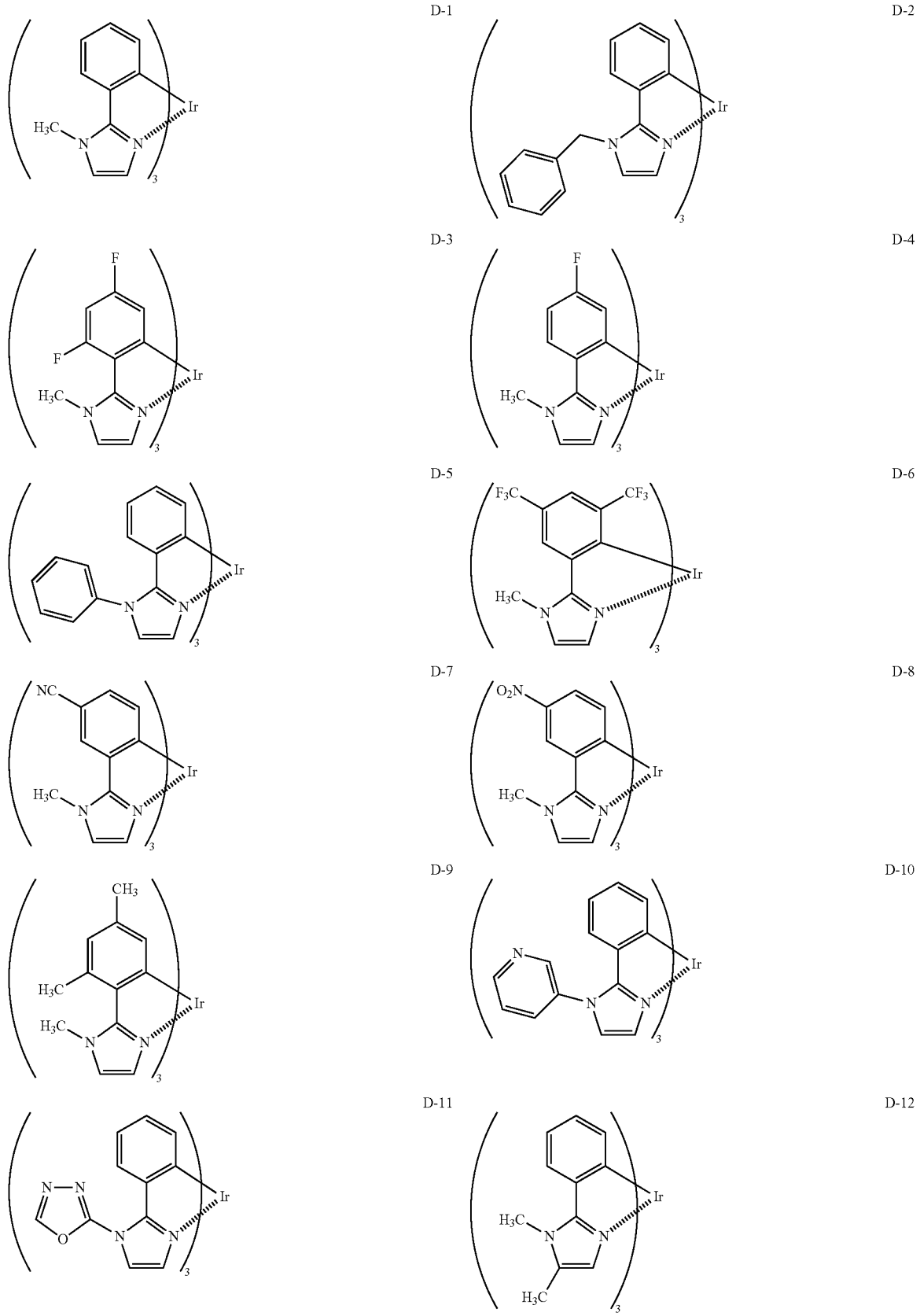

-continued
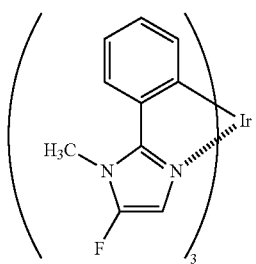
D-13
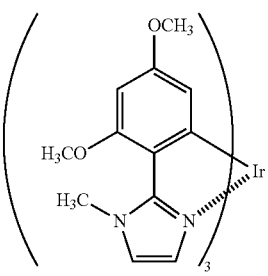
D-14
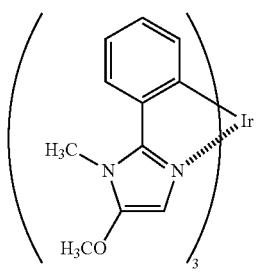
D-15
[Chemical formula 13]
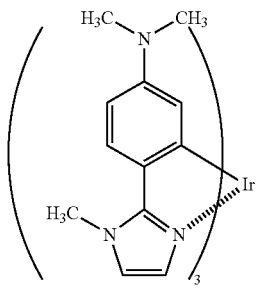
D-16
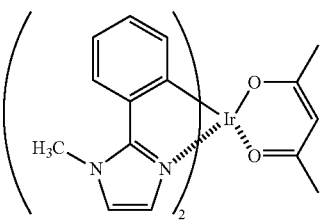
D-17
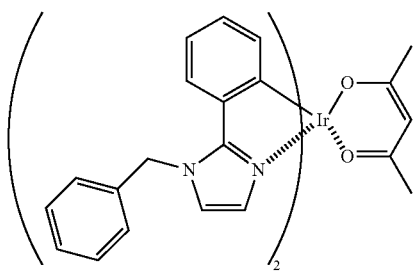
D-18
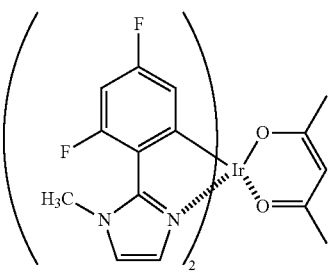
D-19
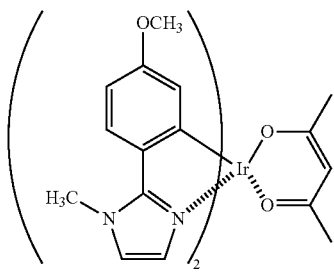
D-20
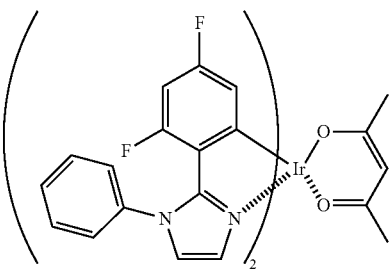
D-21

-continued
D-22 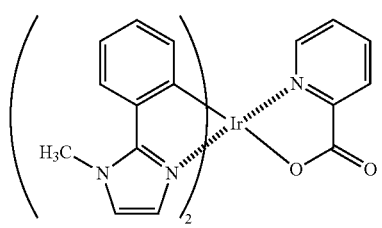
D-23 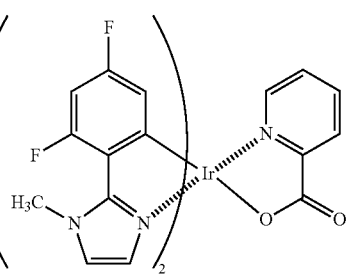
D-24 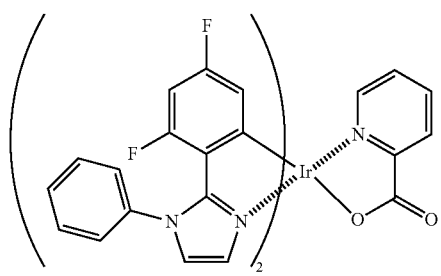
D-25 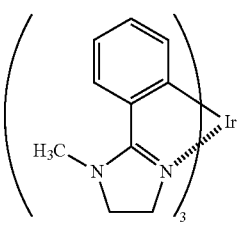
[Chemical formula 14]
D-26 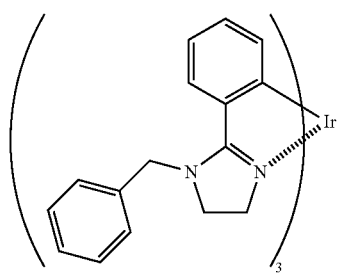
D-27 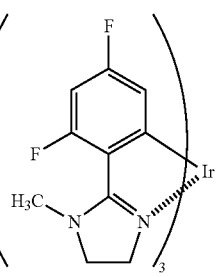
D-28 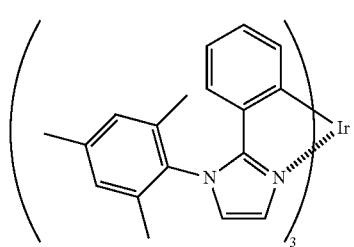
D-29 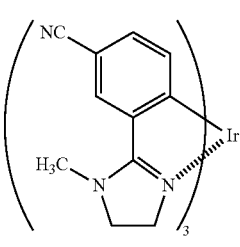
D-30 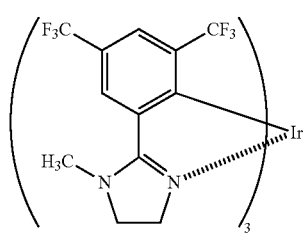
D-31 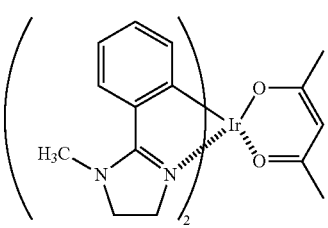
D-32 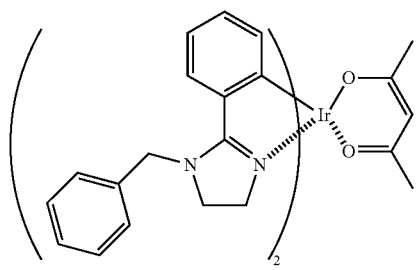
D-33 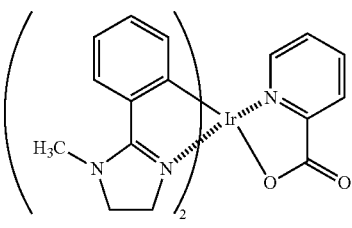

-continued
D-34 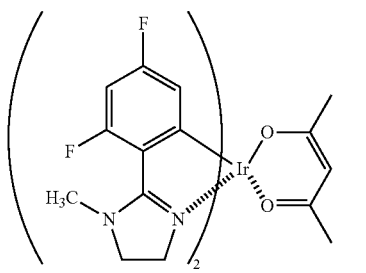
D-35 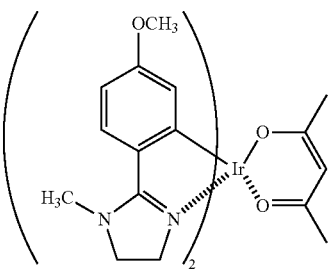
D-36 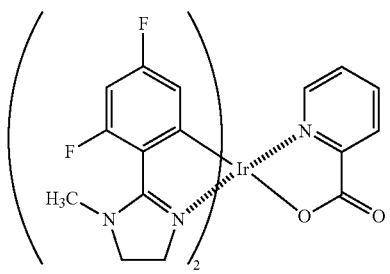
D-37 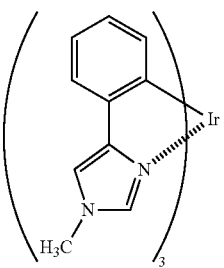
[Chemical formula 15]
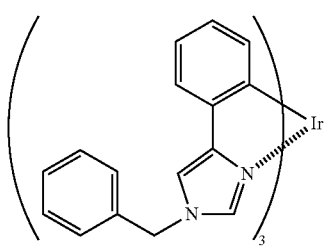
D-38
D-39 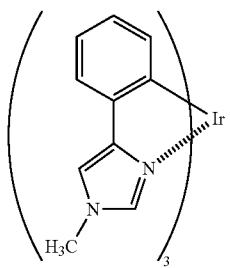
D-40 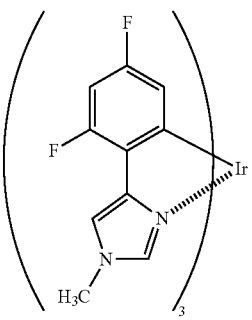
D-41 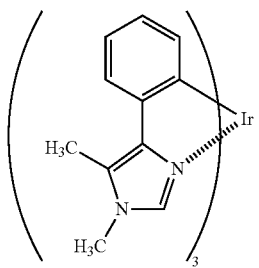
D-42 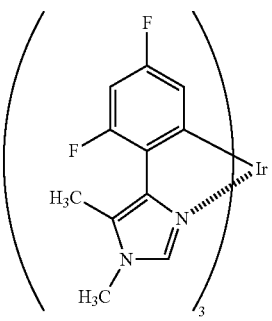

-continued
D-43
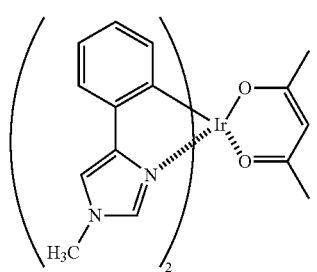
D-44
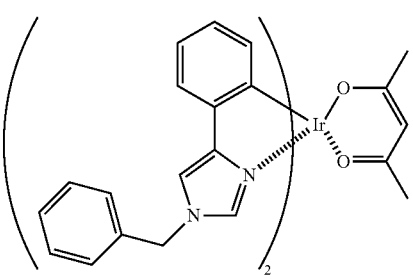
D-45
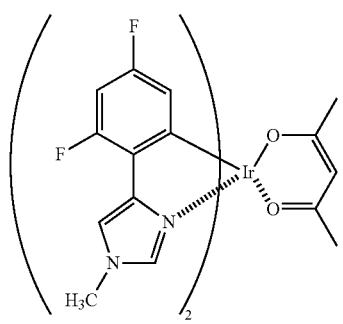
D-46
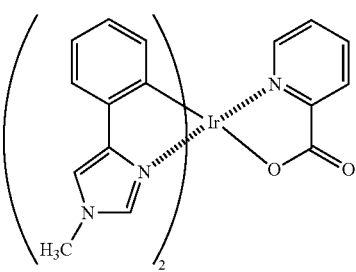
D-47
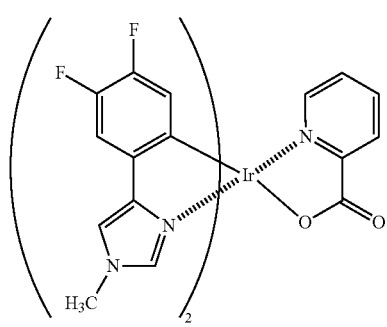
D-48
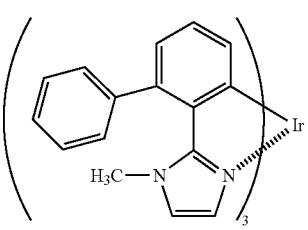
D-49
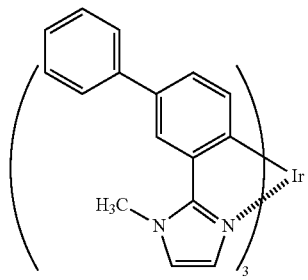
D-50
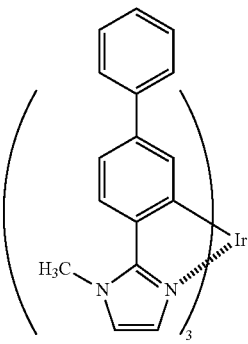
D-51
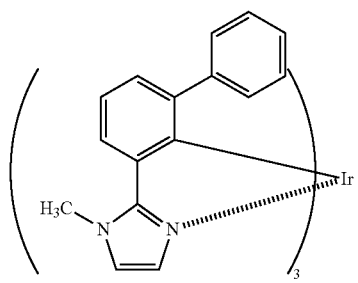

[Chemical formula 16]
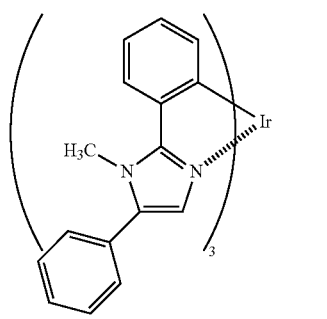 D-52
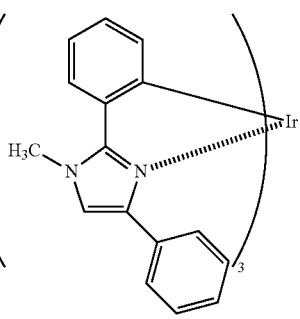 D-53
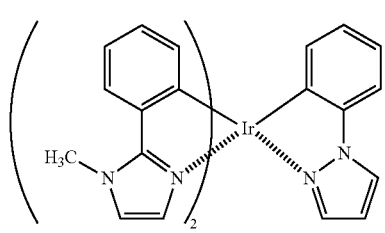 D-54
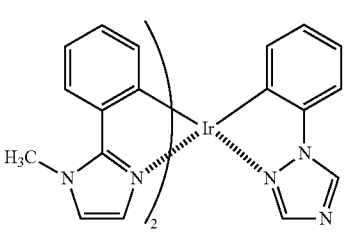 D-55
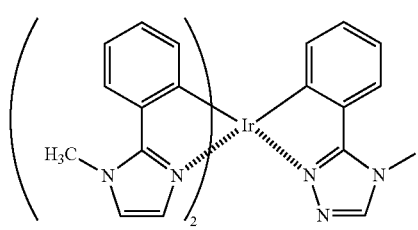 D-56
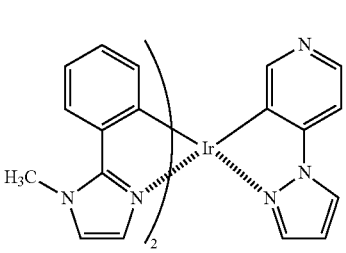 D-57
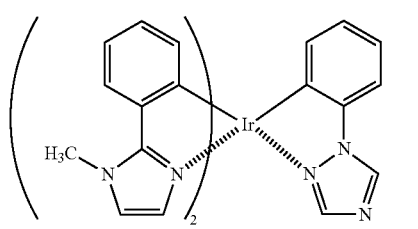 D-58
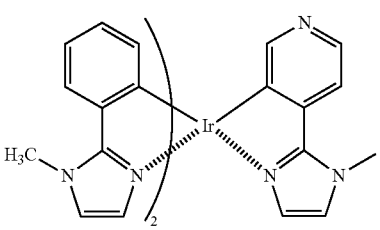 D-59
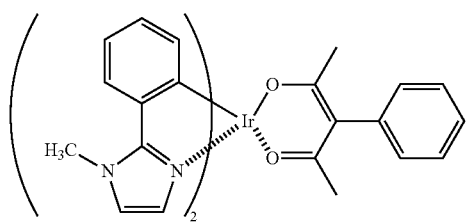 D-60
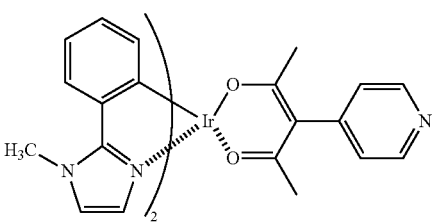 D-61
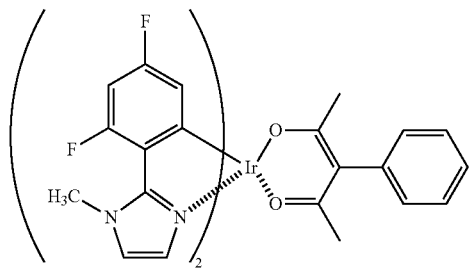 D-62

[Chemical formula 17]
D-63 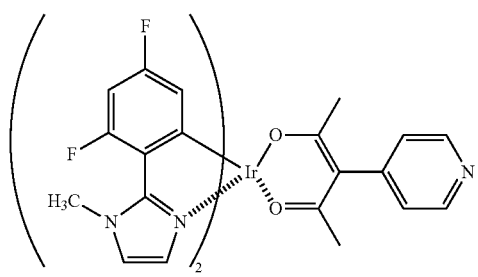
D-64 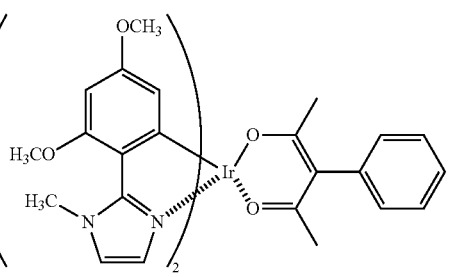
D-65 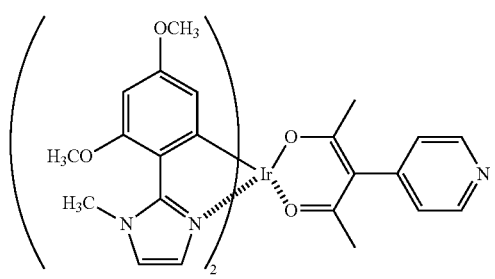
D-66 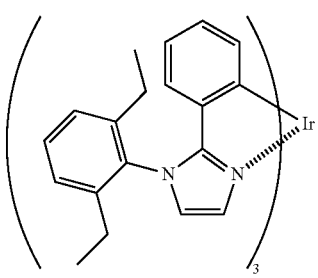
[Chemical formula 18]
D-67 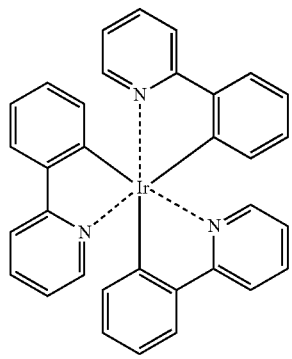
D-68 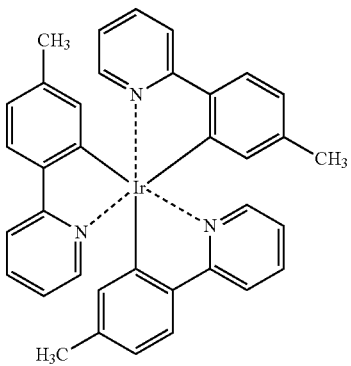
D-69 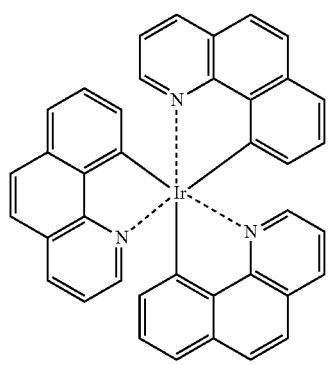
D-70 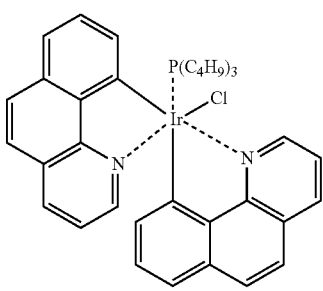

-continued
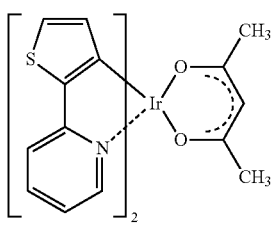
D-71
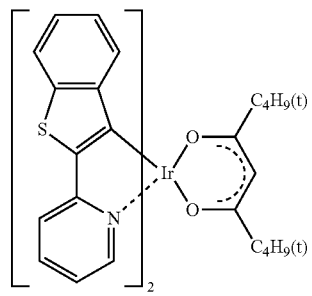
D-72
[Chemical formula 19]
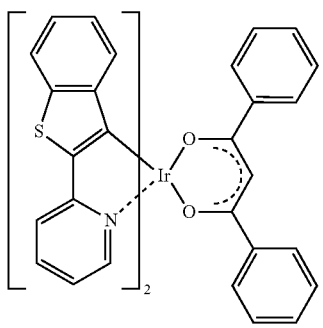
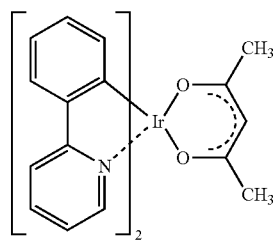
D-73
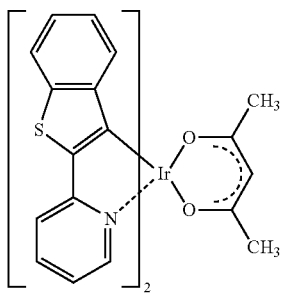
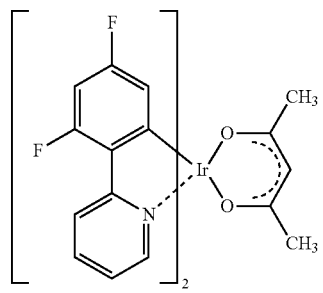
D-75
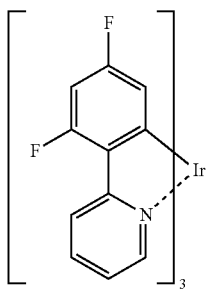
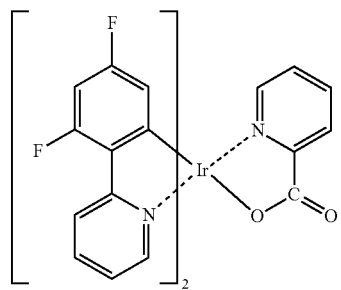
D-77
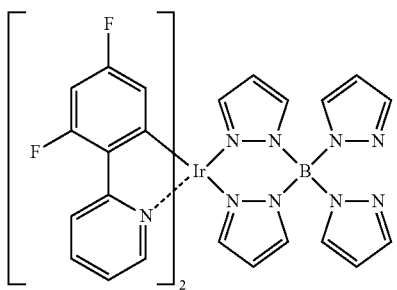
D-79
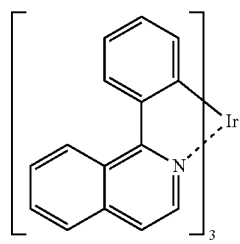
D-80

[Chemical formula 20]
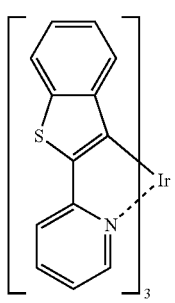
[Chemical formula 21]
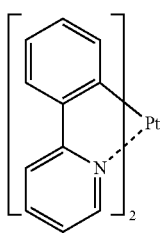
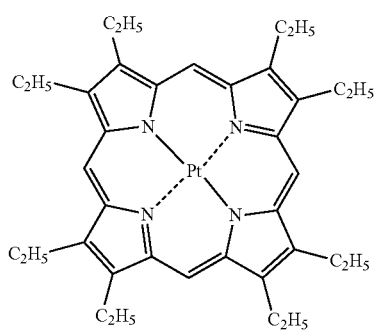
[Chemical formula 22]
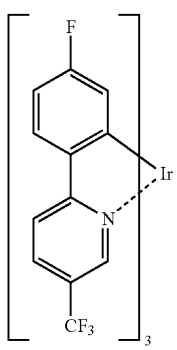
-continued
D-81  D-82
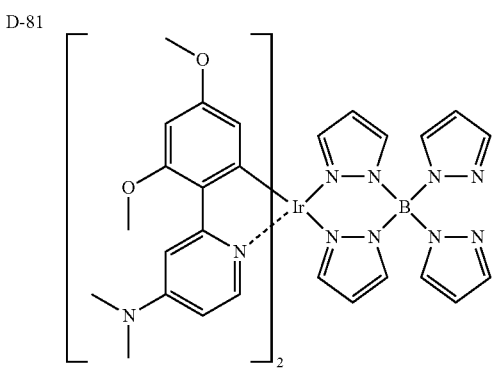
D-83  D-84
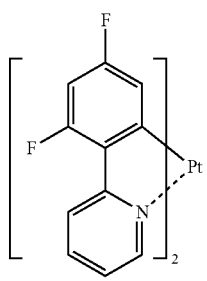
D-85  D-86
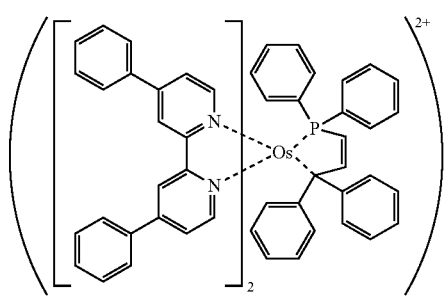
D-87  D-88
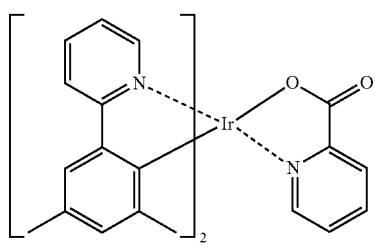

-continued
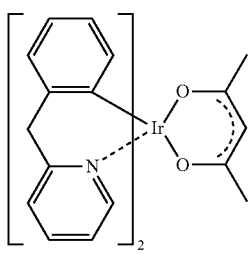
D-89
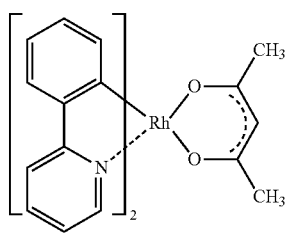
D-90
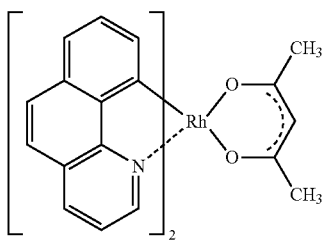
D-91
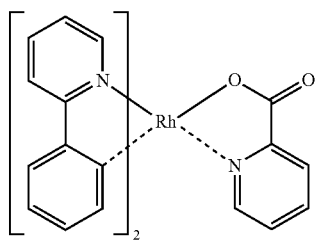
D-92
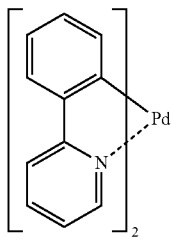
D-93
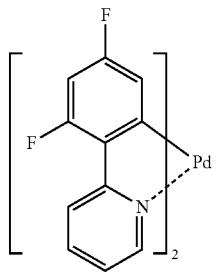
D-94
[Chemical formula 23]
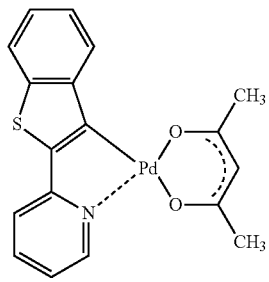
D-95
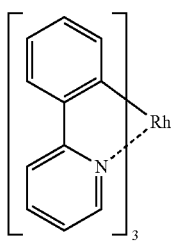
D-96
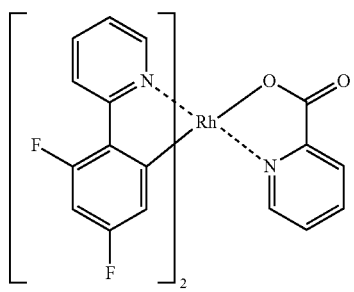
D-97
D-98
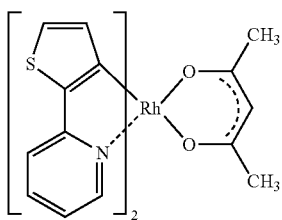

[Chemical formula 24]
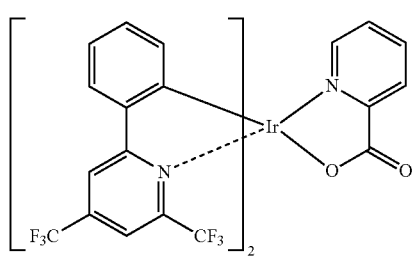 D-99
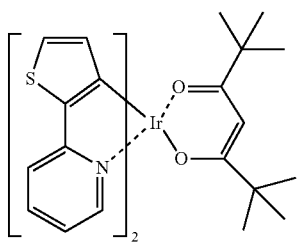 D-100
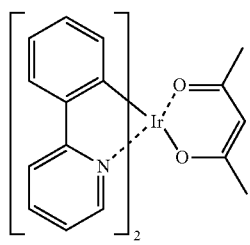 D-101
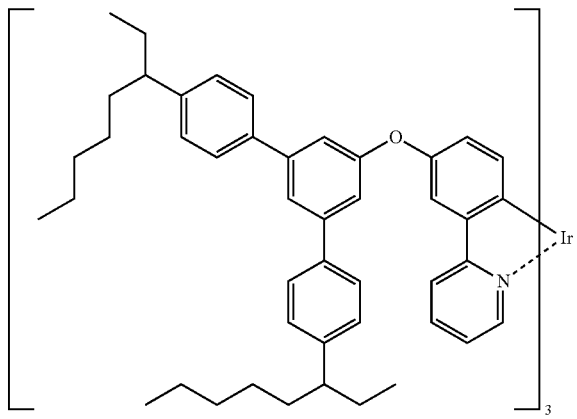 D-102
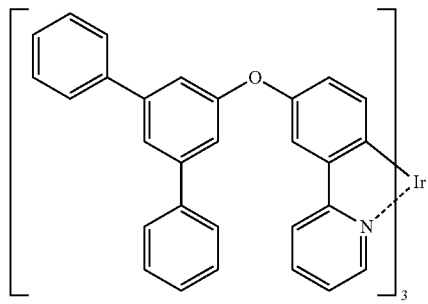 D-103
D-104
D-105
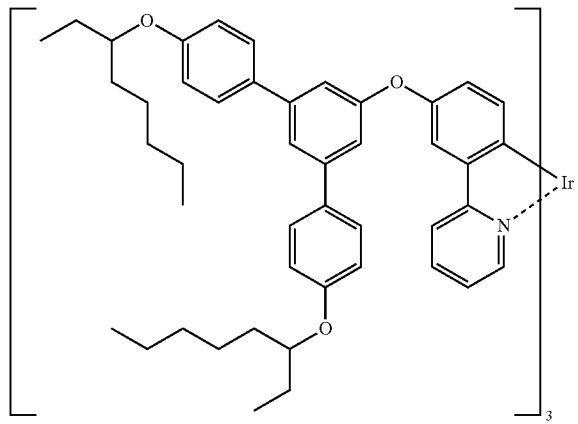

[Chemical formula 25]
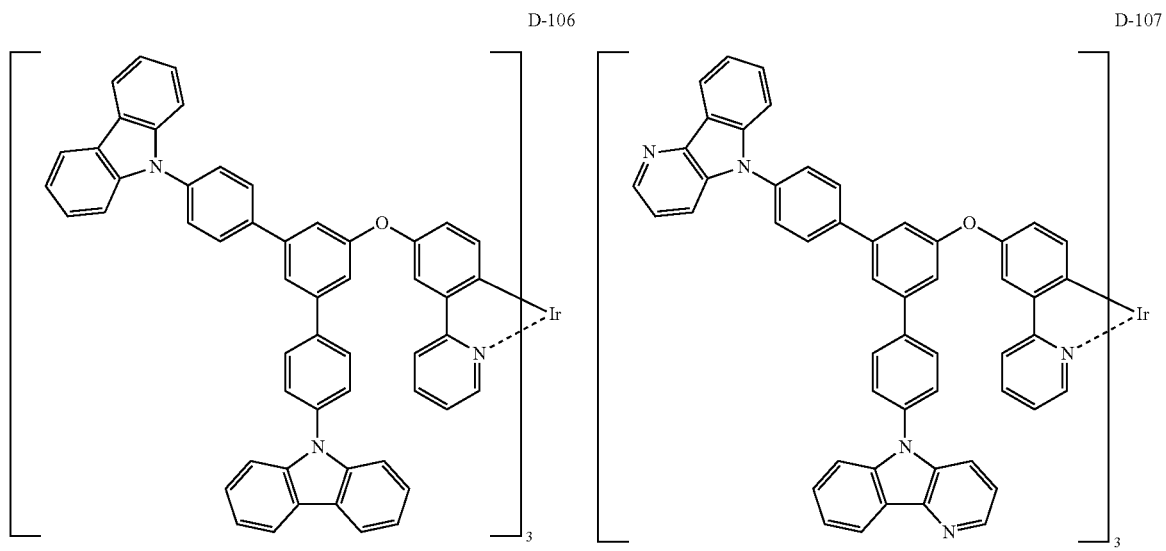
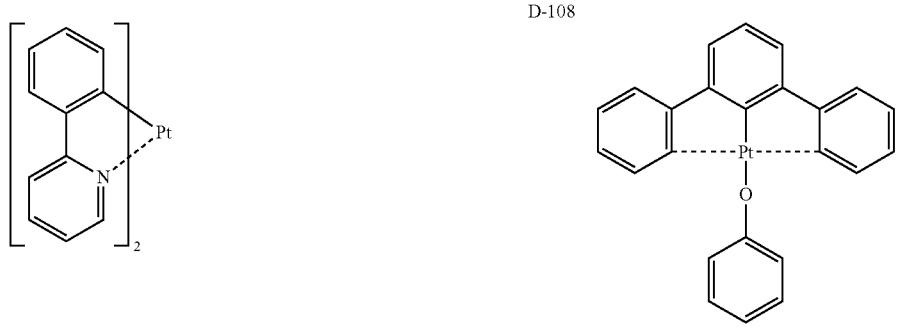
[Chemical formula 26]
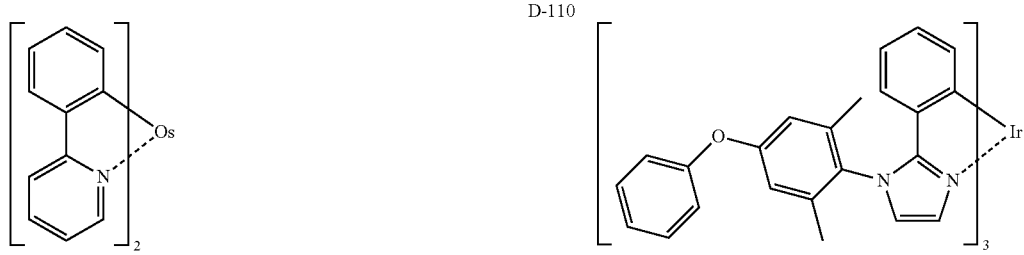
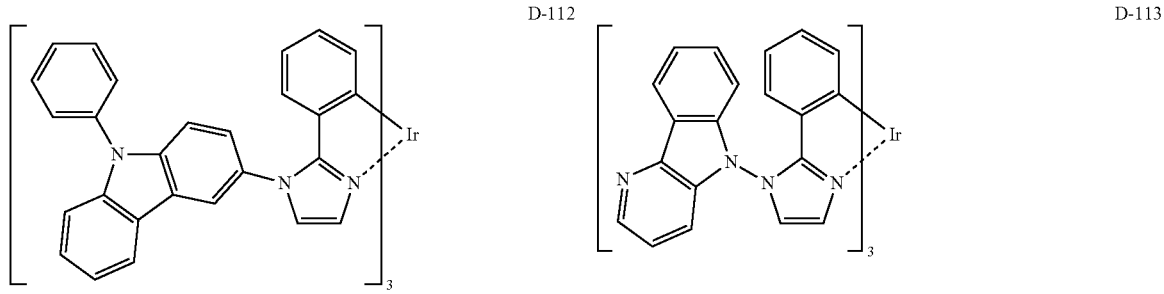

-continued
D-114 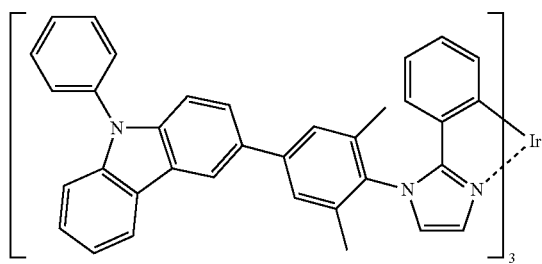
D-115 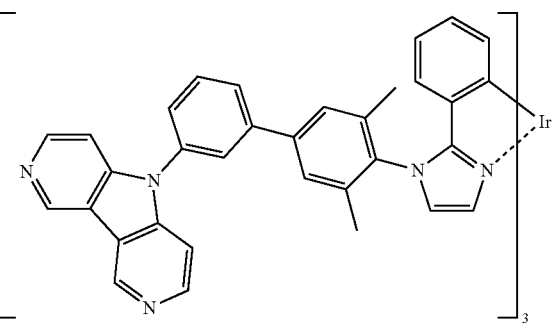
D-116 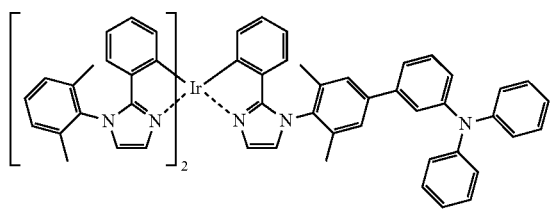
D-117 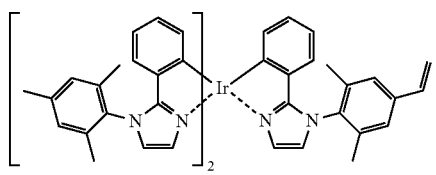
[Chemical formula 27]
D-118 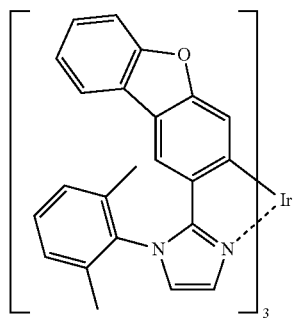
D-119 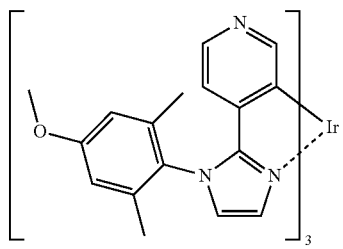
D-120 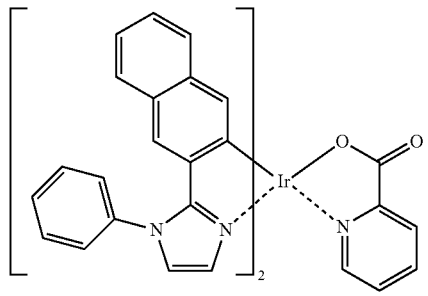
D-121 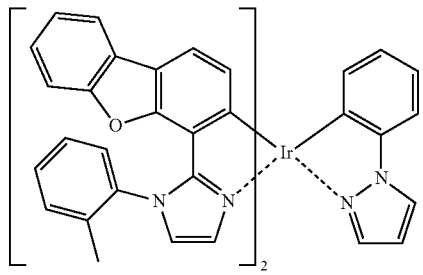
D-122 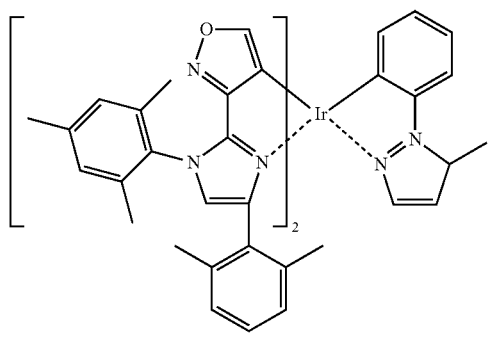
D-123 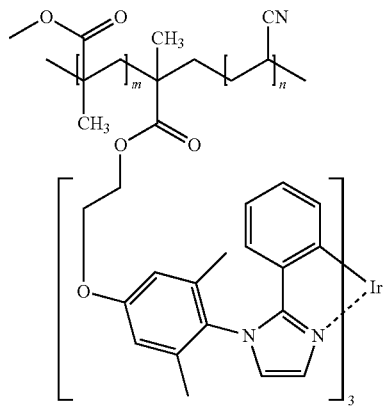

[Chemical formula 28]
D-124 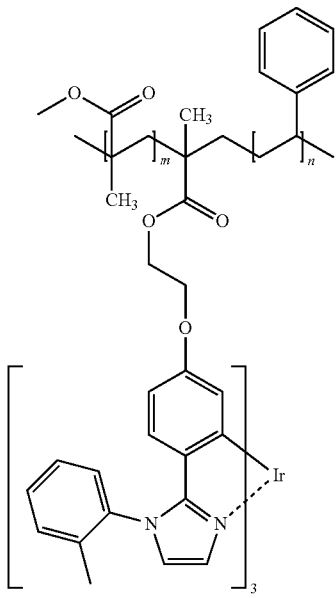
D-125 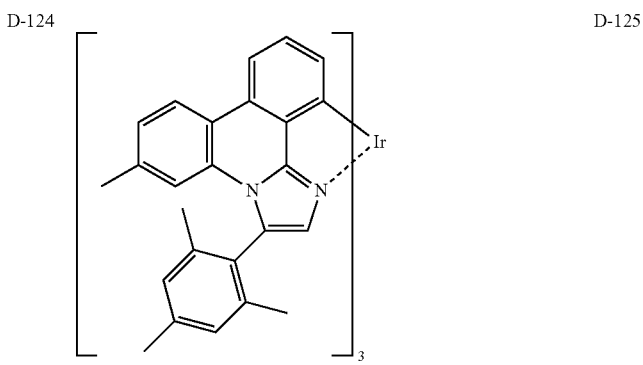
D-126 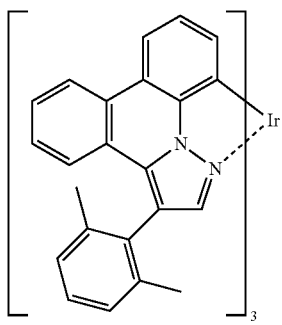
D-127 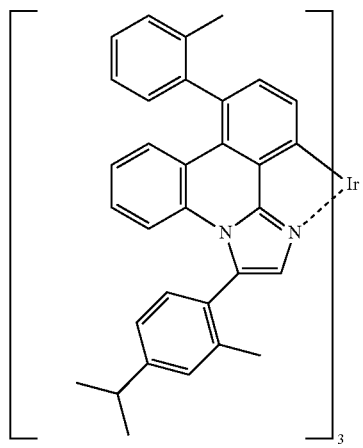
D-128 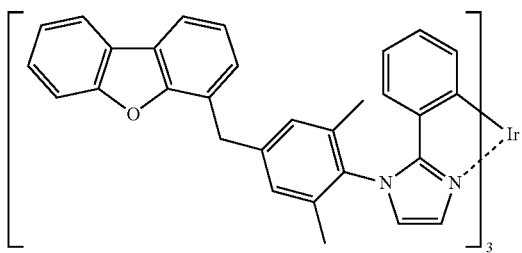
D-129 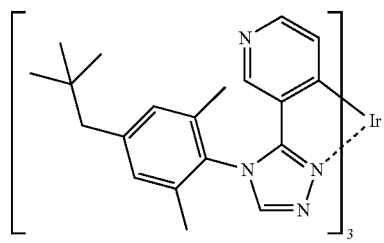

[Chemical formula 29]

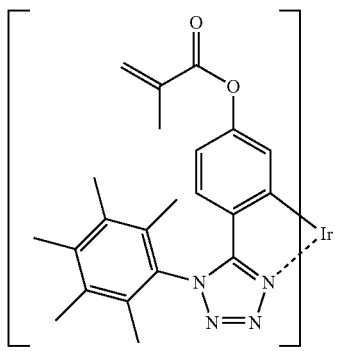

D-130

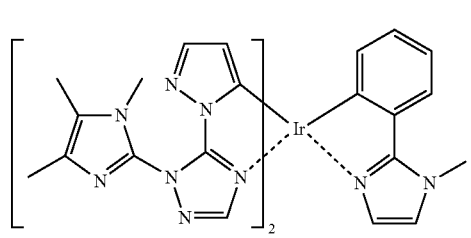

D-131

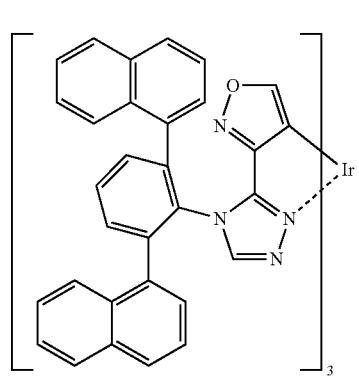

D-132

D-133

The phosphorescence-emitting dopant (phosphorescence-emitting compound) represented by the general formula (1) of the present invention has a highest occupied molecular orbital (HOMO) energy level of −5.15 to −3.50 eV and a lowest unoccupied molecular orbital (LUMO) energy level of −1.25 to +1.00 eV, and preferably a HOMO energy level of −4.80 to −3.50 eV and a LUMO energy level of −0.80 to +1.00 eV.

(2) Injecting Layer: Electron Hole-Injecting Layer 3, Electron-Injecting Layer 7

In the organic EL element of the present invention, an injecting layer may be provided as needed. The injecting layer is categorized into an electron-injecting layer and electron hole-injecting layer. The injecting layer may be provided between the anode and the light-emitting layer or between the anode and the electron hole-transporting layer, or between the cathode and the light-emitting layer or between the cathode and the electron-transporting layer, as described above.

The injecting layer of the present invention is a layer provided between the electrode and the organic functional layer to lower driving voltage and improve luminance, and described in detail in Chapter 2 "Electrode Materials", Div. 2 Chapter 2 (pp. 123-166) of "Organic EL element and its frontier of industrialization" (published by NTS Corporation, Nov. 30, 1998). The injecting layer is categorized into an electron-injecting layer and electron hole-injecting layer.

Details of the electron hole-injecting layer are also described in, for example, Japanese Application Laid-Open Publications Nos. Hei9-45479, He19-260062 and Hei8-288069, Employable examples of the electron hole-injecting material in the electron hole-injecting layer include polymers or aniline copolymers containing a triazole derivative(s), oxadiazole derivative(s), imidazole derivative(s), pyrazoline derivative(s), pyrazolone derivative(s), phenylenediamine derivative(s), arylamine derivative(s), amino-substituted chalcone derivative(s), oxazole derivatives(s), styrylanthracene derivative(s), fluorenone derivative(s), hydrazone derivative(s), stilbene derivative(s), silazane derivative (a), polyarylalkane derivative (a) and electroconductive polymers. Preferable examples are polythiophene derivatives, polyaniline derivatives and polypyrrole derivatives, and more preferable examples are polythiophene derivatives.

Details of the electron-injecting layer are also described in, for example, Japanese Application Laid-Open Publications Nos. Hei6-325871, Hei9-17574 and Hei10-74586, and is specifically exemplified by a buffer layer composed of a metal as typified by strontium, aluminum and the like, a buffer layer composed of an alkali metal as typified by lithium fluoride, a buffer layer composed of an alkali earth metal as typified by magnesium fluoride, a buffer layer composed of an oxide as typified by aluminum oxide. In the present invention, the buffer layer (i.e., injecting layer) is preferably a very thin layer and is preferably composed of potassium fluoride or sodium fluoride. The thickness of the injecting layer is from 0.1 to 5 μm, preferably from 0.1 to 100 nm, more preferably from 0.5 to 10 nm, and most preferably 0.5 to 4 nm.

(3) Electron Hole-Transporting Layer 4

An electron hole-transporting material in the electron hole-transporting layer may be a compound employed in the electron hole-injecting layer. The electron hole-transporting material is preferably a porphyrin compound, aromatic tertiary amine compound or stylylamine compound, and more preferably an aromatic tertiary amine compound. Representative examples of the aromatic tertiary anime compound and stylylamine compound include N,N,N',N'-tetraphenyl-4,4'-diaminophenyl; N,N'-diphenyl-N,N'-bis(3-methylphenyl)-[1,1'-biphenyl]-4,4'-diamine (TPD); 2,2-bis(4-di-p-tolylaminophenyl)propane; 1,1-bis(4-di-p-tolylaminophenyl)cyclohexane; N,N,N',N'-tetra-p-tolyl-4,4'-diaminobiphenyl; 1,1-bis(4-di-p-tolylaminophenyl)-4-phenylcyclohexane; bis(4-dimethylamino-2-methylphenyl) phenylmethane; bis(4-di-p-tolylaminophenyl) phenylmethane; N,N'-diphenyl-N,N'-di(4-methoxyphenyl)-4,4'-diaminobiphenyl; N,N,N',N'-tetraphenyl-4,4'-diaminodlphenyl ether; 4,4'-bis(diphenylamino) quaterphenyl; N,N,N-tri(p-tolyl)amine, 4-(di-p-tolylamino)-4'-[4-(di-p-tolylamino)styryl]stilbene; 4-N,N-diphenylamino-(2-diphenylvinyl)benzene; 3-methoxy-4'-N,N-diphenylaminostylbenzene; N-phenylcarbazole; a compound having two condensed aromatic rings in the molecule described in U.S. Pat. No. 5,061,569 such as 4,4'-bis[N-(1-nahthyl)-N-phenylamino]biphenyl (NPD); and a compound described in Japanese Patent Application Laid-Open Publication No. Hei4-308688, i.e., 4,4',4"-tris[N-(3-methylphenyl)-N-phenylamino]triphenylamine (MT-DATA) in which three triphenylamine units are bonded in a starburst form.

Polymer materials where the above compound(s) are introduced in their polymer chains or are present as their main chains may also be used. Further, inorganic compounds such as p-Si and p-Sic may also be used as an electron hole-injecting material or electron hole-transporting material.

Still further, an electron hole-transporting material having properties like those of p-type semiconductors, as described in Japanese Application Laid-Open Publications Nos. Hei4-297076, 2000-196140 and 2001-102175, J. Appl. Phys. 95, 5773 (2004), Japanese Laid-Open Application Publication No. Hei11-251067, J. Huang et al, (Applied Physics Letters 80 (2002), p. 139) and Japanese Application Laid-Open Publication No. 2003-519432, may also be used The electron hole-transporting layer may be obtained by forming a thin layer with the above-described electron hole-transporting material(s) by a known method such as vacuum deposition, spin coating, casting, ink jetting or LB method. The thickness of the electron hole-transporting layer is not particularly limited, but normally from about 5 nm to 5 µm, and preferably from 5 to 200 nm. The electron hole-transporting layer may consist of a single layer containing one or more types of the above materials.

Preferable examples of the electron hole-transporting material will be described below, but the present invention is not limited thereto.

[Chemical formula 30]

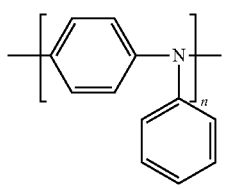

(1)

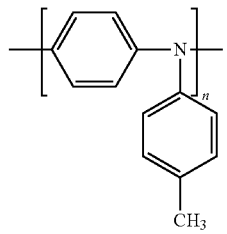

(2)

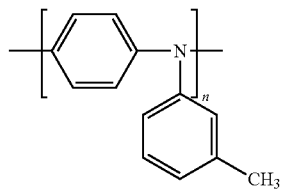

(3)

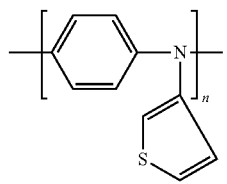

(4)

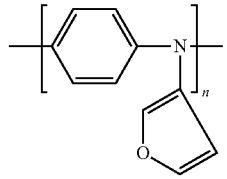

(5)

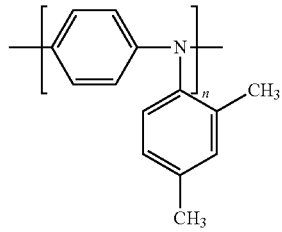

(6)

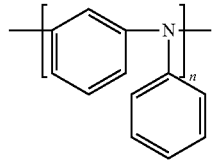

(7)

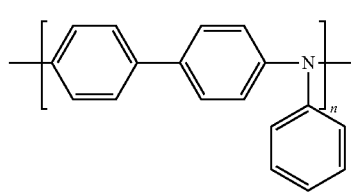

(8)

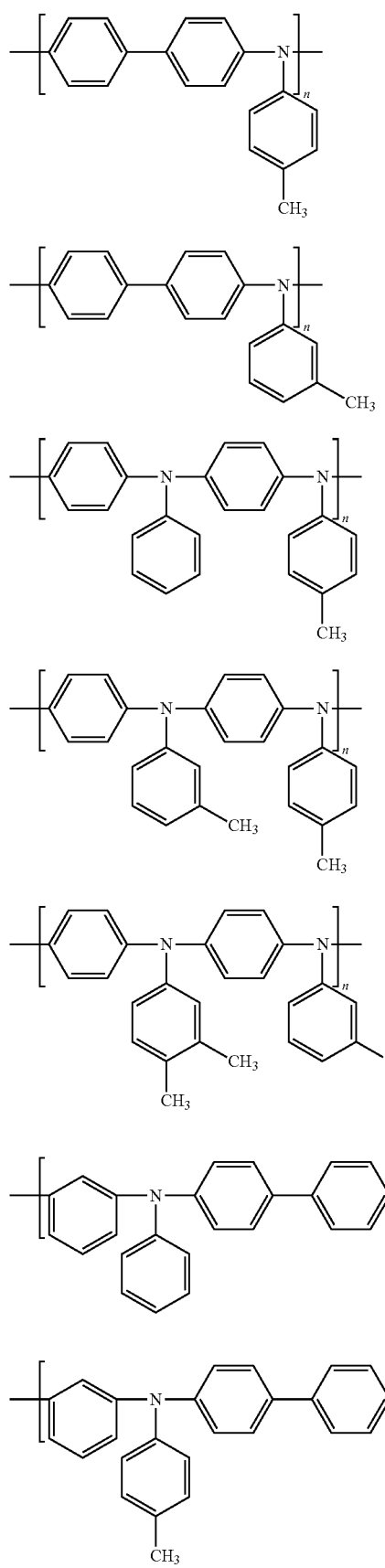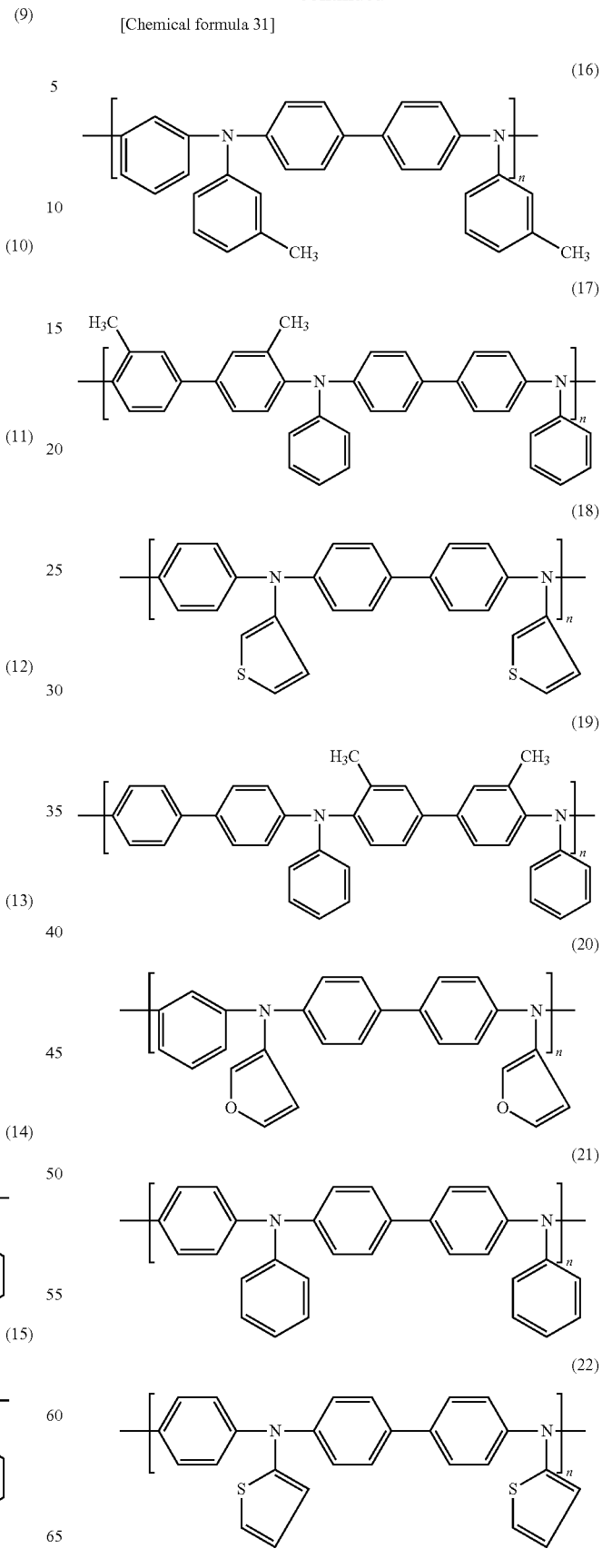

(23)
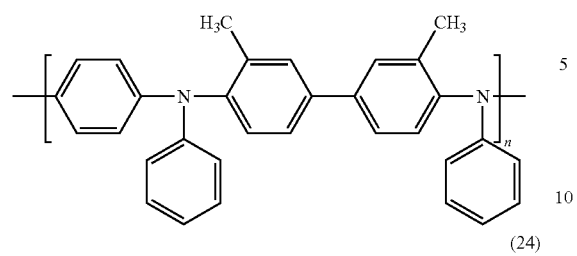
(24)
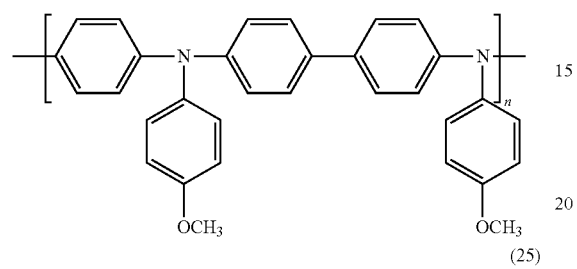
(25)
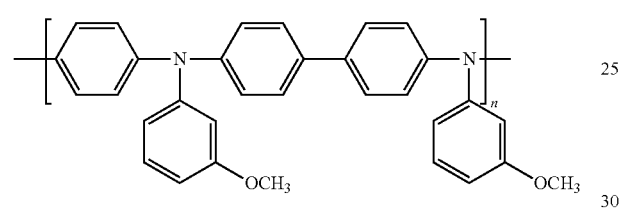
[Chemical formula 32]
(26)
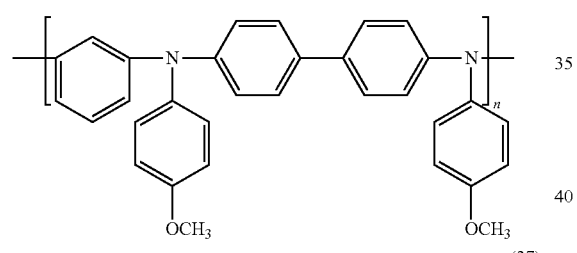
(27)
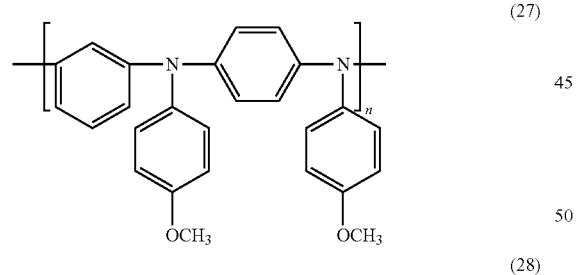
(28)
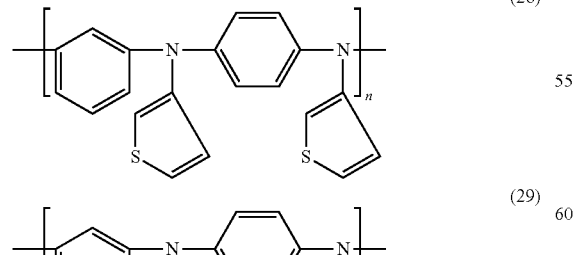
(29)
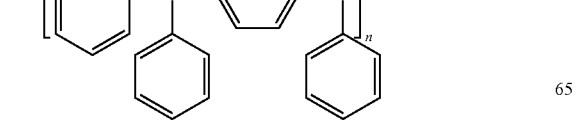
(30)
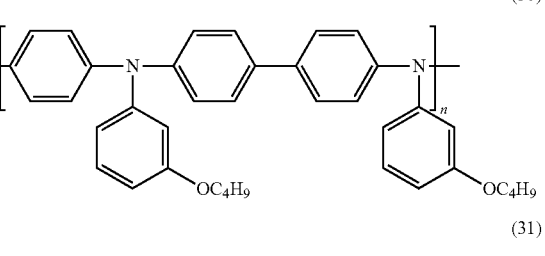
(31)
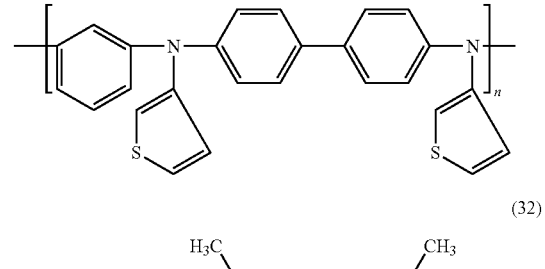
(32)
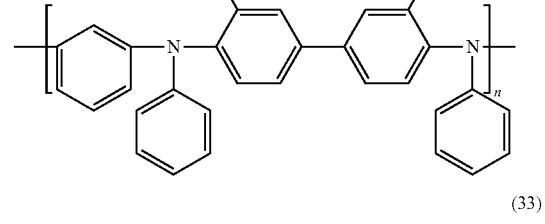
(33)
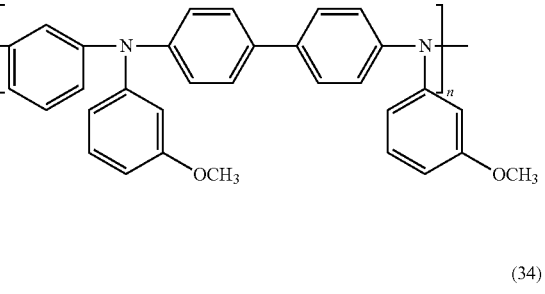
(34)
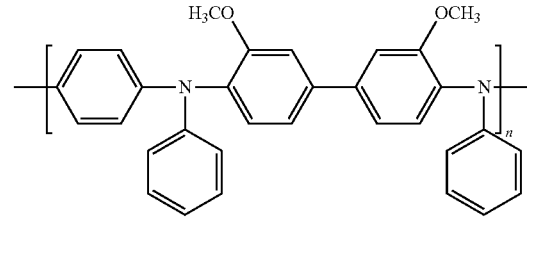
(35)
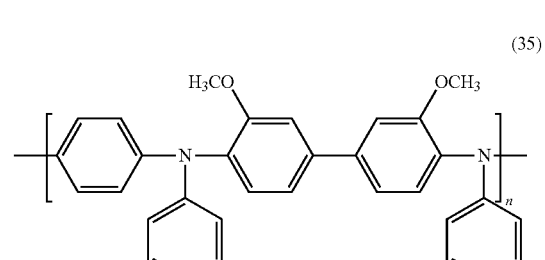
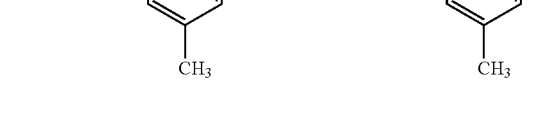

[Chemical formula 33]
(36)
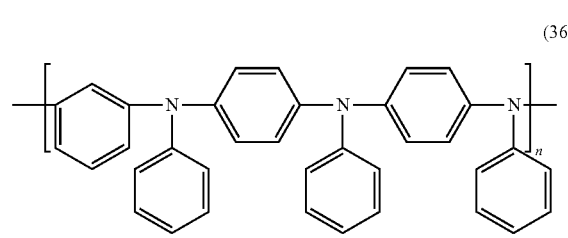
(37)
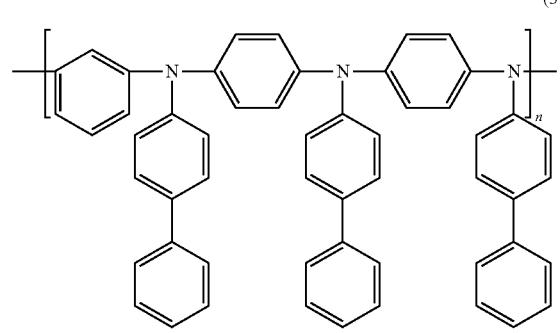
(38)
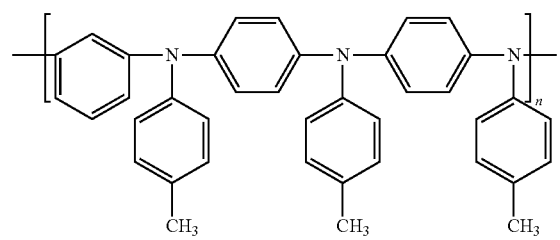
(39)
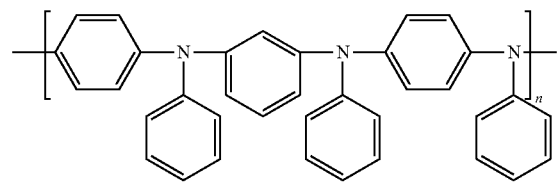
(40)
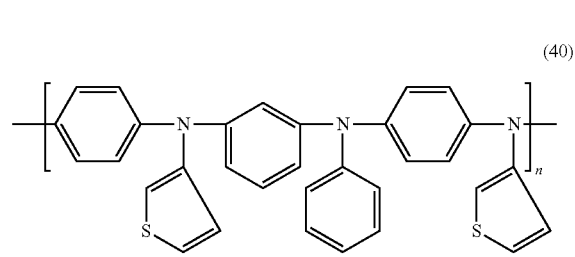
(41)
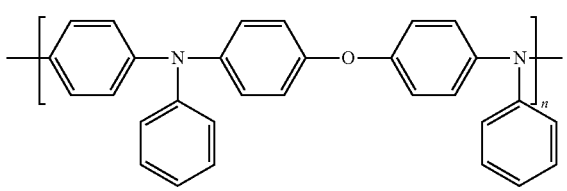
(42)
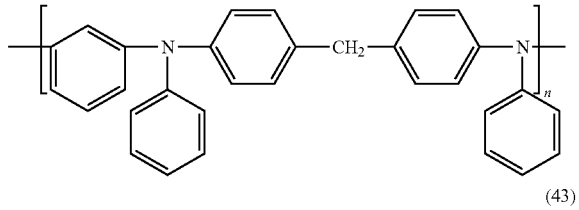
(43)
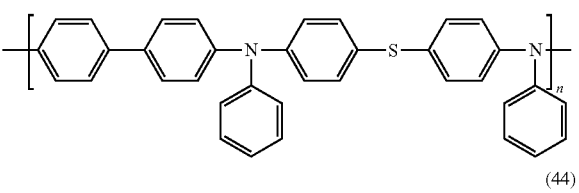
(44)
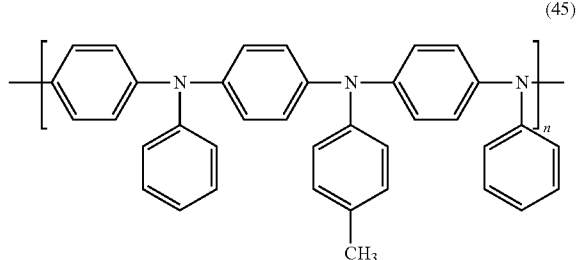
[Chemical formula 34]
(45)
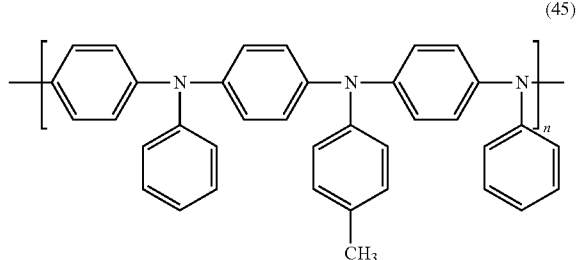
(46)
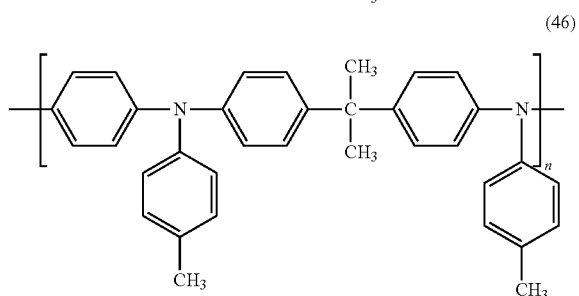
(47)
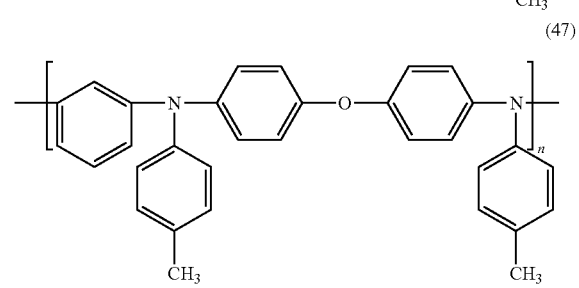
(48)
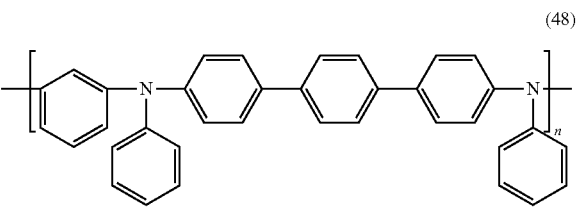

[Chemical formula 35]
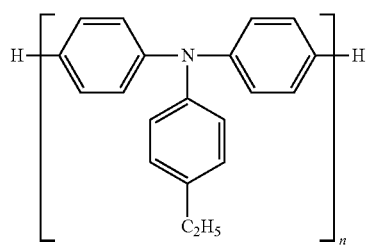 (49)
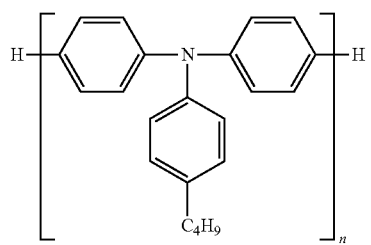 (50)
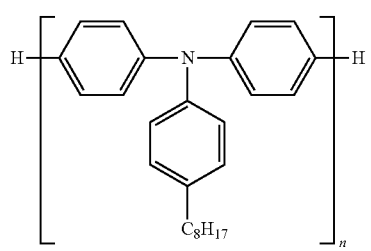 (51)
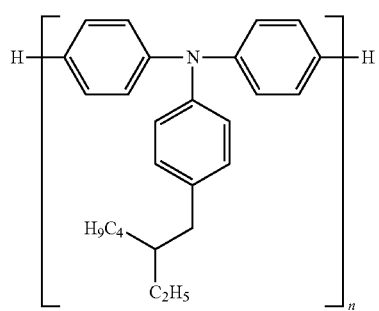 (52)
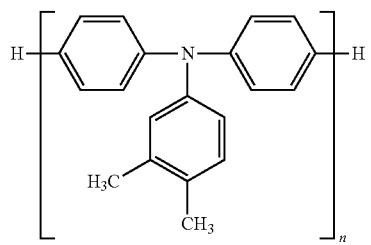 (53)
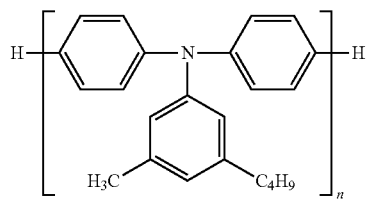 (54)
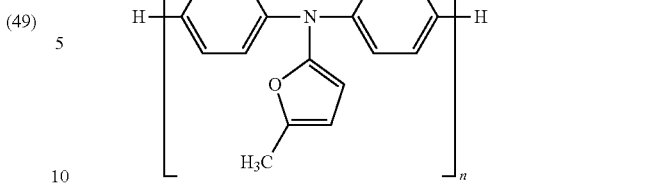 (55)
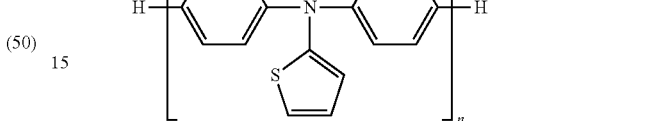 (56)
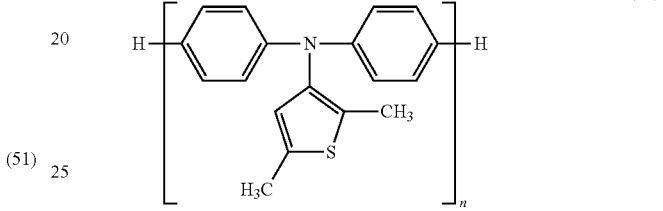 (57)
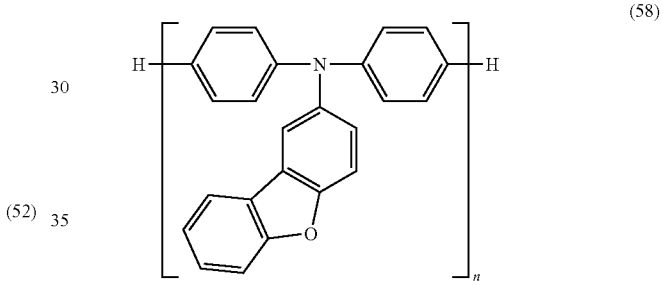 (58)
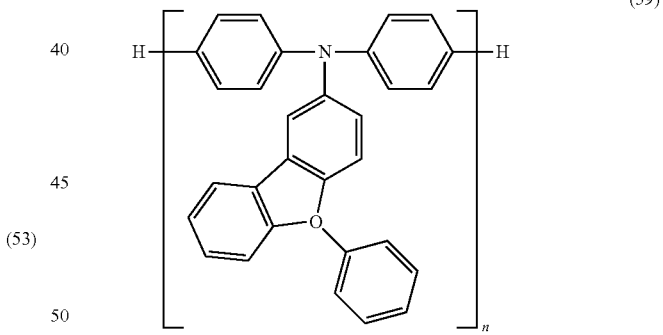 (59)
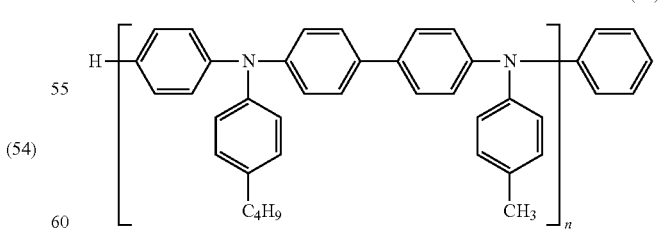 (60)
In the above-exemplified compounds, n represents their polymerization degrees. In terms of formation of layers, purification of compounds and the like, it is preferable that their weight-average molecular weights are from 50,000 to 200,000.

These polymer compounds can be synthesized by a known method described in Makromol Chem., 193, p. 909 (1992), for example.

(4) Electron-Transporting Layer 6

Te electron-transporting layer is composed of a material having electron-transporting properties, and in a broad sense, including an electron-injecting layer and electron hole-blocking layer. One or more electron-transporting layers may be provided.

Heretofore, in the case of providing a single or multiple electron-transporting layers, an electron-transporting material (also used as an electron hole-blocking material) used in the electron-transporting layer that is adjacent to the light-emitting layer on the side of the cathode may be any material having properties for transporting electrons injected from the cathode to the light-emitting layer, and may be selected from conventionally known compounds such as metal complexes, namely, metal complexes of fluorene, derivatives, carbazole derivatives, azacarbazole derivatives, oxadiazole derivatives, triazole derivatives, silole derivatives, pyridine derivatives, pyrimidine derivatives, 8-quinolinole derivatives, for example.

In addition, metal-free or metalphthalocyanine, or metal-free or metalphthalocyanine whose end(s) are substituted with an alkyl group(s) sulfonic acid group(s) or the like may be suitably used as the electron-transporting material.

Among them, carbazole derivatives, azacarbazole derivatives, pyridine derivatives are preferable, and azacarbazole derivatives are more preferable for the present invention.

The electron-transporting layer may be obtained by forming a thin layer with the above-described electron-transporting material(s) by a known method such as spin coating, casting, printing including ink jetting or LB method, and preferably obtained by a wet process using an application solution containing the above-described electron-transporting material(s), semiconductor nanoparticles (described later) and fluoroalcohol as a solvent.

The thickness of the electron-transporting layer is not particularly limited, but normally from about 5 nm to 5 μm, and preferably from 5 to 200 nm. The electron-transporting layer may be a single layer composed of one or more types of the above materials.

Further, an electron-transporting layer doped with impurity(ies) as guest materials in addition to the above-described semiconductor nanoparticles and having high n-type properties may be used. Examples thereof are described in Japanese Application Laid-Open Publications Nos. Hei4-297076, Hei10-270172, 2000-196140 and 2001-102175, and J, Appl, Phys., 95, 5773 (2004), for example.

The electron-transporting layer used in the present invention preferably contains an alkali metal salt of an organic compound. The organic compound are not particularly limited. Examples includes alkali metal salts of formic acid, acetic acid, propionic acid, butyric acid, valeric acid, capronic acid, enanthic acid, caprylic acid, oxalic acid, malonic acid, succinic acid, benzoic acid, phthalic acid, isophthalic acid, telephthalic acid, salicylic acid, pyruvic acid, lactic acid, malic acid, adipic acid, mesylic acid, tosylic acid, benzensulfonic acid; preferably an alkali metal salt of formic acid, acetic acid, propionic acid, butyric acid, valeric acid, capronic acid, enanthic acid, caprylic acid, oxalic acid, malonic acid, succinic acid and benzoic acid; a more preferable example is an alkali metal salt of an aliphatic carboxylic acid, wherein the number of carbons of the aliphatic carboxylic acid is 4 or less, such as formic acid, acetic acid, propionic acid or butyric acid; and most preferable example is an alkali metal salt of acetic acid.

An alkali metal in the alkali metal salt of the organic compound is not particularly limited, and is exemplified by Na, K and Cs. K and Cr are preferable, and Cs is more preferable.

The alkali metal salt of an organic compound is exemplified by salts of the above-described organic compounds and the above-described alkali metals, and preferably lithium formate, potassium formate, sodium formate, cesium formate, lithium acetate, potassium acetate, sodium acetate, cesium acetate, lithium propionate, sodium propionate, potassium propionate, cesium propionate, lithium oxalate, sodium oxalate, potassium oxalate, cesium oxalate, lithium malonates, sodium malonate, potassium malonate, cesium malonate, lithium succinate, sodium succinate, potassium succinate, cesium succinate, lithium benzoate, sodium benzoate, potassium benzoate and cesium benzoate, more preferably lithium acetate, potassium acetate, sodium acetate and cesium acetate, and most preferably cesium acetate.

A content of the above doping material is preferably 1.5 to 35% by mass, more preferably 3 to 25% by mass, and most preferably 5 to 15% by mass with respect to the electron-transporting layer to which the doping material is to be added.

(5) Anode 2

For the anode 2 of the organic EL element of the present invention, a metal, alloy, electroconductive compound or a mixture thereof each of which has a high work function (4 eV or more), is preferably used as an electrode material. Specific examples of the electrode material include metals such as Au and transparent electroconductive materials such as CuI, indium thin oxide (ITO), $SnO_2$ and ZnO. A material that is amorphous and can be used for a transparent electroconductive film such as IDIXO ($In_2O_3$—ZnO) may also be used.

The anode 2 may be obtained by forming a thin film with the above-described electrode material(s) by a method such as deposition or sputtering followed by patterning by photolithography to form a desired pattern. In the case where patterning does not need to be so accurate (about 100 μm or more), patterning may be conducted in deposition or sputtering of the above-described electrode material using a mask in a desired shape.

In the case of using a compound that is appliable such as an organic electroconductive compound, a wet film forming method such as printing or coating may be used.

For extracting emitted light from the anode, the transmittance of the anode is desirably 10% or more, and the sheet resistance of the anode is preferably a few hundreds Ω/□ or less. The thickness of the layer is usually in a range of 10 to 1000 nm, and preferably 10 to 200 nm, while depending on its material.

(6) Cathode 8

For the cathode 8 of the organic EL element of the present invention, a metal, alloy, electroconductive compound or a mixture thereof, each of which has a low work function (4 eV or less) is preferably used as an electrode material.

Examples of such an electrode material include sodium, sodium-potassium alloy, magnesium, lithium, a mixture of magnesium and copper, a mixture of magnesium and silver, a mixture of magnesium and aluminum, a mixture of magnesium and indium, a mixture of aluminum and aluminum oxide ($Al_2O_3$), indium, a mixture of lithium and aluminum and rare earth elements, Among them, in terms of electron-injecting properties and resistance against oxidation and the like, a preferable material is a mixture of an electron-injecting metal and a secondary metal that has work function higher than that of the electron-injecting material and is stable, for example, a mixture of magnesium and silver, a mixture of magnesium and aluminum, a mixture of magnesium and indium, a mixture of aluminum and aluminum oxide ($Al_2O_3$), a mixture of lithium and aluminum, aluminum and the like.

The cathode 8 may be obtained by forming a thin layer with the above-described electrode material(s) by a method such as deposition, sputtering or the like.

For the cathode 8, sheet resistance of the cathode is preferably a few hundreds Ω/☐ or less, and the thickness of the cathode is normally from 10 nm to 5 μm, and preferably from 50 to 200 nm. To improve luminance, it is preferable that the anode or the cathode of the organic EL element is transparent or semi-transparent to transmit the emitted light.

The transparent or semi-transparent cathode 8 may be obtained by forming a layer having a thickness of 1 to 20 nm with the above-described metal and subsequently applying the transparent electroconductive material(s) described in the description of the anode 2 on the cathode; by using this procedure, an organic EL element including the anode 2 and the cathode 8, both of which are transparent are obtained.

<<Supporting Substrate 1>>

The supporting substrate 1 of the organic EL element of the present invention (hereinafter also referred to as substrate body, substrate, base, supporting body or the like) may be composed of, for example, glass or plastic, but types of glasses and plastics are not particularly limited. The supporting substrate 1 may be transparent or opaque. In the case where light is extracted from the side of the supporting substrate 1, the supporting substrate 1 is preferably transparent.

Preferable examples of the transparent supporting substrate 1 include a glass substrate, a quartz substrate and a transparent resin film. A flexible substrate achieves effects for achieving storage stability in high temperature and suppressing change in chromaticity are achieved more greatly than a rigid substrate does. Thus, a particularly preferable supporting substrate is made from a resin film which is flexible and is capable of providing flexibility for an organic EL element.

Examples of the resin film include films of polyesters such as polyethylene terephthalate (PET) and polyethylene naphthalate (PEN), polyethylene, polypropylene, cellophane, cellulose esters and their derivatives such as cellulose diacetate, cellulose triacetate, cellulose acetate butylate, cellulose acetate propionate (CAP), cellulose acetate phthalate (TAC) and cellulose nitrate, polyvinylidene chloride, polyvinyl alcohol, polyethylene vinyl alcohol, syndiotactic polystyrene, polycarbonate, norbornene resins, polymethylpentene, polyether ketones, polyimides, polyether sulfone (PES) polyphenylene sulfide, polysulfones, polyether imide, polyether ketone imide, polyamide, fluorine resins, nylon, polymethyl methacrylate, acrylics and polyarylates, and cycloolefin resins such as ARTON (trade name, manufactured by JSR Corp.) and APEL (trade name, manufactured by Mitsui Chemicals Inc.)

On the surface of the resin film, an inorganic or organic coating film or a hybrid coating film composed of the both may be formed. The coating film is preferably a high barrier film having a water vapor transmission rate at 25±0.5° C. and 90±2% RH of 0.01 g/($m^2$·24 h) or less determined according to JIS K 7129-1992, and more preferably a high barrier film having an oxygen transmission rate of 10 ($m^2$·h·MPa) or less determined according to JIS K 7126-1987 and a water vapor transmission rate of $10^3$ g/($m^2$·24 h) or less, preferably $10^{-5}$ g/($m^2$·24 h)

The barrier film may be formed with any material(s) that can prevent penetration of substances such as moisture and oxygen causing degradation of the element, and usable examples of the material include silicon oxide, silicon dioxide and silicon nitride. To improve weakness of the film, a barrier film having a laminate structure composed of an inorganic layer and an organic material layer is preferred. The order of these stacked inorganic layer(s) and organic layer(s) is not particularly limited, but it is preferable to stack the inorganic layers and organic layers alternately.

The barrier film may be formed by any method without particular limitation. For example, vacuum deposition, sputtering, reactive sputtering, molecular beam epitaxy, ionized-cluster beam method, ion plating, plasma polymerization, atmospheric pressure plasma polymerization, plasma CVD, laser CVD, thermal CVD, or coating may be used and atmospheric pressure plasma polymerization as described in Japanese Patent Application Laid-Open Publication No. 2004-68143 is particularly preferred.

Examples of the opaque supporting substrate 1 include metal plates such as an aluminum plate and stainless plate, films, opaque resin substrates and ceramic substrates.

In the organic EL element of the present invention, efficiency of external extraction of light at room temperature is preferably 1% or more, and more preferably 5% or more.

The efficiency of external extraction of light (%) is obtained by the equation:

efficiency of external extraction of light (%) the number of photons emitted to the outside of an organic EL element/the number of electrons flowed into the organic EL element×100

<<Sealing (Sealing Adhesive 9, Sealing Member 10)>>

A sealing method applicable to the organic EL element of the present invention is exemplified by a method for adhering a sealing member to electrodes and a supporting substrate with an adhesive.

The sealing member is disposed so as to cover a displaying area of the organic EL element(s), and may be a concave or flat. Transparency and insulation properties are not particularly limited.

Specific examples of the sealing member include a glass plate, a composite of polymer plate and film and a composite of metal plate and film, Particular examples of a glass plate include soda-lime grass plates, barium-strontium-containing glass plates, lead glass plates, aluminosilicate glass plates, borosilicate glass plates, barium borosilicate glass plates and quartz plates. Examples of a polymer plate include polycarbonate plates, acrylic plates, polyethylene terephthalate plates, polyethersulfide plates, polysulfone plates. Examples of a metal plate include plates composed of one or more types of metals selected from stainless, iron, copper, aluminum, magnesium, nickel, zinc, chromium, titanium, molybdenum, silicon, germanium and tantalum, and plates composed of an alloy(s) of the above metals.

In the present invention, in terms of providing a thin element, polymer films and metal films are preferable. Preferable polymer films have an oxygen transmission rate of $1\times10^{-3}$ $cm^3$/($m^2$·24h·atm) or less determined according to JIS K 7126-1987 and a water vapor transmission rate at 25±0.5° C. and 90±2% RH of $1\times10^3$ g/($m^2$·24 h) or less determined according to JIS K 7129-1992.

The sealing member may be made concave by sandblasting or chemical etching, for example.

The adhesive may be exemplified by light curing or heat curing adhesives containing reactive vinyl groups of an acrylic acid-based oligomer and/or methacrylic acid-based oligomer, moisture curing adhesives such as 2-cyanoacrylate, and heat and chemical curing adhesives (mixture of two types of adhesives) such as epoxy adhesives. In addition, hot-melt polyamides, hot-melt polyesters, hot-melt polyolefins, cationic UV curing epoxy resin adhesives may also be given as examples.

To prevent the organic EL element from being deteriorated by heat, preferable adhesives are curable at a temperature ranging from room temperature up to 80° C. In the adhesive, a desiccant may be dispersed. Application of the adhesive to a sealing area may be conducted using a commercially available dispenser or conducted by printing such as screen printing.

It is also preferable to form a layer as a sealing membrane containing an inorganic or organic compound. The sealing membrane is formed on the electrode which sandwiches the organic functional layer with the supporting substrate so as to cover the electrode and the organic functional layer and so as to contact to the supporting substrate. A material used for the sealing membrane may be any materials capable of suppressing intrusion of matters that cause deterioration such as water, oxygen and the like. Examples of the material include silicon oxide, silicon dioxide, silicon nitride and the like. To improve weakness of the sealing membrane, the sealing membrane preferably has a laminated structure constituted of the inorganic layer composed of the above inorganic material(s) and an organic layer composed of an organic material(s). The sealing membrane may be formed by vacuum deposition, sputtering, reactive sputtering, molecular beam epitaxy, cluster ion beam, ion plating, plasma polymerization, atmospheric pressure plasma polymerization, plasma CVD, laser CVD, heat CVD or coating, but not specifically limited thereto.

Inert gas such as nitrogen and argon or inert liquid such as fluorohydrocarbon and silicon oil are preferably provided between the sealing member and the display area by injection to provide a gas or liquid medium between the sealing member and a display area composed of the organic EL element(s) The gap between the sealing member and the display area may also be vacuum. Also a hygroscopic compound may be enclosed within the gap.

The hygroscopic compound may be exemplified by metal oxides such as sodium oxide, potassium oxide, calcium oxide, barium oxide, magnesium oxide, aluminum oxide; sulfates such as sodium sulfate, calcium sulfate, magnesium sulfate, cobalt sulfate; metallic halides such as calcium chloride, magnesium chloride, cesium fluoride, tantalum fluoride, cerium bromide, magnesium bromide, barium iodide and magnesium iodide; perchloric acids such as barium perchlorate and magnesium perchlorate. As for sulfates, metallic halides and perchloric acids, anhydrous salts thereof are preferably used.

Sealing includes casing-type sealing and contacting-type sealing. In terms of providing a thin element, contacting-type sealing is preferable. To produce a flexible organic EL element, a sealing member is required to be flexible, and thus contacting-type sealing is preferable.

Preferred embodiments for conducting contacting-type sealing will be described.

The sealing adhesive used in the present invention may be, for example, a heat curable adhesive or UV curable resin, preferably a heat curable adhesive such as epoxy resin, acrylic resin or silicone resin, and more preferably an epoxy heat curable adhering resin which has excellent humid and water resistance and causes small shrinkage in curing.

The moisture content in the sealing adhesive used in the present invention is preferably 300 ppm or less, more preferably 0.01 to 200 ppm, and most preferably 0.01 to 100 ppm.

The moisture content referred herein may be measured by any method, for example, by using a volumetric titrator (Karl Fischer), an infrared moisture gauge, a microwave transmission moisture gauge, gravimetry through heating and drying, GC/MS, IR, differential scanning calorimeter (DSC) or thermal desorption spectroscopy (TDS). The moisture content of a film, solid film or the like may be obtained with rise in pressure caused by water evaporation using a precision moisture meter AVM-3000 manufactured by OMNITEK.

In the present invention, the moisture content of the sealing adhesive may be controlled by putting the sealing adhesive into a nitrogen atmosphere wherein the dew point is −80° C. or less and the oxygen concentration is 0.08 ppm for a period adequately varied, or by drying the sealing adhesive by putting the sealing adhesive into vacuum at a pressure of less than 100 Pa for a period adequately varied. The sealing adhesive may be dried alone, or may be disposed on the sealing member and then dried together.

In the case of contacting-type sealing, as the sealing member, polyethylene terephthalate (PET) having a thickness of 50 μm on which an aluminum film having a thickness of 30 μm is formed is used. On the aluminum side of this sealing member, the sealing adhesive is uniformly applied using a dispenser, and then the resin substrate 1 is positioned with the sealing member 5. Thereafter, pressure bonding of the resin substrate 1 and the sealing member 5 is conducted (at 0.1 to 3 MPa) and the resin substrate 1 and the sealing member 5 are adhered to each other at 80 to 100° C. Contacting-type sealing is thus conducted.

Periods for heating and pressure bonding vary according to, for example, a type of an adhesive, the amount of adhesive or an area for sealing, but heating and pressure bonding may be conducted in conditions of temporary adhesion at a pressure of 0.1 to 3 MPa, heating at a temperature of 80 to 180° C. and heat curing for 5 seconds to 10 minutes.

It is preferable to use a heated pressure bonding roll because both heating and pressure bonding (temporary adhesion) can be simultaneously conducted and inner voids can be eliminated.

The layer of the adhesive may be formed by a coating method such as roll coating, spin coating, screen printing or spray coating, or printing, optionally using a dispenser according to a material.

Contacting-type sealing is covering with a cured resin causing no void between a sealing member and a substrate of an organic EL element. Examples of the sealing member include metals such as stainless, aluminum and magnesium alloy, plastics such as polyethylene terephthalate, polycarbonate, polystyrene, nylon and polyvinyl chloride, composites thereof and glass. When needed, particularly in the case of using a resin film, a sealing member on which a gas barrier layer composed of aluminum, aluminum oxide, silicon oxide or silicon nitride is formed can be used, like the resin substrate described above.

The gas barrier layer may be formed on the both or one surface of a sealing member by sputtering, deposition or the like before shaping the sealing member, or may be formed on the both or one surface of a sealing member by a method such as the above after sealing.

This gas barrier layer preferably has an oxygen transmission rate of $1 \times 10^{-3}$ ml/(m$^2 \cdot$24 h·atm) or less and a water vapor transmission rate at 25±0.5° C. and 90±2% RH of $1 \times 10^{-3}$ g/(m$^2 \cdot$24 h) or less.

The sealing member may be a film on which a metal foil such as an aluminum foil is provided. To form a polymer film on one side of a metal foil, a commonly-used laminating device may be used. An adhesive may be a polyurethane adhesive, polyester adhesive, epoxy adhesive or acrylic adhesive. A curing agent may be used in combination with the adhesive as needed. Lamination may be conducted by hot-melt lamination, extrusion lamination or co-extrusion lamination, and dry lamination is preferable.

When a metal foil is formed by sputtering, deposition or the like with a fluid electrode material such as an electro-conductive paste, the sealing member may formed by a way that is reverse to the above, namely, by forming a metal foil on a substrate of polymer film.

<<Protective Film, Protective Plate>>

A protective film or protective plate may be provided on the other side of the sealing membrane or sealing film, either of which is provided on the side sandwiching the organic functional layer with the supporting substrate, in order to improve mechanical strength of the organic EL element. It is preferable to provide the protective film or protective plate especially in the case of sealing with the sealing membrane because the sealing membrane is not so mechanically strong. Materials for the protective film or protective plate may be exemplified by a glass plate, a composite of polymer plate and film and a composite of metal plate and film, like the materials for sealing. To achieve light weight and thinness, polymer film is preferable.

In the present invention, it is preferable to provide a light-extracting member between the flexible supporting substrate and the anode, or at any position from the flexible supporting substrate to a side from which light is extracted.

The light-extracting member may be exemplified by a prism sheet, lens sheet and scattering sheet, and may also be exemplified by a diffracting grating or a scattering structure provided in any medium or at an interface where total reflection occurs.

Generally in the case of light emission from the side of a substrate of an organic electroluminescence element, part of light emitted from a light-emitting layer is totally reflected at the interface between a substrate and the air, resulted in loss of light. To solve this problem, the surface of the substrate is treated to form prism or lens structures, or a prism sheet, lens sheet or scattering sheet is pasted on the surface of the substrate. Accordingly, total reflection is suppressed and efficiency of light extraction is improved.

To improve efficiency of light extraction, there is a known method for introducing a diffraction grating or a scattering structure in any medium or at an interface where total reflection occurs.

<<Method for Manufacturing Organic EL Element>>

As an example of the method for manufacturing the organic EL element of the present invention, a method for manufacturing an organic EL element composed of anode/electron hole-injecting layer/electron hole-transporting layer/light-emitting layer/electron-transporting layer/electron-injecting layer/cathode will be described.

The anode is obtained by forming a thin film having a thickness of 1 μm or less, preferably 10 to 200 nm, and composed of a desired electrode material, for example, a material for an anode on a suitable base by a method for forming thin layers such as deposition or sputtering.

Subsequently, the organic functional layer (organic compound thin film) as a constituent of the organic EL element, i.e., the layer including the electron hole-injecting layer, the electron hole-transporting layer, the light-emitting layer, the electron-transporting layer and the electron-injecting layer, is formed on the anode.

A method for forming the organic functional layer mainly includes steps of applying and stacking a solution for each layer of the organic functional layer directly or indirectly on the anode on the supporting substrate and drying each of the solution. The applying step and the drying step may be conducted in the atmosphere. Preferably, the drying step is conducted in an inert gas atmosphere such as a nitrogen atmosphere, and more preferably, the applying step is also conducted in an inert, gas atmosphere.

Concentration of water and oxygen in an inert gas atmosphere are preferably 100 ppm or less, preferably 10 ppm or less, and more preferably 1 ppm or less.

A method for forming the layers of the organic functional layer may be deposition, a wet process (such as spin coating, casting, die coating, blade coating, roll coating, ink jetting, printing, spray coating, curtain coating, Langmuir Blodgett (LB) method). Preferably, at least the electron hole-injecting layer is formed by a wet process.

In forming layers of the organic functional layer other than the electron hole-injecting layer, a wet process is preferable for the present invention, because uniform layers can be formed and pinholes are hardly formed, for example. Particularly, the layers are preferably formed by an application method such as spin coating, casting, die coating, blade coating, roll coating and ink jetting.

Examples of liquid medium dissolving or dispersing a material (a) for the organic EL element therein include ketones such as methylethyl ketone and cyclohexanone; aliphatic acid esters such as ethyl acetate; halogenated hydrocarbons such as dichlorobenzene; aromatic hydrocarbons such as toluene, xylene, mesitylene and cyclohexylbenzene; aliphatic: hydrocarbons such as cyclohexane, decaline and dodecane; and organic solvents such as dimethyl formamide (DMF) and dimethyl sulfoxide (DMSO).

Dispersion can be performed by, for example, ultrasonic wave dispersion, high shearing force dispersion or medium dispersion.

Preparation of a solution by dissolving or dispersing a material(s) for the organic EL element of the present invention in liquid medium is preferably conducted in an inert gas atmosphere, and preferably the solutions are not exposed to an application atmosphere until the respective solutions are applied directly or indirectly on the substrate by the above-described wet process.

The steps of applying, stacking and drying the solutions may be conducted by single wafer production system or line production system. An atmosphere for applying the solutions may be shared. In terms of effects from solvents that vaporize, it is preferable that booths for applying the respective solutions are enclosed with walls or the like and circulations of the atmospheres are independent to each other. The drying step may be conducted during conveyance on the line. In terms of productivity, the drying step may be conducted after stacking or non-contact winding to form a roll.

After forming these layers, a thin film composed of the material for the cathode is formed thereon so as to have a thickness of 1 μm or less, preferably in a range of 50 to 200 nm on the outermost layer by a method such as vapor deposition or sputtering as the cathode to manufacture a desired organic EL element.

After the heating, contacting-type sealing or bonding of the sealing member and the electrodes and the supporting substrate with the adhesive is conducted, and the organic EL element is then obtained.

<<Application>>

The organic EL element of the present invention may be used for display devices, displays and various light sources.

Examples of a light source include various applications such as a household lighting, an in-car lighting, a backlight of a clock or liquid crystal display, a billboard, a traffic signal, a light source of an optical storage medium, a light source of an electro photocopier, a light, source of an optical communication processer, a light source of an optical sensor and a general electric home appliance which requires a display device. Particularly, the organic element, of the present invention may be effectively used for a backlight of a liquid crystal display device combined with a color filter, or a light source for lighting.

In the organic EL element of the present invention, patterning may be conducted in forming a film using a metal mask or by inkjet printing method or the like as needed. Patterning may be conducted only on the electrode(s), on the electrodes and the light-emitting layer, or on all of the layers of the element. In manufacturing the element, any conventionally known method(s) may be used.

EXAMPLES

The present invention will be described in detail with reference to Examples, but is not limited thereto. In Examples, "part(s)" and "%" means "part(s) by mass" and "% by mass" unless described otherwise. A compound used in Examples is shown below.

[Chemical formula 36]

Compound A

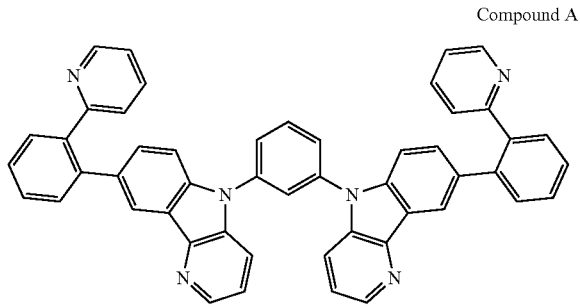

Example 1

<<Preparation of Organic EL Element 6>>: Present Invention (Preparation of Flexible Film)

As a flexible film, polyethylene naphthalate film (manufactured by Teijin DuPont Films Japan Limited, hereinafter abbreviated as PEN) was used. On the entire surface of the side on which an anode was to be provided, a 500 nm-thick gas barrier film of an inorganic compound composed of SiOx was formed without intermission using an atmospheric pressure plasma discharge processor configured as described in Japanese Patent Application Laid-open Publication No. 2004-68143. A flexible gas barrier film having an oxygen transmission rate of 0.001 $cm^3/(m^2 \cdot 24 \ h \cdot atm)$ or less and a water vapor transmission rate of 0.001 $g/(m^2 \cdot 24 \ h)$ or less was thus prepared.

(Preparation of Anode)

On the prepared flexible gas barrier film, a film having a thickness of 120 nm was formed with ITO (indium tin oxide) by sputtering followed by patterning by photolithography. An anode was thus prepared.

The formed pattern had a light-emitting area of 50 square millimeter.

(Preparation of Electron Hole-Injecting Layer)

The patterned ITO substrate was subjected to ultrasonic washing with isopropyl alcohol, drying in a dry nitrogen atmosphere, and UV ozone washing for 5 minutes. On this substrate, a film was formed with a 70% solution of poly (3,4-ethylenedioxythiophene)-polystylene sultanate (abbreviated as PEDOT/PSS, P AI 4083 manufactured by Bayer AG) in pure water by spin coating at 3000 rpm for 30 seconds.

The formation of the film was conducted in the atmosphere, and thereafter, drying was conducted at 200° C. for an hour. An electron hole-injecting layer having a thickness of 30 nm was thus prepared.

(Preparation of Electron Hole-Transporting Layer)

The resulting substrate was put in a nitrogen atmosphere, and a film was formed thereon with a 0.5% solution of the exemplary compound (60) having a molecular weight of 80,000, which is an electron hole-transporting material, in chlorobenzene by spin coating at 1500 rpm for 30 seconds, followed by drying at 130° C. for 30 minutes. An electron hole-transporting layer having a thickness of 30 nm was thus prepared.

(Preparation of Light-Emitting Layer)

Subsequently, a film was formed with respective compounds below in the following composition ratios for a light-emitting layer by spin coating at 1500 rpm for 30 seconds, followed by drying at 120° C. for 30 minutes. A light-emitting layer having a thickness of 40 nm was thus prepared.

(Compounds for Light-Emitting Layer)

| Non-light-emitting organic materials (a-6, a-41, a-31) | |
|---|---|
| a-6 | 12.000 parts by mass |
| a-41 | 1.970 parts by mass |
| a-31 | 0.170 part by mass |

The above compounds, a-6, a-41 and a-31, are host compounds.

| Light-emitting dopants (D-66, D-67, D-80) | |
|---|---|
| D-66 | 2.450 parts by mass |
| D-67 | 0.025 part by mass |
| D-80 | 0.025 part by mass |
| Solvent | |
| Toluene | 2.000 parts by mass |

(Preparation of Electron-transporting Layer)

Subsequently, a film was formed with a solution where 20 mg of the compound A was dissolved in 4 ml of tetrafluoro propanol (TFPO) by spin coating at 1500 rpm for 30 seconds, followed by drying at 120° C. for 30 minutes. An electron-transporting layer having a thickness of 30 nm was thus prepared.

(Preparation of Electron-Injecting Layer and Cathode)

Thereafter, the resulting substrate (i.e., a half-formed element directly or indirectly on which layers up to the electron-transporting layer had been formed) was put in a vacuum deposition device. A molybdenum resistive heating boat in which potassium fluoride was placed was also put in the vacuum deposition device. Then the vacuum chamber was depressurized by $4 \times 10^{-5}$ Pa, and the boat was electrified to be heated so as to form an electron injecting layer having a thickness of 2 nm with potassium fluoride at a rate of 0.02 nm/sec on the electron-transporting layer. Thereafter, aluminum was vapor-deposited so as to form a cathode having a thickness of 100 nm on the electron-injecting layer.

(Sealing and Preparation of Organic EL Element)

Subsequently, a sealing member was adhered to the resulting substrate using a commercially-available roll lamination device to prepare an organic EL element 6 (the present invention).

As the sealing member, a 30 μm-thick flexible aluminum foil (manufactured by TOYO ALUMINIUM K.K.) on which a 12 μm-thick polyethylene terephthalate film was formed using an adhesive for dry lamination so as to obtain a thickness of the adhesive layer of 1.5 μm, which adhesive is a two-liquid reaction type urethane adhesive, was used.

On a side for adhesion (glossy side) of the aluminum foil, a heat curing adhesive as the sealing adhesive was evenly applied using a dispenser to obtain a thickness of 20 μm, followed by drying in vacuum at a pressure of 100 Pa or less for 12 hours.

Thereafter, the sealing member was put in a nitrogen atmosphere wherein the dew point was 80° C. and the oxygen concentration was 0.8 ppm and was dried for not less than 12 hours so as to adjust the moisture content in the sealing adhesive to 100 ppm or less.

The heat curing adhesive was an epoxy adhesive composed of a mixture of the following (A) to (C).

(A) bisphenol A diglycidyl ether (DGEBA)
(B) dicyandiamide (DICY)
(C) epoxy adduct curing accelerator As described above, the resulting substrate to be sealed was arranged on and adhered to an extracting electrode and a junction(s) of an electrode lead(s) so as to cover the extracting electrode and the junction(s) of the electrode lead(s), and the contacting-type sealing was conducted in the condition that a temperature of a pressure bonding roll was 120° C., pressure of bonding was 0.5 MPa and a rate of the device of 0.3 m/minute to form an element as illustrated in the FIGURE. The organic EL element 6 (the present invention) was thus prepared.

<<Preparation of Organic EL Elements 1 to 5 (Comparative Examples), 7 to 13 (Present Invention) and 15 to 21 (Present Invention)>>

Organic EL elements 1 to 5 (comparative examples), 7 to 13 (the present invention) and 15 to 21 (the present invention) were prepared by the same way as the organic EL element 6 was prepared except that non-light-emitting organic materials and light-emitting dopants used for forming light-emitting layers were as listed in Tables 1, 2 and 3.

<<Preparation of Organic EL Element 14 (Present Invention)>>

An organic EL element 14 was prepared by the same way as the organic EL element 6 was prepared except that compounds used for forming a light-emitting layer were as described below.

(Compounds for Light-Emitting Layer)

| Non-light-emitting organic materials (a-6, a-10, a-12, a-17, a-24, a-26, a-30, a-31, a-33, a-41) | |
|---|---|
| a-6 | 1.414 parts by mass |
| a-10 | 1.414 parts by mass |
| a-12 | 1.414 parts by mass |
| a-17 | 1.414 parts by mass |
| a-24 | 1.414 parts by mass |
| a-26 | 1.414 parts by mass |
| a-30 | 1.414 parts by mass |
| a-31 | 1.414 parts by mass |
| a-33 | 1.414 parts by mass |
| a-41 | 1.414 parts by mass |

The above compounds, a-6, a-10, a-12, a-17, a-24, a-26, a-30, a-31, a-33 and a-41, are host compounds.

| Light-emitting dopants (D-66, D-67, D-80) | |
|---|---|
| D-66 | 2.450 parts by mass |
| D-67 | 0.025 part by mass |
| D-80 | 0.025 part by mass |
| Solvent | |
| Toluene | 2.000 parts by mass |

TABLE 1

| Element | | Non-light-emitting organic material | | | | | Light-emitting dopant | | | Note |
|---|---|---|---|---|---|---|---|---|---|---|
| | | $H_1$ | $H_2$ | $H_3$ | $H_4$ | $H_5$ | Dopant 1 | Dopant 2 | Dopant 3 | |
| 1 | Type of Molecule | a-6 | — | — | — | — | D-66 | D-67 | D-80 | Comparison |
| | (Molecular weight) | (569) | | | | | | | | |
| | Content (% by mass) | 85 | — | — | — | — | 14.7 | 0.15 | 0.15 | |
| 2 | Type of Molecule | a-6 | a-41 | — | — | — | D-66 | D-67 | D-80 | Comparison |
| | (Molecular weight) | (569) | (499) | | | | | | | |
| | Content (% by mass) | 70 | 15 | — | — | — | 14.7 | 0.15 | 0.15 | |
| 3 | Type of Molecule | a-6 | a-41 | a-31 | — | — | D-66 | D-67 | D-80 | Comparison |
| | (Molecular weight) | (569) | (499) | (472) | | | | | | |
| | Content (% by mass) | 70 | 14.9 | 0.1 | — | — | 14.7 | 0.15 | 0.15 | |
| 4 | Type of Molecule | a-40 | a-41 | a-31 | — | — | D-66 | D-67 | D-80 | Comparison |
| | (Molecular weight) | (1778) | (499) | (472) | | | | | | |
| | Content (% by mass) | 70 | 10 | 5 | — | — | 14.7 | 0.15 | 0.15 | |
| 5 | Type of Molecule | PVK (*) | a-41 | a-31 | — | — | D-66 | D-67 | D-80 | Comparison |
| | (Molecular weight) | (Mn: 50000) | (499) | (472) | | | | | | |
| | Content (% by mass) | 70 | 10 | 5 | — | — | 14.7 | 0.15 | 0.15 | |

TABLE 1-continued

| Element | | Non-light-emitting organic material | | | | | Light-emitting dopant | | | Note |
|---|---|---|---|---|---|---|---|---|---|---|
| | | H₁ | H₂ | H₃ | H₄ | H₅ | Dopant 1 | Dopant 2 | Dopant 3 | |
| 6 | Type of Molecule | a-6 | a-41 | a-31 | — | — | D-66 | D-67 | D-80 | Present Invention |
| | (Molecular weight) | (569) | (499) | (472) | | | | | | |
| | Content (% by mass) | 70 | 14 | 1 | — | — | 14.7 | 0.15 | 0.15 | |
| 7 | Type of Molecule | a-6 | a-41 | a-31 | — | — | D-66 | D-67 | D-80 | Present Invention |
| | (Molecular weight) | (569) | (499) | (472) | | | | | | |
| | Content (% by mass) | 70 | 10 | 5 | — | — | 14.7 | 0.15 | 0.15 | |

(*): Mn represents a number average molecular weight

TABLE 2

| Element | | Non-light-emitting organic material | | | | | Light-emitting dopant | | | Note |
|---|---|---|---|---|---|---|---|---|---|---|
| | | H₁ | H₂ | H₃ | H₄ | H₅ | Dopant 1 | Dopant 2 | Dopant 3 | |
| 8 | Type of Molecule | a-6 | a-41 | a-31 | a-30 | — | D-66 | D-67 | D-80 | Present Invention |
| | (Molecular weight) | (569) | (499) | (472) | (402) | | | | | |
| | Content (% by mass) | 70 | 10 | 2.5 | 2.5 | — | 14.7 | 0.15 | 0.15 | |
| 9 | Type of Molecule | a-6 | a-41 | a-31 | a-30 | Carbazol | D-66 | D-67 | D-80 | Present Invention |
| | (Molecular weight) | (569) | (499) | (472) | (402) | (167) | | | | |
| | Content (% by mass) | 70 | 10 | 2.5 | 2.4 | 0.1 | 14.7 | 0.15 | 0.15 | |
| 10 | Type of Molecule | a-6 | a-41 | a-31 | a-30 | Carbazol | D-66 | D-67 | D-80 | Present Invention |
| | (Molecular weight) | (569) | (499) | (472) | (402) | (167) | | | | |
| | Content (% by mass) | 70 | 10 | 2.5 | 1.5 | 1 | 14.7 | 0.15 | 0.15 | |
| 11 | Type of Molecule | a-31 | a-41 | a-6 | a-30 | Carbazol | D-66 | D-67 | D-80 | Present Invention |
| | (Molecular weight) | (472) | (499) | (569) | (402) | (167) | | | | |
| | Content (% by mass) | 70 | 10 | 2.5 | 1.5 | 1 | 14.7 | 0.15 | 0.15 | |
| 12 | Type of Molecule | a-6 | a-41 | a-31 | a-30 | Anthracene | D-66 | D-67 | D-80 | Present Invention |
| | (Molecular weight) | (569) | (499) | (472) | (402) | (178) | | | | |
| | Content (% by mass) | 70 | 10 | 2.5 | 1.5 | 1 | 14.7 | 0.15 | 0.15 | |
| 13 | Type of Molecule | a-6 | a-41 | a-31 | a-33 | a-30 | D-66 | D-67 | D-80 | Present Invention |
| | (Molecular weight) | (569) | (499) | (472) | (472) | (402) | | | | |
| | Content (% by mass) | 70 | 10 | 2.5 | 1.5 | 1 | 14.7 | 0.15 | 0.15 | |

TABLE 3

| Element | | Non-light-emitting organic material | | | | | Light-emitting dopant | | | Note |
|---|---|---|---|---|---|---|---|---|---|---|
| | | H₁ | H₂ | H₃ | H₄ | H₅ | Dopant 1 | Dopant 2 | Dopant 3 | |
| 15 | Type of Molecule | a-38 | a-4 | a-12 | — | — | D-66 | D-67 | D-80 | Present Invention |
| | (Molecular weight) | (890) | (560) | (574) | | | | | | |
| | Content (% by mass) | 70 | 10 | 5 | — | — | 14.7 | 0.15 | 0.15 | |
| 16 | Type of Molecule | a-19 | a-16 | a-22 | — | — | D-66 | D-67 | D-80 | Present Invention |
| | (Molecular weight) | (890) | (814) | (560) | | | | | | |
| | Content (% by mass) | 70 | 10 | 5 | — | — | 14.7 | 0.15 | 0.15 | |
| 17 | Type of Molecule | a-3 | a-31 | a-41 | Carbazol | — | D-66 | D-67 | D-80 | Present Invention |
| | (Molecular weight) | (514) | (482) | (498) | (167) | | | | | |
| | Content (% by mass) | 70 | 10 | 2.5 | 2.5 | — | 14.7 | 0.15 | 0.15 | |
| 18 | Type of Molecule | a-28 | a-41 | a-3 | Carbazol | — | D-66 | D-67 | D-80 | Present Invention |
| | (Molecular weight) | (464) | (498) | (514) | (167) | | | | | |
| | Content (% by mass) | 70 | 10 | 2.5 | 2.5 | — | 14.7 | 0.15 | 0.15 | |
| 19 | Type of Molecule | a-31 | a-39 | a-28 | a-30 | — | D-66 | D-67 | D-80 | Present Invention |
| | (Molecular weight) | (482) | (846) | (464) | (408) | | | | | |
| | Content (% by mass) | 70 | 10 | 2.5 | 2.5 | — | 14.7 | 0.15 | 0.15 | |
| 20 | Type of Molecule | a-14 | a-35 | a-11 | a-1 | a-30 | D-66 | D-67 | D-80 | Present Invention |
| | (Molecular weight) | (650) | (636) | (573) | (498) | (402) | | | | |
| | Content (% by mass) | 70 | 10 | 2.5 | 1.5 | 1 | 14.7 | 0.15 | 0.15 | |
| 21 | Type of Molecule | a-20 | a-9 | a-26 | a-31 | a-30 | D-66 | D-67 | D-80 | Present Invention |
| | (Molecular weight) | (650) | (560) | (540) | (482) | (402) | | | | |
| | Content (% by mass) | 70 | 10 | 2.5 | 1.5 | 1 | 14.7 | 0.15 | 0.15 | |

<<Evaluation of Organic EL Elements 1 to 21>>

The respective organic EL elements 1 to 5 (comparative examples) 6 to 14 (the present invention) and 15 to 21 (the present invention) were evaluated as to the followings.

<<Power Efficiency (Efficiency)>>

Power efficiencies (lm/W) of the respective organic EL elements to which a constant current of 2.5 mA/cm$^2$ was applied were measured with a spectroradiometer CS-2000 (manufactured by Konica Minolta Sensing Inc.

The power efficiency of each of the organic EL elements was described in a relative value defining power efficiency of the organic EL element 1 (comparative example) as 1.00. A Higher value represents higher efficiency.

<<Stability in Continuous Driving (Lifetime)>>

Each of the organic EL elements was put on a cylinder with a radius of 5 cm so as to bend the organic EL element, and the bent organic EL element was continuously driven. Luminance of each of the bent organic EL elements was measured with a spectroradiometer CS-2000 (manufactured by Konica Minolta Sensing Inc.). A time period until the luminance decreased by half (LT50) was obtained.

The driving was conducted in the condition that current voltage was 4000 cd/m$^2$ at the start of the continuous driving.

Relative values of LT50s of the organic EL elements were calculated defining LT50 of the organic EL element 1 (comparative example 1) as 100. These relative values were indicators of stabilities in continuous driving. A higher value represents a longer lifetime.

<<Storage Stability in High Temperature (Change in Voltage After Storage in High Temperature)>>

Each of the organic EL elements was put on a cylinder with a radius of 5 cm so as to bend the organic EL element. Voltage as to each of the bend organic EL elements to which a constant current of 2.5 mA/cm was applied was measured (an initial state).

The bent organic EL elements on the cylinders were put and kept in a thermostatic chamber at 85° C. for 500 hours. Subsequently, the bent organic EL elements were taken out from the thermostatic chamber, and voltage as to each of the bent organic EL elements to which a constant current of 2.5 mA/cm$^2$ applied was measured (a state after storage in high temperature).

Change in voltage is a difference between voltage at the state after storage in high temperature (voltage upon application of a constant current of 2.5 mA/cm$^2$) and voltage at the initial state (voltage upon application of a constant current of 2.5 mA/cm$^2$).

Results from the evaluations are shown in Table 4.

TABLE 4

| Element | Efficiency | Lifetime | Change in Voltage after strage in high temperature | Note |
|---|---|---|---|---|
| 1 | 100 | 100 | 2.0 | Comparison |
| 2 | 100 | 100 | 1.9 | Comparison |
| 3 | 103 | 104 | 1.9 | Comparison |
| 4 | 108 | 107 | 1.8 | Comparison |
| 5 | 110 | 103 | 2.4 | Comparison |
| 6 | 112 | 115 | 1.5 | Present invention |
| 7 | 120 | 123 | 1.3 | Present invention |
| 8 | 120 | 123 | 1.3 | Present invention |
| 9 | 122 | 123 | 1.3 | Present invention |
| 10 | 135 | 130 | 1.2 | Present invention |
| 11 | 125 | 123 | 1.4 | Present invention |
| 12 | 123 | 124 | 1.3 | Present invention |
| 13 | 129 | 132 | 0.9 | Present invention |
| 14 | 123 | 127 | 0.6 | Present invention |
| 15 | 111 | 113 | 1.6 | Present invention |
| 16 | 112 | 112 | 1.6 | Present invention |
| 17 | 121 | 125 | 1.3 | Present invention |
| 18 | 123 | 123 | 1.3 | Present invention |
| 19 | 122 | 123 | 1.3 | Present invention |
| 20 | 131 | 132 | 0.7 | Present invention |
| 21 | 133 | 131 | 0.7 | Present invention |

It is evident from the results shown in Table 4 that the organic EL elements 6 to 21 of the present invention is superior to the organic EL elements 1 to 5 in all respects including the efficiency and change in voltage after storage in high temperature (storage stability in high temperature)

In addition, Table 4 shows that in the organic EL elements 6 to 21 of the present invention, the efficiencies and lifetimes of the present invention are further improved as the number of types of the non-light-emitting organic materials used in the light-emitting layer increases from 3 or 4 to 4 or 5.

In addition, in the organic EL elements 13, 14, 20 and 21, because a difference between the maximum molecular weight among molecular weights of the five or more types of the non-light-emitting organic materials and the minimum molecular weight among molecular weights of the five or more types of non-light-emitting organic materials is within 250, remarkable storage stability in high temperature is achieved.

Therefore, it is clearly revealed that using three or more types of the non-light-emitting organic materials in the light-emitting layer can achieve an organic EL element having high power efficiency, high stability in long term driving and high storage stability in high temperature.

Example 2

<<Preparation of Organic EL Element 23 (Present Invention)>>: Present Invention

An organic EL element 23 was prepared by the same way as the organic EL elements 1 to 21 in Example 1 were prepared except that layers from the electron hole-transporting layer to the electron-transporting layer were formed by deposition, (Preparation of Electron Hole-Transporting Layer)

A substrate (i.e., a half-formed element directly or indirectly on which layers up to the electron hole-injecting layer had been formed) was put in a vacuum deposition device. A molybdenum resistive heating boat in which α-NPD was placed was also put in the vacuum deposition device. Then the vacuum chamber was depressurized by 4×10$^{-5}$ Pa, and the boat was electrified to be heated so as to form an electron hole-transporting layer having a thickness of 20 nm with α-NPD at a rate of 0.10 nm/sec on the electron hole-injecting layer, (Preparation of Light-Emitting Layer 1)

Subsequently, molybdenum resistive heating boats in each of which each compound for the light-emitting layer shown below was placed were put in a vacuum deposition device. Then the vacuum chamber was depressurized by 4×10$^{-5}$ Pa, and the boats were electrified to be heated so as to form a light-emitting layer 1 having a thickness of 20 nm by co-deposition on the electron hole-transporting layer. The total deposition rate of these compounds for the light-emitting layer 1 was 1.0 nm/sec.

(Compounds for Light-Emitting Layer)

| Non-light-emitting organic materials (a-6, a-31) | |
|---|---|
| a-6 | 70.000 parts by mass |
| a-31 | 20.000 parts by mass |

The above compounds, a-6 and a-31, are host compounds.

| Light-emitting dopants (D-67, D-80) | |
|---|---|
| D-67 | 8.000 parts by mass |
| D-80 | 2.000 parts by mass |

(Preparation of Light-Emitting Layer 2)

Thereafter, molybdenum resistive heating boats in each of which each compound for the light-emitting layer below was placed were put in a vacuum deposition device. Then the vacuum chamber was depressurized by $4\times10^{-5}$ Pa, and the boats were electrified to be heated so as to form a light-emitting layer 2 having a thickness of 20 nm by co-deposition on the light-emitting layer 1. The total deposition rate of these compounds for the light-emitting layer 2 was 1.0 nm/sec.

(Compounds for Light-Emitting Layer)

| Non-light-emitting organic materials (a-6, a-41) | |
|---|---|
| a-41 | 70.000 parts by mass |
| a-6 | 12.000 parts by mass |

The compound a-41 is a host compound.

| Light-emitting dopants (D-66) | |
|---|---|
| D-66 | 18.000 parts by mass |

(Preparation of Electron-transporting Layer)

Thereafter, a molybdenum resistive heating boat in which the compound A was placed was put in the vacuum deposition device. Then the vacuum chamber was depressurized by $4\times10^{-5}$ Pa, and the boat was electrified to be heated so as to form an electron-transporting layer having a thickness of 20 nm with the compound A at a rate of 0.10 nm/sec on the light-emitting layer 2.

<<Preparation of Organic EL Elements 22 (Comparative Example), 24 (Present Invention) and 25 (Present Invention)>>

Organic EL elements 22, 24 and 25 were prepared by the same way as the organic EL element 23 was prepared except that compounds for forming the light-emitting layer were as listed in Table 5.

TABLE 5

| | | Light-emitting layer 1 | | | | Light-emitting layer 2 | | | | |
| | | Non-light-emitting organic material | | Light-emitting dopant | | Non-light-emitting organic material | | | Light-emitting dopant | |
| Element | | $H_1$ | $H_2$ | Dopant 1 | Dopant 2 | $H_3$ | $H_4$ | $H_5$ | Dopant 3 | Note |
|---|---|---|---|---|---|---|---|---|---|---|
| 22 | Type of Molecule | a-6 | — | D-67 | D-80 | a-41 | — | — | D-66 | Comparison |
| | (Molecular weight) | (569) | | | | (499) | | | | |
| | Content (% by mass) | 90.0 | — | 8.0 | 2.0 | 82.0 | — | — | 18.0 | |
| 23 | Type of Molecule | a-6 | a-31 | D-67 | D-80 | a-41 | a-6 | — | D-66 | Present Invention |
| | (Molecular weight) | (569) | (472) | | | (499) | (569) | | | |
| | Content (% by mass) | 70.0 | 20.0 | 8.0 | 2.0 | 70.0 | 12.0 | — | 18.0 | |
| 24 | Type of Molecule | a-6 | a-31 | D-67 | D-80 | a-41 | a-1 | — | D-66 | Present Invention |
| | (Molecular weight) | (569) | (472) | | | (499) | (499) | | | |
| | Content (% by mass) | 70.0 | 20.0 | 8.0 | 2.0 | 70.0 | 12.0 | — | 18.0 | |
| 25 | Type of Molecule | a-6 | a-31 | D-67 | D-80 | a-41 | a-1 | a-17 | D-66 | Present Invention |
| | (Molecular weight) | (569) | (472) | | | (499) | (499) | (474) | | |
| | Content (% by mass) | 70.0 | 20.0 | 8.0 | 2.0 | 60.0 | 15.0 | 7.0 | 18.0 | |

<<Evaluation of Organic EL Elements 22 to 25>>

Each of the prepared organic EL elements 22 to 25 was evaluated as to power efficiency (efficiencies) stability in continuous driving (lifetimes) and storage stability in high temperature by the same ways as the organic elements 1 to 21 were evaluated in Example 1.

Results from the evaluations are shown in Table 6,

TABLE 6

| Element | Efficiency | Lifetime | Change in Voltage after strage in high temperature | Note |
|---|---|---|---|---|
| 22 | 100 | 100 | 1.7 | Comparison |
| 23 | 111 | 110 | 1.4 | Present Invention |
| 24 | 112 | 114 | 1.4 | Present Invention |
| 25 | 115 | 118 | 1.3 | Present Invention |

It is evident from results shown in Table 6 that the organic EL elements 23 to 25 of the present invention are superior to the organic EL element 22 as the comparative example in all respects including the efficiency and change in voltage after storage in high temperature (storage stability in high temperature)

Hence, it is evident that the present invention can provide an organic EL element having high power efficiency, high stability in long term driving and high storage stability in high temperature because three or more types of the non-light-emitting organic materials are used for the light-emitting layer(s).

INDUSTRIAL APPLICABILITY

The organic EL element of the present invention can be applied to low-power image displaying devices, low-power lighting devices and so forth because the organic EL element of the present invention achieves high efficiency of light emission, long lifetime of light emission and high storage stability in high temperature.

DESCRIPTION OF REFERENCE NUMERALS

1 Flexible supporting substrate
2 Anode
3 Electron hole-injecting layer
4 Electron hole-transporting layer
5 Light-emitting layer
6 Electron-transporting layer
7 Electron-injecting layer
8 Cathode
9 Sealing adhesive
10 Flexible sealing member
20 Organic functional layer

The invention claimed is:

1. An organic electroluminescence element comprising an anode, a cathode and one or more light-emitting layers provided between the anode and the cathode,
wherein
at least one of the one or more light-emitting layers includes at least one type of a light-emitting dopant and at least three types of non-light-emitting organic materials,
a largest molecular weight among molecular weights of the at least three types of the non-light-emitting organic materials is 1500 or less,
a minimum content of the at least three types of the non-light-emitting organic materials is 1% by mass or more, and
the non-light-emitting organic materials are represented by a following general formula (2):

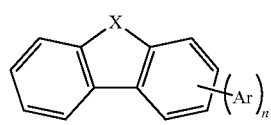

General formula (2)

wherein X represents NR', O, S, PR', PR'R"R"', CR'R" or SiR'R"; R', R" and R"' each represent a hydrogen atom or a substituent; Ar represents an aromatic hydrocarbon ring or an aromatic hetero ring; and n represents an integer from 0 to 8.

2. The organic electroluminescence element of claim 1, wherein at least one of the at least three types of the non-light-emitting organic materials is a compound represented by a following general formula (3):

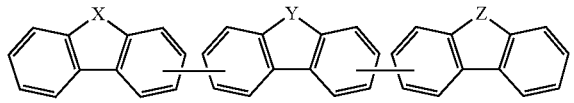

General formula (3)

wherein X, Y and Z each represent NR', O, S, PR', PR'R"R"', CR'R" or SiR'R"; R', R" and R"' each represent a hydrogen atom or a substituent; and a benzene ring optionally includes a substituent.

3. The organic electroluminescence element of claim 1, wherein
five types of the non-light-emitting organic materials represented by the general formula (2) are contained.

4. The organic electroluminescence element of claim 1, wherein
a content (% by mass) of each of the at least three types of the non-light-emitting organic materials increases with increase of molecular weight of each of the at least three types of the non-light-emitting organic materials.

5. The organic electroluminescence element of claim 1, wherein
among molecular weights of the at least three types of the non-light-emitting organic materials represented by the general formula (2), a difference between a largest molecular weight M (max) and a smallest molecular weight M (min) is less than 250.

6. The organic electroluminescence element of claim 1, wherein
the at least one type of the light-emitting dopant is a phosphorescence-emitting dopant.

7. The organic electroluminescence element of claim 6, wherein
the phosphorescence-emitting dopant is represented by a following general formula (1):

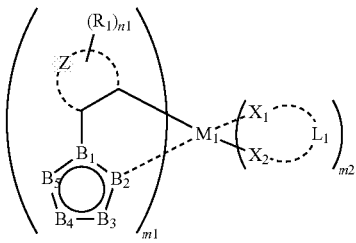

General formula (1)

wherein $R_1$ represents a substituent; Z represents a non-metal atom group necessary for forming a five to seven-membered ring; n1 represents an integer from 0 to 5; $B_1$ to $B_5$ each represent a carbon atom, a nitrogen atom, an oxygen atom or a sulfur atom, and at least one of $B_1$ to $B_5$ represents a nitrogen atom; $M_1$ represents a transition metal of Group 8 to 10 on a periodic table; $X_1$ and $X_2$ each represent a carbon atom, a nitrogen atom or an oxygen atom; $L_1$ represents a atom group forming a bidentate ligand with $X_1$ and $X_2$; m1 represents an integer 1, 2 or 3; m2 represents an integer 0, 1 or 2; and m1+m2 is 2 or 3.

* * * * *